(12) United States Patent
Levite et al.

(10) Patent No.: US 7,951,775 B2
(45) Date of Patent: May 31, 2011

(54) METHODS AND PHARMACEUTICAL COMPOSITIONS FOR GNRH-I AND GNRH-II MODULATION OF T-CELL ACTIVITY, ADHESION, MIGRATION AND EXTRAVASATION

(76) Inventors: Mia Levite, Savyon (IL); Yitzhak Koch, Rehovot (IL)

(*) Notice: Subject to any disclaimer, the term of this patent is extended or adjusted under 35 U.S.C. 154(b) by 686 days.

(21) Appl. No.: 10/498,346

(22) PCT Filed: Dec. 17, 2002

(86) PCT No.: PCT/IL02/01014
§ 371 (c)(1),
(2), (4) Date: Jun. 17, 2004

(87) PCT Pub. No.: WO03/051272
PCT Pub. Date: Jun. 26, 2003

(65) Prior Publication Data
US 2005/0158309 A1   Jul. 21, 2005

(30) Foreign Application Priority Data
Dec. 17, 2001 (IL) .......................................... 147138

(51) Int. Cl.
*A61K 38/09* (2006.01)
*A61K 39/395* (2006.01)
(52) U.S. Cl. .................. 514/10.3; 514/21.6; 424/143.1; 424/144.1
(58) Field of Classification Search .......................... None
See application file for complete search history.

(56) References Cited

U.S. PATENT DOCUMENTS

| | | | |
|---|---|---|---|
| 5,140,009 A | 8/1992 | Haviv et al. | |
| 5,574,011 A | 11/1996 | Tien | |
| 5,593,965 A | 1/1997 | Lovas et al. | |
| 5,744,450 A | 4/1998 | Hoeger et al. | |
| 5,760,000 A | 6/1998 | Habibi | |
| 5,925,730 A | 7/1999 | Semple et al. | |
| 5,985,901 A | 11/1999 | Goulet et al. | |
| 6,025,366 A | 2/2000 | Walsh et al. | |
| 6,077,858 A | 6/2000 | Goulet et al. | |
| 6,211,224 B1 | 4/2001 | Chu et al. | |
| 6,228,867 B1 | 5/2001 | Walsh et al. | |
| 6,274,562 B1 | 8/2001 | Baserga et al. | |
| 6,303,123 B1 | 10/2001 | Grimes et al. | |
| 6,323,179 B1 * | 11/2001 | Siler-Khodr | |
| 2005/0158909 A1 | 7/2005 | Milliron et al. | |

FOREIGN PATENT DOCUMENTS

| WO | WO 97/39721 | 10/1997 |
|---|---|---|
| WO | WO 99/50393 | 7/1999 |
| WO | 0001403 A1 | 1/2000 |
| WO | 0012115 A1 | 3/2000 |

OTHER PUBLICATIONS

CRF Sequence Defective 5222008. May 22, 2008.*

Ellsworth et al., c-Jun N-terminal kinase activation of activator protein-1 unerlies homologous regulation of the gonadotropin-releasing hormone receptor gene in alphaT#-1 cells, Endocrinol. 144(3):839-849, 2003.*
Wang et al., Three distinct types of GnRH receptor characterized in bullfrog, Proc. Natl. Acad. Sci. USA, 98(1):361-366, Jan. 2, 2001.*
Mamputha et al., Conserved amino acid residues that are important for ligand binding in the type I gonadotropin-releasing hormone (GnRH) receptor are requried for high potentcy of the GnRH II at the Type II GnRH receptor, Mol. Endocrinol. 21(1):281-291, 2007.*
Bardsley et al., Massive lymphocytic inflitration of uterine leimyomas associated with GnRH agonist treatment, Histopathology, 33:80-82, 1998.*
Batticane et al., Luteinizing hormone-releasing hormone signaling at the lymphocyte involves stimulation of interleukin-2 receptor expression, Endocrinology, 129(1):277-286, 1991.*
Whiteside, T.L., "Down-regulation of zeta-chain expression in T cells: a biomarker of prognosis I cancer?", Cancer Immunol Immunother., 53:865-878 (2004).
Zea, A. H. et al., "Alterations in T Cell Receptor and Signal Transduction Molecules in Melanoma Patients", Clinical Cancer Research, 1:1327-1335 (1995).
La, P. et al., "Alterations in Expression and Functon of Signal-Transducng Proteins in Tumor-Associated T and Natural Killer Cells in Patients with Ovarian Cancer", Clin. Cancer Res., 2:161-173 (1996).
Kuss, I et al., "Expression of zeta in T cells Prior to Interleukin-2 Therapy as a Predictor of Response and Survival in Patients with Ovarian Carcinoma", Cancer Biother Radiopharm, 17:631-640 (2002).
Healy, C. G. et al., "Impaired Expression and Function of Signal-Transducing zeta chains in Peripheral T cells and Natural Killer Cells in Patients with Prostate Cancer", Cytometry, 32:109-19 (1998).
Nakagomi, H. et al., "Decreased Expression of the Signal-Transducing zeta chains in Tumor-Infiltrating T-cells and NK cells of Patients with Colorectal Cancer", Cancer Res., 53:5610-5612 (1993).
Matsuda, M. et al., "Alteration in the Signal-Transducing Molecules of T cells and NK cells in Colorectal Tumor-Infiltrating, Gut Mucosal and Peripheral Lymphocytes: Correlation with the stage of the Disease", Int. J. Cancer, 61:765-772 (1995).
Reichert, T. E. et al., „Absent or Low Expression of the ζ Chain in T cells at the Tumor Site Correlates with Poor Survival in Patients with Oral Carcinoma, Cancer Research, 58:5344-5347 (1998).
Finke, J. H. et al., „Loss of T-cell Receptor zeta chain and p56ck in T-cells Infiltrating Human Renal Cell Carcinoma, Cancer Res., 53:5613-5616 (1993).
Kuss, I. et al., "Clinical Significance of Decreased ζ Chain Expression Blood Lymphocytes of Patients with Head and Neck Cancer", Clinical Cancer Research, 5:329-334 (1999).
Maki, A. et al., "Decreased CD3 zeta Molecules of T Lymphocytes from Patients with Hepatocellular Carcinoma, Associated with Hepatitis C Virus", Hepatol. Res., 27:272-278 (2003).

(Continued)

*Primary Examiner* — Lorraine Spector
*Assistant Examiner* — Claire Kaufman
(74) *Attorney, Agent, or Firm* — Browdy and Neimark, PLLC

(57) ABSTRACT

Methods and compositions comprising GnRH-I and GnRH-II, GnRH-I and GnRH-II antibodies, anti-receptor antibodies, polynucleotide constructs and GnRH-I and GnRH-II analogs for immune enhancement and suppression, prevention and treatment of diseases and conditions characterized by abnormal T-cell activity, treatment of viral and prion-related diseases, and treatment of T-cell related neoplastic diseases are disclosed.

28 Claims, 17 Drawing Sheets

OTHER PUBLICATIONS

Štefanová, I. et al., "HIV Infection-induced Posttranslational Modification of T Cell Signaling Molecules Associated with Disease Progression", The Journal of Clinical Investigation, 98:1290-1297 (1996).

Liossis, S.C. et al., "Altered Pattern of TCR/CD3-mediated Protein-tyrosyl Phosphorylaton in T Cells fom Pateints with Systemic Lupus Erythematosus", The Journal of Clinical Investigation, 101:1448-1457 (1998).

Zea, A. H. et al., "Changes in Expression of Signaling Transduction Proteins in T Lymphocytes of Patients with Leprosy", Infection and Immunity, 66:499-504 (1998).

Gabison, E E. et al., "EMMPRIN/CD147, an MMP Modulator in Cancer Development and Tissue Repair", Biochimie., 87:361-368 (2005).

June, "Principles of Adoptive T Cell Cancer Therapy," J. Clin. Inv. 117:1204-1212 (2007).

June, "Adoptive T Cell Therapy for Cancer in the Clinic," J. Clin. Inv. 117:1466-1476 (2007).

Millar et al., "Chimeric Analogues of Vertebrate Gonadotropin-Releasing Hormones Comprising Substitutions of the Variant Amino Acids in Positions 5, 7, and 8: Characterization of Requirements for Receptor Binding and Gonadotropin Release in Mammalian and Avian Pituitary Gonadotropes", J. Biol. Chem., 264:21007-21013 (1989).

Hsu et al., "Immunomodulation in women with endometriosis receiving GnRH agonist" Obstet Gynecol 89:993-8 (1997) Abstract Only.

Klijn et al., "Combined Tamoxifen and Luteinizing Hormone-Releasing Hormone (LHRH) Agonist Versus LHRH Agonist Alone in Premenopausal Advanced Breast Cancer: A Meta-Analysis of Four Randomized Trials," J. Clin Oncol. 19:343-353 (2001).

Mann et al. "Effect of Neonatal Treatment with GnRH Antagonist on Development of the Cell-Mediated Immune Response in Marmosets", American Journal of Reprod. Immunolog., 42: 175-186, 1999.

Chen et al. "The Neuropeptides GnRH-II and GnRH-I are Produced by Human T Cells and Trigger Laminin Receptor Gene Expression, Adhesion, Chemotaxis, and Homing to Specific Organs", Nature Medicine, 8(12): 1421-1426, 2002.

Rahimipour et al. "Design, Synthesis, and Evaluation of a Long-Acting, Potent Analogue of Gonadotropin-Releasing Hormone", Journal of Medical Chemistry, 44(22): 3645-3652, 2001.

Rieger et al. "Role of the 37 kDa Laminin Receptor Precursor in the Life Cycle of Prions", Transfus. Clin. Biol., 6: 7-16, 1999.

Schori et al. "T-Cell-Based Immunity Counteracts the Potential Toxicity of Glutamate in the Central Nervous System", Journal of Neuroimmunology, 119: 199-204, 2001.

Schwartz et al. "Protective Autoimmunity: Regulation and Prospects for Vaccination After Brain and Spinal Cord Injuries", Trends in Molecular Medicine, 7(6): 252-258, 2001.

Sealfon et al. "Molecular Mechanism of Ligand Interaction With the Gonadotropin-Releasing Hormone Receptor", Endocrine Reviews, 18(2): 180-205, 1997.

Silverman et al. "Mast Cells With Gonadotropin-Releasing Hormone-Like Immunoreactivity in the Brain of Doves", Proc. Natl. Acad. Sci. USA, 91: 3695-3699, 1994.

Spangelo et al. "The Role of Immunopeptides in the Regulation of Anterior Pituitary Hormone Release", TEM, p. 408-412, 1990.

Standaert et al. "Presence of Luteinizing Hormone-Releasing Hormone Binding Sites in Cultured Porcine Lymphocytes", Biology of Reproduction, 46: 997-1000, 1992.

Goldsteyn et al. "The Role of the Thymus-Hypothalamus-Pituitary-Gonadal Axis in Normal Immune Processes and Autoimmunity", Journal of Rheumatology, 14(5): 982-990, 1987. Abstract.

Urbanski et al. "Regional Expression of mRNA Encoding A Second Form of Gonadotropin-Releasing Hormone in the Macaque Brain", Endocrinology, 140(4): 1945-1948, 1999.

Wang et al. "High-Affinity Laminin Receptor is a Receptor for Sindbis Virus in Mammalian Cells", Journal of Virology, 66(8): 4992-5001, 1992.

Yin et al. "Expression of the Messenger RNA for Gonadotropin-Releasing Hormone and Its Receptor in Human Cancer Cell Lines", Life Sciences, 62(22): 2015-2023, 1998.

White et al. "Second Gene for Gonadotropin-Releasing Hormone in Humans", Proc. Natl. Acad. Sci. USA, 95: 305-309, 1998. p. 305-306.

Chen et al. "Human Peripheral Blood Mononuclear Cells Express Gonadotropin-Releasing Hormone (GnRH), GnRH Receptor, and Interleukin-2 Receptor γ-Chain Messenger Ribonucleic Acids That Are Regulated by GnRH In Vitro", Journal of Clinical Endocrinology and Metabolism, 84(2): 743-750, 1999.

Azad et al. "Immunoactivation Enhances the Concentration of Luteinizing Hormone-Releasing Hormone Peptide and Its Gene Expression in Human Peripheral T-Lymphocytes", Endocrinology, 133(1): 215-223, 1993.

Batticane et al. "Luteinizing Hormone-Releasing Hormone Signaling at the Lymphocyte Involves Stimulation of Interleukin-2 Receptor Expression", Endocrinology, 129(1): 277-287, 1991. Abstract.

Ben-Yehudah et al. "I.V. Administration of L-GNRH-PE66 Efficiently Inhibits Growth of Colon Adenocarcinoma Xenografts in Nude Mice", Int. J. Cancer, 92: 263-268, 2001.

Canfield et al. "The Nonintegrin Laminin Binding Protein (P67 LBP) is Expressed on a Subset of Activated Human T Lymphocytes and, Together With the Integrin Very Late Activation Antigen-6, Mediates Avid Cellular Adherence to Laminin", The Journal of Immunology, 163: 3430-3440, 1999.

Chen et al. "Transcriptional Regulation of the Human GnRH II Gene is Mediated by a Putative cAMP Response Element", Endocrinology, 142(8): 3483-3492, 2001.

Chen et al. "A Second Isoform of Gonatropin-Releasing Hormone is Present in the Brain of Human and Rodents", FEBS Letters, 435: 199-203, 1998.

Chen et al. "Two Isoforms of Gonadotropin-Releasing Hormone Are Coexpressed in Neuronal Cell Lines", Endocrinology, 142(2): 830-837, 2001.

Chen et al. "Two Forms of Gonadotropin-Releasing Hormone (GnRH) are Expressed in Human Breast Tissue and Overexpressed in Breast Cancer: A Putative Mechanism for the Antiproliferative Effect of GnRH by Down-Regulation of Acidic Ribosomal Phosphoproteins P1 and P2", Cancer Research, 62: 1036-1044, 2002.

Delgado et al. "Cutting Edge: Is Vasoactive Intestinal Peptide A Type 2 Cytokine?", The Journal of Immunology, 166: 2907-2912, 2001.

Downing et al. "Neural Immunoregulation: Emerging Roles for Nerves in Immune Homeostasis and Disease", Immunology Today, 21(6): 281-289, 2000.

Gestrin et al. "Second Form of Gonadotropin-Releasing Hormone in Mouse: Immunocytochemistry Reveals Hippocampal and Periventricular Distribution", FEBS Letters, 448: 289-291, 1999.

Gould et al. "Effect of Neonatal Treatment With A Gonadotropin Releasing Hormone Antagonist on Developmental Chenges in Circulating Lymphocyte Subsets: A Longitudinal Study in Male Rhesus Monkeys", Developmental and Comparative Immunology, 22(4): 457-467, 1998.

Grakoui et al. "The Immunological Synapse: A Molecular Machine Controlling T Cell Activation", Science, 285: 221-224, 1999.

Hayflick et al. "The Complete Nucleotide Sequence of the Human Gonadotropin-Releasing Hormone Gene", Nucleic Acids Research, 17(15): 6403-6404, 1989.

Jacobson et al. "Cyclical Expression of GnRH and GnRH Receptor mRNA in Lymphoid Organs", Neuroendocrinology, 67: 117-125, 1998.

Jacobson et al. "Modulation of the Expression of Murine Lupus by Gonadotropin-Releasing Hormone Analogs", Endocrinology, 134(6): 2516-2523, 1994.

Jacobson "Gonadotropin-Releasing Hormone: Potential Role in Autoimmunity", International Immunopharmacology, 1: 1077-1083, 2001.

Johnston et al. "Human T Lymphocyte Chemotaxis and Adhesion Induced by Vasoactive Intestinal Peptide", The Journal of Immunology, 153: 1762-1768, 1994.

Koch et al. "Production and Characterization of an Antiserum to Synthetic Gonadotropin-Releasing Hormone", Biochemical and Biophysical Research Communication, 55(3): 616-622, 1973.

Lescheid et al. "A Second Form of Gonadotropin-Releasing Hormone (GnRH) With Characteristics of Chicken GnRH-II is Present in the Primate Brain", Endocrinology, 138(12): 5618-5629, 1997.

Levite et al. "Extracellular K+ and Opening of Voltage-Gated Potassium Channels Activate T Cell Integrin Function: Physical and Functional Association Between Kv1.3 Channels and β1 Integrins", Journal of Experimental Medicine, 191(7): 1167-1176, 2000.

Levite et al. "Nerve-Driven Immunity: Neuropeptides Regulate Cytokine Secretion of T Cells and Intestinal Epithelial Cells in A Direct, Powerful and Contextual Manner", Annals of Oncology, 12(Suppl.2): S19-S25, 2001.

Levite "Nervous Immunity: Neurotransmitters, Extracellular K+ and T-Cell Function", Trends in Immunology, 22(1): 2-5, 2001.

Levite "Neuropeptides, by Direct Interaction With T Cells, Induce Cytokine Secretion and Break the Commitment to A Distinct T Helper Phenotype", Proc. Natl. Acad. Sci. USA, 95: 12544-12549, 1998.

Levite et al. "Neuropeptides, Via Specific Receptors, Regulate T Cell Adhesion to Fibronectin", The Journal of Immunology, 160: 993-1000, 1998.

Maier et al. "Thermocytes Express A mRNA That is Identical to Hypothalamic Luteinizing Hormone-Releasing Hormone mRNA", Cellular and Molecular Neurobiology, 12(5): 447-454, 1992.

Mann et al. "Neonatal Treatment With Luteinizing Hormone-Relaesing Hormone Analogs Alters Peripheral Lymphocyte Subsets and Cellular and Humorally Mediated Immune Responses in Juvenile and Adult Male Monkeys", Journal of Clinical Endocrinology and Metabolism, 78(2): 292-298, 1994.

Mann et al. "Endocrine-Immune Interaction: Alterations in Immune Function Resulting From Neonatal Treatment With a GnRH Antagonist and Seasonality in Male Primates", American Journal of Reproductive Immunology, 44: 30-40, 2000.

Marchetti et al. "Luteinizing Hormone-Releasing Hormone (LHRH) Agonist Restoration of Age-Associated Decline of Thymus Weight, Thymic LHRH Receptors, and Thymocyte Proliferative Capacity", Endocrinology, 125(2): 1037-1045, 1989.

Marchetti et al. "Luteinizing Hormone-Releasing Hormone (LHRH) Receptors in the Neuroendocrine-Immune Network. Biochemical Bases and Implications for Reproductive Physiopathology", Ann. NY Acad. Sci., 784: 209-236, 1996. Abstract.

Millar et al. "A Novel Mammalian Receptor for the Evolutionarily Conserved Type II GnRH", Proc. Natl. Acad. Sci. USA, 98(17): 9636-9641, 2001.

Miyamoto et al. "Identification of the Second Gonadotropin-Releasing Hormone in Chicken Hypothalamus: Evidence That Gonatropin Secretion Is Probably Controlled by Two Distinct Gonadotropin-Releasing Hormones in Avian Species", Proc. Natl. Acad. Sci. USA, 81: 3874-38, 1984.

Mohagheghpour et al. "Signal Requirements for Production of Luteinizing Hormone Releasing-Hormone by Human T Cells", Cellular Immunology, 163: 280-288, 1995.

Neill et al. "A Gonadotropin-Releasing Hormone (GnRH) Receptor Specific for GnRH II in Primates", Biochemical and Biophysical Research Communications, 282(4): 1012-1018, 2001.

Neill "Minireview: GnRH and GnRH Receptor Genes in the Human Genome", Endocrinology, 143(3): 737-743, 2002.

Palmon et al. "The Gene for the Neuropeptide Gonadotropin-Releasing Hormone is Expressed in the Mammary Gland of Lactating Rats", Proc. Natl. Acad. Sci. USA, 91: 4994-4996, 1994.

Pfleger et al. "Conformational Constraint of Mammalian, Chicken, and Salmon GnRHs, But Not GnRH II, Enhances Binding at Mammalian and Nonmammalian Receptors: Evidence for Preconfiguration of GnRH II", Molecular Endocrinology, 16(9): 2155-2162, 2002.

* cited by examiner

Staining of the 67 kDa laminin receptor (FITC)

| Cells/Treatment | Double immunofluorescence staining for the 67-kDa laminin receptor and the TCR | |
|---|---|---|
| | % Double positive cells | % Upregulation |
| Untreated resting T-cells | 32 | |
| Resting T-cells treated with | | |
| GnRH-I | 42 | 31 % |
| GnRH-II | 45 | 41 % |
| GnRH-I receptor antagonist | 32 | 0 % |
| GnRH-I+GnRH-I receptor antagonist | 33 | 3 % |
| GnRH-II+GnRH-I receptor antagonist | 50 | 56 % |
| TCR-activating mAb's | 65 | 103 % |

GnRH-I (SEQ ID No: 2)

1134
AGTACTCAACCTACTTCAAGGGAAGATTGGGATCTTTTT
  1192 2063
GGCTCTCTGCCTCTAAACAGAATGAAGCCAATTCAAAAA

CTCCTAGCTGGCCTTATTCTACTGACTTGGTGCGTGGAA

GGCTGCTCCAGCCAGCACTGGTCCTATGGACTGCGCCT

GGAGGAAAGAGAGATGCCGAAATTTGATTGATTCTTTC
  2204 3720
CAAGAGATAGTCAAAGAGGTTGGTCAACTGGCAGAAACC
                                3766
CAACGCTTTGAATG

Fig. 6c

GnRH-II (SEQ ID No: 3)

1312
CTGCAGCTGCCTGAAGGAGCCATCTCATCCACAGCTCTT
    1355 2098
CCTTGAGCAGCCATGGCCAGCTCCAGGCGAGGCCTCCTG

TCCTGCTGCTGCTGACTGCCCACCTTGGACCCTCAGAG

GCTCAGCACTGGTCCCATGGCTGGTACCCTGGAGGAAAG

CGAGCCCTCAGCTCAGCCCAGGATCCCCAGAATGCCCTT
    2250
AG

Fig. 6d

```
                            SEQUENCE LISTING

<160> NUMBER OF SEQ ID NOS: 49

<210> SEQ ID NO 1
<211> LENGTH: 5
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: Blockers of laminin binding, synthetic peptide

<400> SEQUENCE: 1

Tyr Ile Gly Ser Arg
1               5

<210> SEQ ID NO 2
<211> LENGTH: 249
<212> TYPE: DNA
<213> ORGANISM: Homo sapiens

<400> SEQUENCE: 2
agtactcaac tcatcctaag ggaagattgg ggatcttttt ggctctctgc ctctaaacag      60
aatgaagcca attcaaaaac tcctagctgg ccttattcta ctgacttggt gcgtggaagg     120
ctgctccagc cagcactggt cctatggact gcgccctgga ggaaagagag atgccgaaaa     180
tttgattgat tctttccaag agatagtcaa agaggttggt caactggcag aaacccaacg     240
ctttgaatg                                                             249

<210> SEQ ID NO 3
<211> LENGTH: 197
<212> TYPE: DNA
<213> ORGANISM: Homo sapiens

<400> SEQUENCE: 3
ctgcagctgc ctgaaggagc catctcatcc acagctcttc cttgagcagc catggccagc      60
tccaggcgag gcctcctgct cctgctgctg ctgactgccc accttggacc ctcagaggct     120
cagcactggt cccatggctg gtaccctgga ggaaagcgag ccctcagctc agcccaggat     180
ccccagaatg cccttag                                                    197

<210> SEQ ID NO 4
<211> LENGTH: 10
<212> TYPE: PRT
<213> ORGANISM: Mus musculus

<400> SEQUENCE: 4

Glu His Trp Ser Tyr Gly Leu Arg Pro Gly
1               5                  10

<210> SEQ ID NO 5
<211> LENGTH: 10
<212> TYPE: PRT
<213> ORGANISM: Cavia porcellus

<400> SEQUENCE: 5

Glu Tyr Trp Ser Tyr Gly Val Arg Pro Gly
1               5                  10
```

```
<210> SEQ ID NO 6
<211> LENGTH: 10
<212> TYPE: PRT
<213> ORGANISM: Sparus aurata

<400> SEQUENCE: 6

Glu His Trp Ser Tyr Gly Leu Ser Pro Gly
1               5                   10

<210> SEQ ID NO 7
<211> LENGTH: 10
<212> TYPE: PRT
<213> ORGANISM: Menidia menidia

<400> SEQUENCE: 7

Glu His Trp Ser Phe Gly Leu Ser Pro Gly
1               5                   10

<210> SEQ ID NO 8
<211> LENGTH: 10
<212> TYPE: PRT
<213> ORGANISM: Clupea pallasi

<400> SEQUENCE: 8

Glu His Trp Ser His Gly Leu Ser Pro Gly
1               5                   10

<210> SEQ ID NO 9
<211> LENGTH: 10
<212> TYPE: PRT
<213> ORGANISM: Clarias gariepinus

<400> SEQUENCE: 9

Glu His Trp Ser His Gly Leu Asn Pro Gly
1               5                   10

<210> SEQ ID NO 10
<211> LENGTH: 10
<212> TYPE: PRT
<213> ORGANISM: Gallus gallus

<400> SEQUENCE: 10

Glu His Trp Ser Tyr Gly Leu Gln Pro Gly
1               5                   10

<210> SEQ ID NO 11
<211> LENGTH: 10
<212> TYPE: PRT
<213> ORGANISM: Oncorhynchus sp.

<400> SEQUENCE: 11

Glu His Trp Ser Tyr Gly Trp Leu Pro Gly
1               5                   10

<210> SEQ ID NO 12
<211> LENGTH: 10
<212> TYPE: PRT
<213> ORGANISM: Gallus gallus

<400> SEQUENCE: 12

Glu His Trp Ser His Gly Trp Tyr Pro Gly
1               5                   10

<210> SEQ ID NO 13
```

```
<211> LENGTH: 10
<212> TYPE: PRT
<213> ORGANISM: Squalus acanthias

<400> SEQUENCE: 13

Glu His Trp Ser His Gly Trp Leu Pro Gly
1               5                   10

<210> SEQ ID NO 14
<211> LENGTH: 10
<212> TYPE: PRT
<213> ORGANISM: Petromyzon marinus

<400> SEQUENCE: 14

Glu His Trp Ser His Asp Tyr Lys Pro Gly
1               5                   10

<210> SEQ ID NO 15
<211> LENGTH: 10
<212> TYPE: PRT
<213> ORGANISM: Petromyzon marinus

<400> SEQUENCE: 15

Glu His Tyr Ser Leu Glu Trp Lys Pro Gly
1               5                   10

<210> SEQ ID NO 16
<211> LENGTH: 10
<212> TYPE: PRT
<213> ORGANISM: Ascidia ceratodes

<400> SEQUENCE: 16

Glu His Trp Ser Asp Tyr Phe Lys Pro Gly
1               5                   10

<210> SEQ ID NO 17
<211> LENGTH: 10
<212> TYPE: PRT
<213> ORGANISM: Ascidia ceratodes

<400> SEQUENCE: 17

Glu His Trp Ser Leu Cys His Ala Pro Gly
1               5                   10

<210> SEQ ID NO 18
<211> LENGTH: 10
<212> TYPE: PRT
<213> ORGANISM: Clupea pallasi

<400> SEQUENCE: 18

Gln His Trp Ser His Gly Leu Ser Pro Gly
1               5                   10

<210> SEQ ID NO 19
<211> LENGTH: 6
<212> TYPE: PRT
<213> ORGANISM: Petromyzon marinus

<400> SEQUENCE: 19

Arg His Leu Met Gly Ser
1               5

<210> SEQ ID NO 20
<211> LENGTH: 10
<212> TYPE: PRT
<213> ORGANISM: Squalus acanthias
```

```
<400> SEQUENCE: 20

Gln His Trp Ser His Gly Trp Tyr Pro Gly
1               5                   10

<210> SEQ ID NO 21
<211> LENGTH: 10
<212> TYPE: PRT
<213> ORGANISM: Squalus acanthias

<400> SEQUENCE: 21

Gln His Trp Ser His Gly Trp Leu Pro Gly
1               5                   10

<210> SEQ ID NO 22
<211> LENGTH: 10
<212> TYPE: PRT
<213> ORGANISM: Chelyosoma productum

<400> SEQUENCE: 22

Gln His Trp Ser Asp Tyr Phe Lys Pro Gly
1               5                   10

<210> SEQ ID NO 23
<211> LENGTH: 10
<212> TYPE: PRT
<213> ORGANISM: Petromyzon marinus

<400> SEQUENCE: 23

Gln His Trp Ser His Asp Trp Lys Pro Gly
1               5                   10

<210> SEQ ID NO 24
<211> LENGTH: 10
<212> TYPE: PRT
<213> ORGANISM: Petromyzon marinus

<400> SEQUENCE: 24

Gln His Tyr Ser Leu Glu Trp Lys Pro Gly
1               5                   10

<210> SEQ ID NO 25
<211> LENGTH: 10
<212> TYPE: PRT
<213> ORGANISM: Squalus acanthias

<400> SEQUENCE: 25

Gln His Trp Ser His Gly Trp Leu Pro Gly
1               5                   10

<210> SEQ ID NO 26
<211> LENGTH: 10
<212> TYPE: PRT
<213> ORGANISM: Acipenser gueldenstaedtii

<400> SEQUENCE: 26

Glu His Trp Ser Tyr Gly Leu Arg Pro Gly
1               5                   10

<210> SEQ ID NO 27
<211> LENGTH: 10
<212> TYPE: PRT
<213> ORGANISM: Clarias gariepinus

<400> SEQUENCE: 27
```

-continued

```
Glu His Trp Ser His Gly Trp Tyr Pro Gly
1               5                   10

<210> SEQ ID NO 28
<211> LENGTH: 10
<212> TYPE: PRT
<213> ORGANISM: Clupea pallasi

<400> SEQUENCE: 28

Gln His Trp Ser Tyr Gly Trp Leu Pro Gly
1               5                   10

<210> SEQ ID NO 29
<211> LENGTH: 10
<212> TYPE: PRT
<213> ORGANISM: Clupea pallasi

<400> SEQUENCE: 29

Gln His Trp Ser His Gly Trp Tyr Pro Gly
1               5                   10

<210> SEQ ID NO 30
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 30

Glu His Xaa Ser Xaa Xaa Leu Xaa Pro
1               5

<210> SEQ ID NO 31
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 31

Glu His Trp Ser Xaa Xaa Leu Xaa Gly Xaa
1               5                   10

<210> SEQ ID NO 32
<211> LENGTH: 14
<212> TYPE: RNA
<213> ORGANISM: Artificial
```

```
<220> FEATURE:
<223> OTHER INFORMATION: Synthetic
<220> FEATURE:
<221> NAME/KEY: misc_feature
<223> OTHER INFORMATION: The sequence requirement for the hairpin
      ribozyme.
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (9)..(14)
<223> OTHER INFORMATION: n is a, c, g, or u

<400> SEQUENCE: 32
nnnbngucnn nnnn                                                    14

<210> SEQ ID NO 33
<211> LENGTH: 7224
<212> TYPE: DNA
<213> ORGANISM: Homo sapiens

<400> SEQUENCE: 33 aagcttttg  ctttctattc  attcattcgt  tcattcattc  attcaaacct  atacttaccg    60
aatgctcact  aaatgccggg  ggtttattaa  gagagattta  aataagatgg  gatctttgac   120
tattacaggt  ttcagcctag  gggtaaatta  ggggaagaca  accatgtatt  caaataaatg   180
taattaagag  taatggttgt  gtgtgtattt  tacatgcttg  tcctgtgtaa  ataacacgtc   240
cacggttgca  cctctggggt  ggaacatcta  aaaatttag  ataatgatac  ccactttgca   300
tggctattgt  aatgagtgct  cttatacatt  tgctatttat  taaataacta  taatttctca   360
tctttctgtt  cccactgccc  ttaagagtga  tttgcatatt  taactcaata  agcatctact   420
gaaatgagtt  gatctgttga  tgtaagtctg  ctcaatatgg  tcttgctctc  agaatatgtt   480
tcttgccttt  ttgatgcttt  agaaggcttt  caaggtaagt  caagcaggga  acctggtggg   540
gtagatgagg  gaattttcaa  acacacaact  gtctgattta  ggatcctaca  tggacttggt   600
atatagtgtc  acttacttgt  aaatcagatt  ttaaaattg  gaagcaactc  tgtgatcatc   660
tagtccatct  agtctacacc  cttcctttta  caaatgaaga  atccaagagc  cagaagctcc   720
cagacatcct  gactcaatgt  cctatatttg  ttgtatagcc  tcctttgtgg  aagttatgta   780
tgcatttgac  ttcacttaat  ctaagacatc  tattttcctt  gaactcttga  taggtctgct   840
ggtttcctca  agggaatcca  atctagctgg  attttaatct  ctttgaattg  tgtcctcagc   900
tataaaagtt  ttagctgagg  ttttaatggc  tgcacttaag  taaatctaac  agatatacca   960
gggggtgttc  caattacata  caccattaaa  gggctttatg  tgaggatttt  taaaaattac  1020
cattaaaaaa  aaaaagcat  agtccatttg  cagtataatt  taccagcagg  aaagatttca  1080
atgtcctgga  aaaattccct  ataaaaagga  agataggaaa  acagaaaagt  cacagtactc  1140
aacctacttc  aagggaagat  tgggatcttt  ttggctctct  gcctctaaac  aggtaaaagg  1200
ctttgtatta  tttctagcac  gagttttct  tctttagatt  gcatgctatt  gtatgtctac  1260
agggcatttg  acagcccaag  ggctaaatcc  aggtgtgacg  gtatctaatg  atgtcctgtc  1320
cttcactgtc  cttgccatca  ccagccacag  agatccaggc  tttggggact  cccacagctt  1380
atcgaccagt  gtttgattta  gttttagcc  tctttcccat  caaatgaaaa  ttaacttgga  1440
gacacatttc  attagaaat  tagaggcccc  cttggctagg  aaggcatctg  gtctgggact  1500
```

```
aactactttg aacagtgttg agtcctctct cccacagatg gttcagccag cagtaatgct   1560
aggcaagact gaaggataaa tagaaaaatg tcattagtac catggggtag ccatgtaatg   1620
tcaagcaatt ttatattagc cagagattcc tagtaggagc tacttttctt aacagatgac   1680
tcagttctct ctatctcagg aatgaaagag ttgaagacca atccacaaca ggggaaatgt   1740
taaggcaaaa tgatgaactt gataagggat gaattatggg gtttggataa ccaaacaata   1800
aaaataaaag tatagactat tttagtacta aaaaggtcct gaacatgtga gcttaagtac   1860
tcattttgtc cccagtggct aagaaactaa aggcaagcca gcaagtgtct ctgagtttca   1920
gtgtctgtat gtaaaaactg actctgactt ccatcttctg cagggttagt gatacagatg   1980
ctagcttttt cactaaagag gtcttttagt ttatactcaa ccttgtctgg atctaatttg   2040
attgtgcatt catgtgcctt agaatgaagc caattcaaaa actcctagct ggccttattc   2100
tactgacttg gtgcgtggaa ggctgctcca gccagcactg gtcctatgga ctgcgccctg   2160
gaggaaagag agatgccgaa aatttgattg attctttcca agaggtaagt ttctctcagc   2220
ttcaaaataa gacatagtga tttgattcaa tttaactata ttaaacattc aggatagccc   2280
caatgtcaat attctatgat gttgtaccct agatgctcca ggtgagataa ggcacttaca   2340
aagtagaagt cccattccta ctttcagttc acacagggac taaacaaaga gctggaaaaa   2400
ttccaaaaga atatattaat agcaacaagt gtgagacagc acgtcatact ctgagtgtat   2460
gggattgcta aaggaattag aaacaatggg ataggtcaa ggtctgtatc agaagatgat   2520
tctttgggat ttggaaaaaa cgttagaact tcgtattttt tttcctcatt tcatctttta   2580
aacatatcta tgctattaga tcagtacatt tttataattt ataaatgagt atccttatca   2640
aggatgcaat gccctataat ttcttttcac tgataggggc atttaagcaa agttggagac   2700
tggtagaata caggaattag caaactcaag atgataagat aacgtagtag aaaacatgct   2760
gatttaaatt catatagatt agattatagg actggcacca aacctaacgt gaggtacttg   2820 cttcttgtt ttttggggtt attttctaag acagggtctc gctgtgttat ctaggctgga   2880
atttagtggc acgatcacag ctcactgcag cttgacttct tgggctcaag tgatcctccc   2940
acctcagccg tctgcatagc tgggaccaca ggcatgcact atcacaccca actaattttt   3000
aaaacttttt atagagatgg ggtttcccta tgttgcccag gctggtctca aactcctggg   3060
ctcaagggat cctcccacct tggcctccca aagtgccggg attttttgt ttataaaata   3120 tgaccactca tcagggtcat gtaaggaaag aagccatcta tgttagctga ttaacctgaa   3180
aaataaccta ggactgagaa tgggaaaaat tttaaatcat ttcattatca ttggaaggaa   3240
ttatctcttt tctgagaaat aataaagata atttagtatt aaagaagacc cagaatctga   3300
agcctcttct ctgcaggtta tacatgaagc aaatctcatt gaactataac atatttagta   3360
aaacctagaa aataaaaacc aaccttttt acaactataa actcttgggg ttttttgctt   3420 tttgttttt tgggtatact gactctcatg aggctcaaag tgcctccctc ttttcatctt   3480 taagggaaa atatgatact tcttactgtc tccattatct ccagatcccc atgccattca   3540
gtagaaatgt cagatggcag atctgtgtcc ttaaagtccc tatgctaatc ctgcaacttt   3600
cccaatctcc ccagccccac atccccttga ccccactctc cacaattttt tggtggaaat   3660
ggaaaacacc atttcatttc tttatctcca tctcaaagca tcacattctc tttcttcaga   3720
tagtcaaaga ggttggtcaa ctggcagaaa cccaacgctt tgaatgcacc acgcaccagc   3780
cacgttctcc cctccgagac ctgaaaggag ctctggtaag ttaaagtgat cataacatga   3840
tcacagcata gagctctaga ggtggataag cctttgggga tcacttagga cagctacctc   3900
```

```
ccagatactg tggggcttac attcctgact cctctgttac ctcctgtggt aggaccgtgt   3960
ttcatgacaa tcccagttgg tggttagaca gcactagggg ctgaaacgtt tttttgtttg   4020
tttgttttt  ctgaagttga attgaaatct ctctgtaact tttatctctt aatcctggtt   4080
ctagcttttg ggataactaa caaaacaaat tcttcccac  tgctgcattt catttcttca   4140
agtaaaatca ccaaaccccc tagactactc cactccaggc tactccacag ccctccacct   4200
gatcctgcaa ctgtgcttta tcttacatgg ttttccagaa ccttggggaa tagagacatg   4260
agaaacactg ctgtagatgg gtttttttt  ctcttctttg aatgaaaaa  tgccaaacta   4320
ctaaatttat aatttagaga gtgatggact tgatttccag tttcctgata ggacaataat   4380
cacctccaaa ttccaccccc caaaatggaa atacactaat catattaggt ttttgatgaa   4440
aaagtataaa gagaattgaa tgtataaatt gaatctttta aaaaaattat tgttgagac   4500
aggatcttgc tctgttcccc gggctagagt gcaatggtgc aatcaatgct caccacagcc   4560
tcaacctccc aggctcaagc aattctggag actagattag cctctctagt agctgggact   4620
ataagcactt gccaccacac ccagctgatt ttattttta  attttttgtt agagacaggg   4680
tctatgttgc ccaggctggt ctcaaactcc cagcctcaag atccacccaa agtgctggga   4740
ttaaaggtgc aagccactgt gcctgactta agttgaatct tggattcaat gttgatattc   4800
tctgatctct attgtccact tatctgcagc aatcagaagg cattacagtt aatgatcagt   4860
tatgcctagg agctgggaaa gcccaaataa atcatatata aaaataagct gtaattttaa   4920
ttgtctacag tgacttcaac ttaatatacc cacagaacaa agaaaaagt  gggcagacgt   4980
cgttatttcc ttttttgttt tttttttgag acggagtctc gctctgttgc caggctggag   5040
tgcagtggcg caatctcggc tcaatgcaac ctccatctcc tgggttcaag cgattctcct   5100
gactcagcct cccgagtagc tgagattaca ggcatgagcc accacactga ctaattttg    5160
tattttagt  agagatgggg tttcaccatg ttggccagga tggtctcaat cccttaacct   5220
tgtgatccgc ccactggcct cccaaagtgc tgggattaca ggcatgaggc caccacgccc   5280
gagcctattt cctttctttt tctaatcttg cttactgcat tacaaaaatg caagcagtg    5340
aaatttgtca acatgacat  tatgaagaaa ttgaagcaaa ggctggttta atagcaaagt   5400
aattgaccag acttttttt  cacttccttc ctcacaactc atccttaaac tattaatgta   5460
gattttatgt atattaagtg cttaaaaaga cccaatcggc caggcacagt ggctcatgct   5520
gtaatcctag cattttggga agccgaggta agtggatcac ttgaggccag agttcaaga    5580
ccagcctggc caacatggtg acaccctgtc tctactaaaa ctataaaaat tagccagaag   5640
tgcggtgatg catgcctgca atcccaacta ctagagaggc tgaggcacga gaatcatttg   5700
aacctggaag gtggaggttg ccatgagctg agatcatact actgcactcc agcctgggtg   5760
acagagtgag gttctgtctc aaaaaaaaaa aaaaccagaa aaacaaaccc aatttatcat   5820
gtctccctag cactaactag agcacaaaat caaacagacc aattccttcc agactgatat   5880
tttagaaatt aaaatgtcaa aatgtaatga aattcagctg gtaaagtcag tcttgatata   5940
tttgttatat attttcagg  aaagtctgat tgaagaggaa actgggcaga agaagattta   6000
aatccattgg gccagaagga atgaccatta ctaacatgac ttaagtataa ttctgacatt   6060
gaaaatttat aacccattaa atacctgtaa atggtatgaa tttcagaaat ccttacacca   6120
agttgcacat attccataat aaagtgctgt gttgtgaatg aagtggcata cctgttaaat   6180
cttttctcca actcagaactc cggggaagg  atcactgaa  acccaccaaa gggagccctc   6240
catgtgtgta tacaggtggc agatgggagg gcaggtaaga taaagtgtct gttgttgaca   6300
```

| | |
|---|---|
| aaagggatct caggctctcc agcacccata ccctgcatct acccacaagc agaacagcca | 6360 |
| catactggtc cagccagaaa aagctgattc agctccagtt tctctgggat tataacttta | 6420 |
| tcttcgacca tactcttcag aagttgaggt ggggccacgg ccaaggcttt cttccacttg | 6480 |
| gaaagaagtt ccctcccttg atcgtctcca aacccttga aagtttactg gaacccaaat | 6540 |
| gaggcctggg ggtaaggaga gggggcctcc aaggactcct agtccagcgc tccttctggt | 6600 |
| cccacgcaat ctatccaagt ggtgcacact gagggttggg actgagacct aaaaaataat | 6660 |
| agagtgttca tctgcttgat ctgtttggtt tgcatttaag aaacacaatg gagtacagac | 6720 |
| agaccgttgg agatgggact ctattgttcc tatgtcccct ggtcagatag cattgccacc | 6780 |
| attctttctc caaaaagacc aggggcaggc tttgtgctac atatgtgcac agatatttt | 6840 |
| actaaccatc ataagaacct tggattgtag ttagtattgc ctttgcttta aaatgaggaa | 6900 |
| acgggctcag agagtttaag agacccagcc atgtttggtt ccatgttcac tattctagta | 6960 |
| ttgccctatg atgagcagct aacagaactg gactttggag gctgggttat tttgtccatt | 7020 |
| ggagctgaaa caggaaacta gggttcatag gtcaatgtag atttagcaat gactaatcct | 7080 |
| ccataaggcc ccagacacta tgacattgat gttctcattt aggccacata acttccaagt | 7140 |
| ggctatgaga ccattggaaa aaaaaaaaca aatttcagat aacttgccca atgtctcagt | 7200 |
| aacaaactga cctgtcaaag atct | 7224 |

<210> SEQ ID NO 34
<211> LENGTH: 4498
<212> TYPE: DNA
<213> ORGANISM: Homo sapiens

<400> SEQUENCE: 34

| | |
|---|---|
| aagcttggct ctggtttaga ttttccagga aaagccggaa tcaaattaca gaataaataa | 60 |
| aggcaaccat ccccctttta aaggtacacc agccttggtg catctttgaa gaaagcattc | 120 |
| tgtaaacccc aaccagaact aaactagtac gtcgaactca gattcatttt cactaaacca | 180 |
| caagcaaatg tttccctaaa aatcacccag ttaacaaagt ccgcatattt aagccaaaac | 240 |
| aatttaactg aacaaatggg ccacacgttg atttccggtc cctgctaata agtcagtctg | 300 |
| gaagttcaca ggtgtgccca tcctgccttg gctgctgaag tccaggtgtc tagggctgac | 360 |
| tgatgcccat tatgcctccc ctcccccatc tttgtcacag gatttgacgc accagctctc | 420 |
| caaatgaccc tggccctccc atttgctgtt cagcccaagt gcggagattg gctatgaacc | 480 |
| ctgtaaacag gcctctgacc cccagaggct gatggctggc caaggaaagc tgagctgctg | 540 |
| acgcagactg ggaagcaaga gcccacttcc agcagcccag gctagctgtg tccaaatcca | 600 |
| tgactgggga ggggttagag ccttgaggga caaaattatt ctacctacct agggagactg | 660 |
| cactggccca acagctgggc cccatctcat gggcccgctt cttcgccagg agagaagcca | 720 |
| ctccggggta ggtactgccc cacccaaacc cagccatctg gagtgaccca gccctggttc | 780 |
| ccaggtgtgt ggatgtgaat tgtcccaccc aacccactct acagtgagca acggaagcc | 840 |
| ctctgggaga gtggtcacag cctcccctgt acctttgaac agcctgccag gctccctact | 900 |
| cttaggcttc cactgtccac cagggaaagc cctgagctgg gagttgggga gcccccaggc | 960 |
| attgcccctg cccaggacac aattctcttt tgggatcagg gaaggctgtg agggcttttct | 1020 |
| aggtctcaag atcaggagct tgaagatgca gcctgggaag tgggaaggtg agaccaggac | 1080 |
| ataggccagc ctaaagcaag agtcctgggc ctgaaggctc ctgggaaggt ggtggggagg | 1140 |
| gagcatgtgt cggtggcctc agggcagcag ctgcctggtg aatgttcatg gactggatgc | 1200 |

```
tctgggaagc gggttgggtg gtgagcttct ctcttcccct ctgaagacgt cactggagtc   1260
tgggggtgga gctgcctggt ctataaatcc tggggccatc aggctgggt cctgcagctg    1320 cctgaaggag ccatctcatc cacagctctt ccttggtgag tggggagcct tccctaaggg   1380
ctaggacacc tgaaccaatt ttcatcctgg gcgtatggtg tgctgctcct cttccccatt   1440
cccaggtgcc tccaccctg aaccatgcca gagaagtccc cttttcctct cctctcccca    1500
acagctctac catctattct tgtgcttgtt gccctggca tgggagggat aaggggtaga    1560
agcacttgcc cccatcaata ccactcatcc attccacatc cccaactact atggaagaga   1620
tacagcaggc cacggagaaa agggcagaag cctgcaact ctggttccct agcactggtg    1680
ctccaaacac gcctacattg agaactcccc tgaccatcca tctatcctcc catccattgg   1740
cctgaattca ggtctctgtt cccctccaac tttcttccac ttctggaaac tccttgaagg   1800
aaagatggat ggacctggac aagtgggagg ccctcagag ctgcaaggc aggtagcctc     1860 tgtgccccag gctcagggag aaggctcgtc ccctggagca tcatccctg ctgggccagg    1920 atcccccagg atctggaccc ctgtatgctt ggatgagga gcggtggcag agagggaagg   1980
gcataaggag ataccaaagc tgcccctgag atgccagttt tccaaagtgg ccctggagga   2040
agtaggggga tgtggggtg aggtaagtct ccttgaatgc tgtaccctgt ccattagagc    2100
agccatggcc agctccaggc gaggcctcct gctcctgctg ctgctgactg cccaccttgg   2160
accctcagag gctcagcact ggtcccatgg ctggtaccct ggaggaaagc gagccctcag   2220
ctcagcccag gatccccaga atgcccttag gccccaggt gggtgtctcc cagcctcatg    2280
gggaggaaga aagtgatggc cgggggctcc cccaccctcc tggagcctga ggtcgggggta  2340 gggaggacag catcagttcc cttctaagga agggccctgg acactgcagc aggcagccca   2400
gtccagactg cccatggcct cccaagtgat gccctggctc cctggacga cagcatgccc    2460 tgggagggca ggaccacggc ccagtggtcc cttcacagga agcgacacct ggcacggaca   2520
ctgctggtga gtagggtgag aggtccccag catcaagacc agccactggt catcagaggc   2580
cattgtggct tagggttggg tgctgggagg gtggggagaa tgaaacacca ctgagatgcc   2640
ccctgccaca gcaccccag ccatttctca gtgccctac tgcacacagc agggtgctgt     2700
ctgctatcct tcctatttcc caggaggatt ctagacaatt tacaaagcac ttgggttaaa   2760
gaccaaagtc actagtagac tagaaggaga taattgttct ataagacagt ggtggccatg   2820
ggatcccaca gcatcctga caagccaatg actgtcttga ggtggacaga ccccaggcca    2880
gtggaaagag gtgagggatg caacctcact cagacaacag ggccaagagg accaggtggt   2940
gactgacatg tgcactagga acatctcagg gactgcagag ctccccaaga ccatagcaga   3000
agacaggcgt ggggaaatgg tttgctactg ttttgcaaat caaacattta cagtgcatca   3060
ggagagcccg gtaactaaag aagaaagtgg ttagttccta tgaggcaaag tcttaccgcc   3120
tgatttgtgt gtatgtgctg aggtttctat gcgtcaggct tgtttagggt ggacaagagg   3180
gcatgcccaa gggagctgga gatccccaca ctagctggat cctcaggctt ctacgggagg   3240
cggggggcgt cctgctgtgg gaggccacat ggggactggg ggggacgaga ggggagagaa   3300
ccaggaagat ggcagctcgg cggttacgag accagtgtcc tgagacatga ccgccacctc   3360
tccctccgca gaccgcagcc cgagagcccc gccccgcccc gccatcctcc aataaagtgt   3420
gaggttctcc gaagctgttg cgtcgagttc tgtccttcgt cccctccctg tcttccccgc   3480
tgagaccctt ccctgcgtgg gggctggagg gacgcgggtc cggccccgcg ggcgggagta   3540
actaagggat ggccccgggc cctggcggga aggccgggcc agagcctggg ggcgggatgc   3600
```

```
ggacgtccgc agggtcgccg cttcggttcc agaggccaca cggccgggcg gggcgtgagg      3660
gacagcccga ggactacagg tcccaaggtt ccccgcgccg cttccggggc acggtggcgt      3720
cccggcaccg cggccgcagt gaggagactc ggccatgcta cgcgcgctga gccgcctggg      3780
cgcggggacc ccgtgcaggc cccgggcccc tctggtgctg ccagcgcgcg gccgcaagac      3840
ccgccacgac ccgctggcca aatccaagat cgagcgagtg aacatgccgc ccgcggtgga      3900
ccctgcggag ttcttcgtgc tgatggagcg ttaccagcac taccgccaga ccgtgcgcgc      3960
cctcaggtgt gcggccgggg ggaggtggcc gcccgcgcgc gctggtgacg gtgggagtgg      4020
gcggagaggg tgctgattcc tggcgcgtct gcacccagga tggagttcgt gtccgaggtg      4080
cagaggaagg tgcacgaggc ccgagccggg gttctggcgg agcgcaaggc cctgaaggac      4140
gccgccgagc accgcgagct gatggcctgg aaccaggcg agaaccggcg gctgcacgag      4200
ctgcggtgcg tggggcggga ggcggggcgg ggcggcgcgg cctggccggc ctggagaag       4260 cccgggcccc gctcagcctc ggccctttga ccctcacagg atagcgaggc tgcggcagga      4320
ggagcgggag caggagcagc ggcaggcgtt ggagcaggcc cgcaaggccg aagaggtgca      4380
ggcctgggcg cagcgcaagg agcgggaagt gctgcagctg caggtgggca acgtttccgg      4440
agggtgggac tccagcgggg acgcggcttg cggggcactg gaattagata tcaagctt       4498

<210> SEQ ID NO 35
<211> LENGTH: 470
<212> TYPE: DNA
<213> ORGANISM: Homo sapiens

<400> SEQUENCE: 35
gggatctttt tggctctctg cctctaaaca gaatgaagcc aattcaaaaa ctcctagctg        60
gccttattct actgacttgg tgcgtggaag gctgctccag ccagcactgg tcctatggac       120
tgcgccctgg aggaaagaga gatgccgaaa atttgattga ttctttccaa gagatagtca       180
aagaggttgg tcaactggca gaaacccaac gcttcgaatg caccacgcac cagccacgtt       240
ctcccctccg agacctgaaa ggagctctgg aaagtctgat tgaagaggaa actgggcaga       300
agaagattta aatccattgg gccagaagga atgaccatta ctaacatgac ttaagtataa       360
ttctgacatt gaaaatttat aacccattaa atacctgtaa atggtatgaa tttcagaaat       420
ccttacacca agttgcacat attccataat aaagtgctgt gttgtgaatg                  470

<210> SEQ ID NO 36
<211> LENGTH: 423
<212> TYPE: DNA
<213> ORGANISM: Homo sapiens

<400> SEQUENCE: 36
ctgcagctgc ctgaaggagc catctcatcc acagctcttc cttgagcagc catggccagc        60
tccaggcgag gcctcctgct cctgctgctg ctgactgccc accttggacc ctcagaggct       120
cagcactggt cccatggctg gtaccctgga ggaaagcgag ccctcagctc agcccaggat       180
ccccagaatg cccttaggcc cccaggaagg gccctggaca ctgcagcagg cagcccagtc       240
cagactgccc atggcctccc aagtgatgcc ctggctcccc tggacgacag catgccctgg       300
gagggcagga ccacggccca gtggtccctt cacaggaagc gacacctggc acggacactg       360
ctgaccgcag cccgagagcc ccgccccgcc ccgccatcct ccaataaagt gtgaggttct       420
ccg                                                                    423
```

```
<210> SEQ ID NO 37
<211> LENGTH: 2735
<212> TYPE: DNA
<213> ORGANISM: Homo sapiens

<400> SEQUENCE: 37
ttggttgctg gtccacttac aaacactttt catatttgta tgtctttcca atggttatcc      60
tgttttgttc atttcaggca tatggccctg atcagattaa ctgacatgat gtatatgcaa     120
agccttttga gttcttcaga aaaataaatt atcttattca agactgattg cttataagga     180
acttattata gctaatatag taggcacaat ttttttgta attctcctag atgagtcaga      240
acttagtttt gatgtaggta aaatttat ggtcacaaat ctcaggtgtg agaaaatctc       300
tttccttgat actctatata aatagaggat ataaatattt caagtctgga agtagtgaga    360
gaagctggta attctggaca tatagtgaca gtcaaaaagg agctcaggta caggactggt    420
ctaagctgct caagattcag gagacagcca gtacacagag aagctgagga ataatacag     480 atatatctaa aacacttatc taaccttctg tggtaacaag ctccttaaag gggctggatg    540
atgttgtgtt cactttttat caccagcaaa ggctaagata atgtatatag taaatattta    600
gtaaccattt attaaataaa taatatttta agacagaata aacaagtata ataaatgaac    660
caataagaat gcaccatcta agtcaaaata gccacttttta tccttaacat tgtacctgct   720
ttggctgctg cagaagcaaa cttgttggca ttagacaaat caagctggtg atttaataaa    780
ttccaatgta agtcttacca gtattgatga ataactatcc agcactcacc atgaaagtta    840
aagaagcaac acagaaaaag ttcctaagtg gtcccaattt gaaatgatca gataacctat    900 aaagaacat attcatatta tactaacata aacacatata aatgcactta cagcagttac    960
acagtattct cttcaataac tagtttcctt atgcattaat gtgtaataac agcaactaca   1020
atatttagat aattataaaa accaaggcaa taatttaaaa actgattaac cgttttactc   1080
taacttaagc atggattgga tcagtaagat tgattaataa atttgaatgc agtcagttgg   1140
attgattcta atttaaagtt ttaatttgtt gtagaataat tttaagtgaa tatatttgtc   1200
cagtgttcga gtgctcaaca gtgtgttga aaaggaaaac aaagaatgtt ttgagaatgt    1260
gttaattcct taagacaatg gatttttaatt ggatctgttg ttttcattt tcttcattat    1320 cattatacat ctgtatgttg gacagaacac taacactaaa tagtttttag aaagtgtttt   1380
ttgaagttat ttaaatcata atatcatgac tgacttttga attcaaaatt aggctgtgac   1440
tatccttctt cacttaggaa gagtgttgtg aaagccagac catctgctga ggtgctacag    1500
ttacatgtgg ccctcagaat gcgtttggcc tgctctgttt tagcactctg ttggattacc    1560 aatcacaaa acaagttaac ctttgatctt tcacattaag tatctcaggg acaaatttg     1620 acatacgtct aaacctgtga cgtttccatc taaagaaggc agaaataaaa catggacttt   1680
agattcggtt acaataaaat atcagatgca ccagagacac aaggcttgaa gctctgtcct   1740
gggaaaatat ggcaaacagt gcctctcctg aacagaatca aaatcactgt tcagccatca   1800
acaacagcat cccactgatg cagggcaacc tccccactct gaccttgtct ggaaagatcc   1860
gagtgacggt tactttcttc cttttctgc tctctgcgac ctttaatgct tctttcttgt     1920
tgaaacttca gaagtggaca cagaagaaag agaagggaa aaagctctca agaatgaagc   1980
tgctcttaaa acatctgacc ttagccaacc tgttggagac tctgattgtc atgccactgg   2040
atgggatgtg gaacattaca gtccaatggt atgctggaga gttactctgc aaagttctca   2100
gttatctaaa gcttttctcc atgtatgccc cagccttcat gatggtggtg atcagcctgg   2160
accgctccct ggctatcacg aggcccctag ctttgaaaag caacagcaaa gtcggacagt   2220
```

```
ccatggttgg cctggcctgg atcctcagta gtgtctttgc aggaccacag ttatacatct    2280
tcaggatgat tcatctagca gacagctctg gacagacaaa agttttctct caatgtgtaa    2340
cacactgcag ttttcacaa tggtggcatc aagcatttta taacttttc accttcagct      2400 gcctcttcat catccctctt ttcatcatgc tgatctgcaa tgcaaaaatc atcttcaccc    2460
tgacacgggt ccttcatcag gaccccacg aactacaact gaatcagtcc aagaacaata     2520
taccaagagc acggctgaag actctaaaaa tgacggttgc atttgccact tcatttactg    2580
tctgctggac tccctactat gtcctaggaa tttggtattg gtttgatcct gaaatgttaa    2640
acaggttgtc agacccagta aatcacttct tctttctctt tgccttttta aacccatgct    2700
ttgatccact tatctatgga tatttttctc tgtga                               2735
```

<210> SEQ ID NO 38
<211> LENGTH: 20
<212> TYPE: DNA
<213> ORGANISM: Artificial
<220> FEATURE:
<223> OTHER INFORMATION: Synthetic

<400> SEQUENCE: 38
agtactcaac ctacttcaag                                                20

<210> SEQ ID NO 39
<211> LENGTH: 21
<212> TYPE: DNA
<213> ORGANISM: Artificial
<220> FEATURE:
<223> OTHER INFORMATION: Synthetic

<400> SEQUENCE: 39
cattcaaagc gttgggtttc t                                              21

<210> SEQ ID NO 40
<211> LENGTH: 18
<212> TYPE: DNA
<213> ORGANISM: Artificial
<220> FEATURE:
<223> OTHER INFORMATION: Synthetic

<400> SEQUENCE: 40
ctgcagctgc ctgaagga                                                  18

<210> SEQ ID NO 41
<211> LENGTH: 19
<212> TYPE: DNA
<213> ORGANISM: Artificial
<220> FEATURE:
<223> OTHER INFORMATION: Synthetic

<400> SEQUENCE: 41
ctaagggcat tctgggat                                                  19

<210> SEQ ID NO 42
<211> LENGTH: 21
<212> TYPE: DNA
<213> ORGANISM: Artificial
<220> FEATURE:
<223> OTHER INFORMATION: Synthetic

<400> SEQUENCE: 42
cacaatgtcc ggagcccttg a                                              21

-continued

```
<210> SEQ ID NO 43
<211> LENGTH: 22
<212> TYPE: DNA
<213> ORGANISM: Artificial
<220> FEATURE:
<223> OTHER INFORMATION: Synthetic

<400> SEQUENCE: 43
gcttaagagc ctatgcaaga ac                                            22

<210> SEQ ID NO 44
<211> LENGTH: 22
<212> TYPE: DNA
<213> ORGANISM: Artificial
<220> FEATURE:
<223> OTHER INFORMATION: Synthetic

<400> SEQUENCE: 44
ggcagaccga gatgaatcct ca                                            22

<210> SEQ ID NO 45
<211> LENGTH: 21
<212> TYPE: DNA
<213> ORGANISM: Artificial
<220> FEATURE:
<223> OTHER INFORMATION: Synthetic

<400> SEQUENCE: 45
caggtccagg ggtcttggtc c                                             21

<210> SEQ ID NO 46
<211> LENGTH: 21
<212> TYPE: DNA
<213> ORGANISM: Artificial
<220> FEATURE:
<223> OTHER INFORMATION: Synthetic

<400> SEQUENCE: 46
ccaagtcagt agaataaggc c                                             21

<210> SEQ ID NO 47
<211> LENGTH: 35
<212> TYPE: DNA
<213> ORGANISM: Artificial
<220> FEATURE:
<223> OTHER INFORMATION: Synthetic

<400> SEQUENCE: 47
gcaggaggcc tcgcctggag ctggccatgg ctgct                              35

<210> SEQ ID NO 48
<211> LENGTH: 24
<212> TYPE: DNA
<213> ORGANISM: Artificial
<220> FEATURE:
<223> OTHER INFORMATION: Synthetic

<400> SEQUENCE: 48
cagaggagaa tctgtgttac acag                                          24

<210> SEQ ID NO 49
<211> LENGTH: 21
<212> TYPE: DNA
<213> ORGANISM: Artificial
<220> FEATURE:
<223> OTHER INFORMATION: Synthetic
```

```
<400> SEQUENCE: 49
atatgctgct atgttggctg c                                                      21
```

METHODS AND PHARMACEUTICAL COMPOSITIONS FOR GNRH-I AND GNRH-II MODULATION OF T-CELL ACTIVITY, ADHESION, MIGRATION AND EXTRAVASATION

FIELD AND BACKGROUND OF THE INVENTION

The present invention relates to methods and compositions for the modulation of T-cell activity by GnRH-I and GnRH-II, and specific functional analogs of GnRH-I and GnRH-II receptors.

T-Cells in Immunity and Disease

Immune responses are largely mediated by a diverse collection of peripheral blood cells termed leukocytes. The leukocytes include lymphocytes, granulocytes and monocytes. Granulocytes are further subdivided into neutrophils, eosinophils and basophils. Lymphocytes are further subdivided into T and B lymphocytes. T-lymphocytes originate from lymphocytic-committed stem cells of the embryo. Differentiation occurs in the thymus and proceeds through prothymocyte, cortical thymocyte and medullary thymocyte intermediate stages, to produce various types of mature T-cells. These subtypes include CD4+ T cells (also known as T helper and T inducer cells), which, when activated, have the capacity to stimulate other immune system cell types. The T-helper cells are further subdivided into the Th1, Th2 and Th3 cells, primarily according to their specific cytokine secretion profile and function. T cells also include suppressor/regulator T cells (previously known as cytotoxic/suppressor T cells), which, when activated, have the capacity to lyse target cells and suppress $CD4^+$ mediated effects.

T-cell activation: Immune system responses are elicited in a variety of situations. The most frequent response is as a desirable protection against infectious microorganisms. The current dogma is that in the organism, under physiological conditions, resting T-cells are activated and triggered to function primarily by antigens which bind to T-cell receptor (TCR) after being processed and presented by antigen-presenting cells, or by immunocyte-secreted factors such as chemokines and cytokines, operating through their own receptors. Experimentally, T-cells can be activated by various non-physiological agents such as phorbol esters, mitogens, ionomycin, and anti-CD3 antibodies. To identify novel physiological means directly activating and/or regulating T-cells in conditions of health and disease, especially in non-lymphoid environments (e.g. brain) and in a TCR-independent manner, remains a challenge of scientific and clinical importance.

In recent years, it has become evident that specific immune responses and diseases are associated with T-helper (Th) functions. Among these are anti-viral, anti-bacterial and anti-parasite immune responses, mucosal immune responses and systemic unresponsiveness (mucosally induced tolerance), autoimmune reactions and diseases, allergic responses, allograft rejection, graft-versus host disease and others. Furthermore, specific T-cell mediated proinflammatory functions may have either beneficial or detrimental effects on specific neoplasias: on the one hand, proinflammatory cytokines may assist in anti-tumor immune surveillance, and, on the other, elevated levels of proinflammatory cytokines were found within chronically inflamed tissues that show increased incidence of neoplasia.

In general, CD4+ T-cells can be divided into at least two major mutually exclusive subsets, Th1 and Th2, distinguished according to their cytokine secretion profile. Th1 cells secrete mainly INF-γ, TNF-β and IL-2, their principal effector function being in phagocyte-mediated defense against infections. The Th1 cells are usually associated with inflammation, and induce cell-mediated responses.

Essential and beneficial immunity cannot take place without Th1 cytokines, but their over or dis-regulated production leads to numerous detrimental clinical consequences. Th2 cells induce B-cell proliferation and differentiation, and thus, induce immunoglobulin production. Cytokines from Th2 cells (mainly IL-4, IL-10 and IL-13) can also antagonize the effects of Th1 cell-mediated reactivities, inhibiting potentially injurious Th1 responses.

T-cell migration and integrin-fibronectin binding: Adhesion is important for a cell: it provides anchorage, traction for migration, signals for homing and regulates growth and differentiation. In the immune system, the ongoing migration, extravasation and homing of T-cells from the blood stream to various tissues and organs is crucially dependent on various adhesive interactions with ligands on target cell-surfaces and matrices.

A class of glycoproteins has been identified as comprising the receptors in the cell recognition system for cell-extracellular matrix interaction. These proteins, referred to as integrins, are characterized by the involvement of the RGD sequence in ligand recognition, and appear to play a significant role in the assembly of the extracellular matrix (Ruoslahti, E. "Versatile Mechanisms of Cell Adhesion," The Harvey Lectures, Series 84, pp 1-17 (1990)).

An integrin molecule is a heterodimeric membrane protein composed of one α and one β subunit. Several subunits of each kind are known, and various combinations of these subunits make up receptors with differing ligand specificities. The ligands for integrin are extracellular matrix proteins such fibronectin, lamanin, collagens and vitronectin or membrane proteins at the surface of other cells. By binding to their ligands, integrins mediate the adhesion of cells to extracellular matrices and to other cells.

Integrin functions have been shown to play a key role in a broad spectrum of normal and diseased conditions in general, and in inflammation and injury in particular. For example, T-cell recruitment into inflamed gingival tissues in periodontal disease (Taubman and Kawai, Crit. Rev Oral Biol Med 2001, 12(2) 125-35), and into the lamina propria in intestinal inflammation is associated with increased integrin expression. Normal cells are anchorage (integrin-fibronectin) dependent for progression through the cell cycle, whereas cancer cells exhibit anchorage-independent mitogenic activity. Furthermore, since resting T-cells cannot adhere, integrin-mediated fibronectin binding is indicative of significant activation and induction of T-cell function.

Three major events are involved in inflammation: (1) increased blood supply to the injured or infected area; (2) increased capillary permeability enabled by retraction of endothelial cells; and (3) migration of leukocytes out of the capillaries and into the surrounding tissue (Roitt et al., Immunology, Grower Medical Publishing, New York, 1989). Increased capillary permeability allows larger molecules to cross the endothelium that are not ordinarily capable of doing so, thereby allowing soluble mediators of immunity such as leukocytes to reach the injured or infected site. Leukocytes, primarily neutrophil polymorphs (also known as polymorphonuclear leukocytes, neutrophils or PMNS) and macrophages, migrate to the injured site by a process known as chemotaxis. At the site of inflammation, tissue damage and complement activation cause the release of chemotactic peptides such as C5a. Complement activation products are also responsible for causing degranulation of phagocytic cells, mast cells and basophils, smooth muscle contraction and increases in vascular permeability (Mulligan et al. 1991 J. Immunol. 148: 1479-1485).

The traversing of leukocytes from the bloodstream to extravascular sites of inflammation or immune reaction involves a complex but coordinated series of events. At the extravascular site of infection or tissue injury, signals are generated such as bacterial endotoxins, activated complement fragments or proinflammatory cytokines such as interleukin 1 (IL-1), interleukin 6 (IL-6), and tumor necrosis factor (TNF) which activate leukocytes and/or endothelial cells and cause one or both of these cell types to become adhesive. Initially, cells become transiently adhesive (manifested by rolling) and later, such cells become firmly adhesive (manifested by sticking). Adherent leukocytes travel across the endothelial cell surface, diapedese between endothelial cells and migrate through the subendothelial matrix to the site of inflammation or immune reaction (Harlan et al., Adhesion-Its role in Inflammatory Disease, W. H. Freeman & Co., New York, 1992).

Although leukocyte traversal of vessel walls to extravascular tissue is necessary for host defense against foreign antigens and organisms, leukocyte-endothelial interactions often have deleterious consequences for the host. For example, during the process of adherence and transendothelial migration, leukocytes release oxidants, proteases and cytokines that directly damage endothelium or cause endothelial dysfunction. Once at the extravascular site, emigrated leukocytes further contribute to tissue damage by releasing a variety of inflammatory mediators. Moreover, single leukocytes sticking within the capillary lumen or aggregation of leukocytes within larger vessels are responsible for microvascular occlusion and ischemia. Leukocyte-mediated vascular and tissue injury has been implicated in pathogenesis of a wide variety of clinical disorders such as acute and chronic allograft rejection, vasculitis, rheumatoid and other forms of inflammatory based arthritis, inflammatory skin diseases, adult respiratory distress syndrome, ischemia-reperfusion syndromes such as myocardial infarction, shock, stroke, organ transplantation, crush injury and limb replantation.

Many other serious clinical conditions involve underlying inflammatory processes in humans. For example, multiple sclerosis (MS) is an inflammatory disease of the central nervous system. In MS, circulating leukocytes infiltrate inflamed brain endothelium and damage myelin, with resultant impaired nerve conduction and paralysis (Yednock et al., 1992 Nature 366: 63-66). Systemic lupus erythematosus (SLE) is an autoimmune disease characterized by the presence of tissue damage caused by self antigen directed antibodies. Auto-antibodies bound to antigens in various organs lead to complement-mediated and inflammatory cell mediated tissue damage (Theofilopoubs, A. N. 1992 Encyclopedia of Immunology, pp. 1414-1417).

Reperfusion injury is another condition associated with activation of the inflammatory system and enhanced leukocyte-endothelial cell (EC) adhesion. There is much evidence that adhesion-promoting molecules facilitate interactions between leukocytes and endothelial cells and play important roles in acute inflammatory reaction and accompanying tissue injury. For example, in acute lung injury caused by deposition of IgG immune complexes or after bolus i.v. infusion of cobra venom factor (CVF), neutrophil activation and the generation of toxic oxygen metabolites cause acute injury (Mulligan et al., 1992 J. Immunol. 150(6): 2401-2405). Neutrophils (PMNs) are also known to mediate ischemia/reperfusion injury in skeletal and cardiac muscle, kidney and other tissues (Pemberton et al., 1993 J. Immunol. 150: 5104-5113). Infiltration of airways by inflammatory cells, particularly eosinophils, neutrophils and T lymphocytes are characteristic features of atopic or allergic asthma (Cotran et al., Pathological Basis of Disease, W. B. Saunders, Philadelphia, 1994). Cellular infiltration of the pancreas with resultant destruction of islet beta-cells is the underlying pathogenesis associated with insulin-dependent diabetes mellitus (Burkly et al. 1994 Diabetes 43: 529-534).

Activation of inflammatory cells whose products cause tissue injury underlies the pathology of inflammatory bowel diseases such as Crohn's disease and ulcerative colitis. Neutrophils, eosinophils, mast cells, lymphocytes and macrophages contribute to the inflammatory response. Minute microabcesses of neutrophils in the upper epithelial layers of the dermis accompany the characteristic epidermal hyperplasia/thickening and scaling in psoriasis.

Various anti-inflammatory drugs are currently available for use in treating conditions involving underlying inflammatory processes. Their effectiveness however, is widely variable and there remains a significant clinical unmet need. This is especially true in the aforementioned diseases where available therapy is either of limited effectiveness or is accompanied by unwanted side effect profiles. Moreover, few clinical agents are available which directly inhibit cellular infiltration, a major underlying cause of tissue damage associated with inflammation. Thus, there is a need for a safe, effective clinical agent for preventing and ameliorating cellular infiltration and consequential pathologic conditions associated with inflammatory diseases and injuries.

Modification of T-cell activity: Therapeutic application of T-cell modulating agents has been proposed for the treatment of conditions characterized by both immune deficiency and chronic inflammation. For example, U.S. Pat. No. 5,632,983 to Hadden discloses a composition consisting of peptides of thymus extract, and natural cytokines, for stimulation of cell mediated immunity in immune deficient conditions. Although significant enhancement of a number of cell mediated immune functions was demonstrated the effects were highly non-specific, as could be expected when employing poorly defined biologically derived materials.

Recently, Butcher et al. (U.S. Pat. No. 6,245,332) demonstrated the specific interaction of chemokine ligands TARC and MDC with the CCR4 receptors of memory T-cells, enhancing interaction of these cells with vascular epithelium and promoting T-cell extravasation. Therapeutic application of CCR4 agonists was disclosed for enhanced T-cell localization, and of antagonists for inhibition of immune reactivity, as an anti-inflammatory agent. Although the ligands were characterized, and identified in inflamed tissue, no actual therapeutic effects of agonists or antagonists were demonstrated.

Inhibition of a number of T-cell functions has been the target of many proposed anti-inflammatory therapies. Haynes et al. (U.S. Pat. No. 5,863,540) disclosed the use of anti-CD44 (cell adhesion molecule effecting T-cell activation) antibody for treatment of autoimmune conditions such as Rheumatoid Arthritis. Godfrey et al. (U.S. Pat. No. 6,277,962) disclosed a purified ACT-4 T-cell surface receptor expressed in activated CD4+ and CD8+ T-cells, and proposed the use of anti-ACT-4 antibodies to achieve downregulation of T-cell activation. Similarly, Weiner et al. (U.S. Pat. Nos. 6,077,509 and 6,036,457) proposed treatment with peptides containing immunodominant epitopes of myelin basic protein (associated with Multiple Sclerosis) for the specific suppression of CD4+ T-cell activity in this central nervous system autoimmune condition. However, none of the proposed applications were able to demonstrate any specific effect on the processes regulating expression of T-cell specific surface proteins responsible for immune activity.

Autoimmune Diseases

Autoimmune diseases are characterized by the development of an immune reaction to self components. Normally, tissues of the body are protected from attack by the immune system; in autoimmune diseases there is a breakdown of the self-protection mechanisms and an immune response directed to various components of the body ensues. Autoimmune diseases are for the most part chronic and require life long therapy. The number of recognized autoimmune diseases is large and consists of a continuum ranging from diseases affecting a single organ system to those affecting several organ systems. With increased understanding of the molecular basis of disease processes, many more diseases will likely be found to have an autoimmune component. Autoimmune diseases are typically divided into Organ Specific, and Non-Organ Specific Autoimmune disease. Specific examples of Organ Specific Autoimmune diseases are: Hashimoto's thyroiditis, Graves' disease, Addison's disease, Juvenile diabetes (Type I), Myasthenia gravis, pemphigus vulgaris, sympathetic opthalmia, Multiple Sclerosis, autoimmunehemolytic anemia, active chronic hepatitis, and Rheumatoid arthritis.

Rheumatoid arthritis is a systemic, chronic, inflammatory disease that affects principally the joints and sometimes many other organs and tissues throughout the body, characterized by a nonsuppurative proliferative synovitis, which in time leads to the destruction of articular cartilage and progressive disabling arthritis. The disease is caused by persistent and self-perpetuating inflammation resulting from immunologic processes taking place in the joints. Both humoral and T-cell mediated immune responses are involved in the pathogenesis of rheumatoid arthritis.

The key event in the pathogenesis of the arthritis is the formation of antibodies directed against other self antibodies. T cells may also be involved in the pathogenesis of rheumatoid arthritis. A large number of T cells are found in the synovial membrane, outnumbering B cells and plasma cells. Additionally, procedures to decrease the population of T cells (such as draining the thoracic duct) result in remission of symptoms.

Rheumatoid arthritis is a very common disease and is variously reported (depending on diagnostic criteria) to affect 0.5 to 3.8% of women and 0.1 to 1.3% of men in the United States.

Multiple sclerosis is a neurogenic disease that is thought to be caused by autoimmune mechanisms. The systemic immune response and the response of the central nervous system become involved. Although the cause and pathogenesis of multiple sclerosis are unknown, it is widely believed that immune abnormalities are somehow related to the disease. Suppression or modulation of the immune responses may be the key. Multiple sclerosis is modeled, in rodents, by the passive transfer of immune reactivity to Myelin Basic Protein via administration of sensitized T-cell (experimental autoimmune encephalomyelitis: EAE).

Myasthenia gravis is another nervous system related autoimmune disorder caused by antibodies directed against the acetylcholine receptor of skeletal muscle. In both experimental allergic myasthenia gravis and human myasthenia gravis, the extent of acetylcholine receptor loss parallels the clinical severity of the disease, suggesting that acetylcholine receptor antibody-induced acceleration of acetylcholine receptor degradation is important in the development of myasthenia gravis.

Other disorders, especially those presumed to be autoimmune in origin, can occur in association with myasthenia gravis. Thyroid disease, rheumatoid arthritis, systemic lupus erythematosus, and pernicious anemia all occur more commonly with myasthenia gravis than would be expected by chance.

One example of a non-organ specific Autoimmune disease is Systemic lupus erythematosus.

Acute attacks of Systemic lupus erythematosus are usually treated by adrenocortical steroids or immunosuppressive drugs. These drugs often control the acute manifestations. With cessation of therapy the disease usually reexacerbates. The prognosis has improved in the recent past; approximately 70 to 80% of patients are alive 5 years after the onset of illness and 60% at 10 years. Lifelong therapy is required to control the disease.

The foundation of therapy of autoimmune diseases is treatment with immunosuppressive agents. The basis for this therapy is attenuation of the self-directed immune response with the primary aim being to control symptoms of the particular disease. The drugs utilized to achieve this aim are far from satisfactory, in that adverse side effects are numerous and control of the disease is many times difficult to achieve. The problem is compounded by the chronicity of the disease with effective therapy becoming more difficult with time. An indication of the severity of particular diseases is seen in the willingness to accept greater risks associated with therapy as the disease progresses. Currently available therapy is distinctly non-selective in nature, having broad effects on both the humoral and cell mediated arms of the immune system. This lack of specificity can limit the effectiveness of certain therapeutic regimens. The main groups of chemical immunosuppressives are alkylating agents, antimetabolites, corticosteroids, and antibiotics, each will be discussed briefly.

The corticosteroids, also called adrenocorticosteroids, are fat-like compounds produced by the outer layer or cortex, of the adrenal gland. Therapeutic use of the corticosteroids for autoimmune disease is based on their two primary effects on the immune system, anti-inflammatory action and destruction of susceptible lymphocytes. They also effect a redistribution of lymphocytes from peripheral blood back to the bone marrow. The use of corticosteroids is not without adverse side effects however, particularly during the course of life-long treatment which is required for many of the autoimmune diseases.

Major side effects of steroids are: Cushing syndrome, muscle atrophy, osteoporosis, steroid induced diabetes, atrophy of the adrenal glands, interference with growth, susceptibility to infections, aseptic bone necrosis, cataract development, gastric ulcer, steroid psychosis, skin alterations and nervous state accompanied by insomnia.

Attempts to minimize side effects incorporate alternate day or less frequent dosage regimens.

Another recently developed immunosuppressive agent is the antibiotic cyclosporin A. The antibiotic has greatest activity against T cells and does not seem to have much direct effect on B cells. The drug is being evaluated for the treatment of autoimmune diseases for which it shows some promise. Side effects include hair growth, mild water retention, renal toxicity, and, in older patients, nervous system disorders symptoms have been observed.

Other drugs are used alone or in combination with those listed above and include gold salts and antimalarials, such as chloroquine. Another class of drugs, the non-steroidal anti-inflammatory drugs are used extensively in arthritis. These drugs provide analgesia at low doses and are anti-inflammatory after repeated administration of high doses. Nonsteroidal anti-inflammatory drugs all act rapidly and their clinical effects decline promptly after cessation of therapy. However, they do not prevent the progression of rheumatoid arthritis, do not induce remissions, and are frequently associated with dangerous gastrointestinal side effects. Immunostimulants, such as levamisol have also been used in many autoimmune diseases but side effects have generally limited their use. Clearly, new therapies and drugs for the treatment of autoimmune disorders are needed.

Lymphocytes in Cancer Immunotherapy

Immunotherapy in cancer patients is usually directed to the production or stimulation of populations of reactive antitumor lymphocytes, to provide specific and natural cytotoxic effects directed against highly expressed tumor antigens. Many studies have reported successful immunization of human and non-human subjects with cancer antigens to stimulate circulating cytotoxic T-cell precursors (see, for example, Rosenberg, S A et al, Nature Med 1998; 4: 321), however, this has not yet correlated with any clinically significant effect. In another method for stimulation of antitumor immunotoxicity, Ostrand-Rosenberg et al (U.S. Pat. No. 6,319,709) disclosed the ex-vivo modification of tumor cells, and their re-introduction into the patient, to stimulate a beneficial anti-cancer immune response.

Another approach is the adoptive transfer of selected and expanded sub-populations of anti-tumor lymphocytes. For example, adoptive transfer of tumor infiltrating lymphocytes (TIL), along with interleukin-2 treatment, can mediate the regression of established lung and liver metastases (Rosenberg, S. A., et al., Science 1998; 233: 1318-1321). However, engraftment and persistence of the transferred cells has not been generally observed. Recent reports of successful tumor regression in melanoma patients receiving clonal repopulation with antitumor lymphocytes, following lymphodepletion, also emphasized the requirement for IL-2 treatment, and the danger of autoimmune side-effects (Dudley, M E et al, Science 2002; 298: 850-54). Thus there is a great need for new anti-cancer T-cell therapies.

Neurotransmitters and Immune System Function

It is generally accepted that the immune, nervous and endocrine systems are functionally interconnected. The significance of direct neuronal signaling on immune system components, including T-cells, can be appreciated considering the extensive innervation of all primary and secondary lymphoid tissue; the presence of both peptidergic and non-peptidergic neurotransmitters in capillaries and at sites of inflammation, injury or infection; and the demonstrated expression of specific receptors for various neurotransmitters on T-cell (and other immune system components) surface membrane.

Specific modulation of immune function has been demonstrated for a number of neurotransmitters. Recently, neuropeptides somatostatin (SOM), calcitonin gene related peptide (cGRP), neuropeptide Y (NPY) and also Dopamine were found to interact directly with specific receptors on the T-cell surface, while substance P (Sub P) indirectly affected T-cell function. These neurotransmitters exert both inhibitory and stimulatory influence on T-cell cytokine secretion, adhesion and apoptosis, depending on T-cell lineage and activation states (Levite, M.: Nerve Driven Immunity. The direct effects of neurotransmitters on T-cell function. Ann NY Acad. Sci. 2001 917: 307-21). Similarly, physiological concentrations of the neurotransmitters SOM, Sub P, cGRP and NPY were found to directly induce both typical and non-typical cytokine and chemokine secretion from T-cells and intestinal epithelium, thus either blocking or evoking immune function (Levite, M. Nervous immunity: neurotransmitters, extracellular $K^+$ and T-cell function. Trends Immunol. 2001 January; 22(1): 2-5). Clearly, immune function is sensitive to neurogenic control.

A number of therapeutic applications of immune modulation by manipulation of neurotransmitters have been proposed. In one, botulinum toxin's peptide-lytic activity is employed to reduce the effect of immune-active neurotransmitters Sub P, cGRP, NK-1, VIP, IL-1 and IL-6 and others on neurogenic inflammatory conditions such as arthritis, synovitis, migraine and asthma (U.S. Pat. No. 6,063,763 to First). Hitzig (U.S. Pat. No. 5,658,955) proposes the combined application of neurotransmitters Dopamine and serotonin for complex inhibition and stimulation of various immune functions, for the treatment of AIDS and HIV infection, cancers, migraine, autoimmune inflammatory and allergic conditions, chronic fatigue syndrome and fibromyalgia. On the whole, however, the immune modulation of these inventions is of a broad and non-specific nature, with significant likelihood of undesirable complications and side effects in practice. In addition, no clear mechanism of action was defined for the immune-modulatory effects of Dopamine and serotonin in the latter disclosure. Thus, there is a need for improved methods of modulation of immune function via specific neuropeptides and defined pathways of immune activation.

GnRH-I and GnRH-II: The Gonadotropin releasing hormone-II (GnRH-II), is a unique ten amino acid long neuropeptide, which is conserved throughout 500 million years of evolution, and has recently been identified in the brain and non-neural (kidney, bone marrow, prostate and placenta) tissues of various mammals. The peptide structure of GnRH-II shares 70% homology with that of the known mammalian neurohormone, GnRH (GnRH-I), but is encoded by its own gene. In contrast to GnRH-II, which is the prime regulator of reproduction, GnRH-II exerts only very mild effects on reproduction in mammals, and its principal physiological role remains unclear (see, for example, Fink, G. Gonadotropin secretion and its control; in The Physiology of Reproduction (eds Knobil, E. & Neill, J. D.) 1349-1377 (Raven Press, New York, 1988). The two GnRH isoforms are produced mainly in areas of the brain stem and hypothalamus, with axons of the hypothalamic GnRH neurons terminating in the infundibulum, close to the fenestrated portal capillary plexus. The strict evolutionary conservation of GnRH-II, from primitive vertebrates to mammals, taken together with its different functional profile as compared to GnRH-I, suggests that it may have different, yet undiscovered, important physiological functions.

Surprisingly, it was recently demonstrated that the promoters of GnRH-I and GnRH-II are differentially regulated, suggesting distinct physiological functions for the two isoforms (Chen et al. Transcriptional regulation of the human gonadotropin-releasing hormone II gene is mediated by a putative cAMP response element. Endocrinology, In Press August, 2001). In bullfrogs, GnRH-II, and GnRH-I, to a lesser extent, have sympathetic neurotransmitter function. Although only one GnRH receptor has been characterized in mammals, high affinity receptors binding GnRH II have been demonstrated in catfish and goldfish, suggesting that additional GnRH II receptors may also be present in mammals. Niell (Neill J D et al, Arch. Physiol Biochem 2002; 110: 129-36) described a putative human GnRH-II receptor mRNA (NCBI Accession number NM 057163), sharing only 55% homology with the human GnRH-II receptor, identified on the basis of sequence homology with non-human species GnRH-I receptor. However, the function and identity of this putative receptor have yet to be definitively determined.

Analogs of GnRH are commonly used for intervention in the reproductive cycles and behavior of mammals and lower vertebrates (see, for example, Millar, R P et al. J. Biol. Chem. 1989, 264: 21007-013). Thus, certain modifications in GnRH structure (for example, positions 8, 9 and 10) have been recognized to confer characteristically agonist properties, while others (positions 1, 2, 3 and 6) produce antagonist analogs. These effects seem to demonstrate species, and growth-stage specific variance. In clinical application, native GnRH peptides have demonstrated only minimal potency via oral administration, and pharmaceutical compositions of GnRH analogs have been proposed, for example, for modulation of sex hormone levels in mammals (U.S. Pat. No. 5,140,009 to Haviv et al.) and treatment of male pattern baldness (U.S. Pat. No. 5,574,011 to Tein).

Walsh et al. and Goulet et al. (U.S. Pat. Nos. 6,228,867 and 5,985,901, respectively) disclose the application of a variety of non-peptide GnRH antagonists for the treatment of endometriosis, uterine fibroids, prostate, ovarian and mammary cancer, PMS, irritable bowel syndrome, precocious puberty, and for use in contraception and assisted fertilization techniques. The non-peptide analogs are emphasized for their superior oral potency, and all of the disclosed embodiments are based on the inhibition of Leutinizing Hormone and Follicle Stimulating Hormone release.

Analogs of GnRH are known to inhibit the growth of gonadal steroid-dependent tumors by both sex hormone deprivation and a direct effect on the cancer cells. Thus, GnRH has been applied, for example, for preoperative androgen block in prostate adenocarcinoma (Sharkey, J. et al. J. Endourol 2000 May; 14(4): 343-50) and in combination with tamoxifen in treatment of breast cancer (Klijn, J G et al., J. Clin Oncol 2001 Jan. 15; 19(2) 343-53). Direct effects are presently unclear, however: although many mammary cancer cells, for example, express GnRH binding sites, some also express the GnRH gene, suggesting autocrine and/or paracrine effects in these cells. Effective inhibition of mammary tumor growth is achieved with relatively high dosage of GnRH and its analogs. Attempting to avoid some of the disadvantages of GnRH I and GnRH II analogs, Lovas et al. (U.S. Pat. No. 5,593,965) has disclosed the therapeutic use of Lamprey GnRH-II, a natural GnRH analog lacking mammalian gonadotropic activity, for inhibiting mammary tumor proliferation. No mention is made of neuroimmune interaction, inhibition of steroid independent cancers or ex-vivo treatment and re-introduction of autologous immune cells.

Non-gonadal cancers may also express GnRH binding sites: colon adenocarcinoma cells were effectively inhibited in vitro and in vivo by exposure to the chimeric protein L-GnRH-PE66 (Ben-Yehudah, A. et al. Int J Cancer 2001 Apr. 15; 92(2): 263-8), targeting the cancer cells with the GnRH peptides. However, toxicity, associated pain and the need for frequent administration were reported disadvantages of the treatment.

Alterations in immune function have been observed in correlation with administration of GnRH or analogs, in both clinical and experimental studies. For example, GnRh antagonist treatment of neonatal rhesus monkeys and marmosets resulted in reduced T-cell proliferation and impaired resistance to disease (Mann, D R et al Am J Reprod Immunol 2000; 44: 30-40), while women receiving GnRH agonists for endometriosis demonstrated increased T-cell and NK cell counts (Hsu C C et al Obstet Gynecol 1977; 89: 993-8). However, these effects involved complex endocrine and metabolic interactions, and no demonstration of direct effects of GnRH of T-cells were observed.

Neuroprotective Immunity: In the context of neuroimmune interaction, the recent discovery of neuroprotective interactions between T-cells and neuronal tissue in neurotoxicity, disease and injury is intriguing. Several studies by Schwartz, et al have shown that T-cell deficient mice are more susceptible to experimentally induced neuronal injury and neurotoxicity, and that reconstitution with wild-type splenocytes can effectively restore resistance. Additional evidence for such protective autoimmunity in CNS trauma was provided by the demonstration of potentiation of neuronal survival by prior, unrelated CNS insult in autoimmune encephalomyelitis-resistant strains of mice (see, for example, Yoles, et al, J Neurosci 2001, Jun. 1; 21(11): 3740-48; Kipnis, et al, J Neurosci 2001 Jul. 1; 21(13): 4564-71; and Schori, et al, J Neuroimmunol 2001 Oct. 1: 119(2): 199-204). Clinical application of such neuroprotective immunity has been proposed, employing vaccination with non-pathogenic CNS derived peptides such as MBP to boost innate beneficial autoimmunity (Schwartz and Kipnis, Trends Mol Med 2001 June; 7(6): 252-58; and Schwartz, Surv Ophthalmol 2001 May; 45 Suppl 3: S256-60) and stimulation of peripheral monocytes for enhancement of axonal regeneration (U.S. Pat. No. 6,117,242 to Eisenbach-Schwartz). No mention is made of GnRH or GnRH analog modulation of T-cell activity, and furthermore, the authors note the substantial risk of inducing undesired autoimmune disease using immunization with self antigens.

Studies of lymphocyte activation in other neurogenic conditions also indicate a potential neuroprotective role of immune cells: in patients with encephalitis and MS, the beneficial brain-derived-neurotrophic-factor BNDF is secreted by immune cells in response to CNS auto-antigen stimulation (Kerschensteiner, et al, J Exp Med 1999 Mar. 1; 189(5): 865-70). Furthermore, in clinical trials of an altered peptide ligand of myelin basic protein administered to patients with relapsing-remitting MS, reduction in lesion volume and number was achieved in the MBP-treated patients compared to the placebo group. However, the dosage required was high (5 mg), and the trial was suspended due to undesirable side effects (hypersensitivity). No mention was made of GnRH stimulation of T-cells.

Neuroimmunology and Psychopathology: Many studies have demonstrated significant correlation between immune function and a variety of emotional and psychopathological conditions, especially schizophrenia and suicide (see, for example, Sperner-Unterweger B, et al, Scizophr Res 1999; 38: 61-70; Staurenghi A H, et al Psychoneuroendocrinology 1997; 22: 575-90; van Gent T, et al J Child Psychol Psychiatry 1997; 38: 33749; Nassberger L and Traskman-Bendz L Acta Psychiatr Scand 1993; 88: 48-52; and Dabkowska M and Rybakowski J Psychiatr Pol 1994; 28: 23-32). Presently it remains unclear whether the dysfunctional immune responses observed contributeo the psychopathogenic processes, are secondary to them, or a combination of the two.

T-cell enhancement has been observed in schizophrenia, and has been suggested as a marker of therapeutic outcome or neuroleptic treatment (Muller, et al Acta Psychiatr Scand 1993; 87: 66-71 and Sperner-Unterweger B et al Scizophr Res 1999; 38: 61-70). The authors made no mention of T-cell-related therapy or GnRH modulation of T-cell activity for treatment or prevention of the abovementioned disorders.

Manipulation of immune cells for therapy of brain related disorders has been proposed by Wank (Intern Pats. WO9950393A2 and WO9950393A3 to Wank, R). Wank describes the in-vitro activation of peripheral blood monocytes (PBMC), or phagocytes, for the treatment of a variety of brain-related disorders, including psychoses, schizophrenia, autism, Down's syndrome, disturbances of cerebral development and brain injury, based on the observation of inadequate immune responses in these conditions. In a report documenting adoptive immunotherapy of patients suffering from bipolar disorder, schizophrenia or autism, Wank describes the in-vitro activation, and reintroduction of the patients' own T-cells, in order to combat "chronically infected", under-stimulated lymphocytes thought associated with these disorders. In this form of therapy, the T-cells are not stimulated directly, rather via monoclonal antibodies against the CD3 polypeptide complex, and IL-2. The patients were required to endure numerous weekly treatments (up to 104 weeks in one patient), and although improvement in some symptoms was noted, additional therapies were continued during and after these trials of adoptive immunotherapy. No mention is made of direct stimulation of T-cells with neuropeptides, of specific T-cell response to therapy, or of treatment with GnRH or GnRH analogs.

To date, the dynamics of GnRH interaction with specific GnRH receptors on normal and diseased human T-cells have not been addressed directly.

While reducing the present invention to practice, the present inventor has uncovered, for the first time, that physiological concentrations of GnRH, acting directly on T cells via well characterized GnRH receptors, can modify numerous important T cell functions, such as, for example, induction of gene expression, most significantly of the 67 kD non-integrin laminin receptor, adhesion to laminin, chemotaxis and T-cell extravasation. Whereas GnRH effects on T cells have been previously unknown, the present invention surprisingly demonstrates that GnRH I and GnRH II act directly to modulate specific gene expression, and upregulate GnRH expression and secretion in normal and cancerous human T cells. Thus, the present invention provides methods for the modulation of T-cell activity by GnRH and specific GnRH receptor functional analogs and, more particularly, methods for the treatment of bacterial, viral, fungal infectious and parasitic diseases, containment of auto-immune and other injurious inflammatory processes, inhibition and prevention of tumor growth and dissemination, and prevention of host rejection of engrafted tissue employing GnRH receptor-mediated regulation of T-cell laminin-binding activity and extravasation, devoid of the above limitations.

SUMMARY OF THE INVENTION

According to the present invention there is provided a method of regulating activity of a T-cell population, the method comprising providing to the T-cell population a molecule selected as being capable of modifying an activity or expression level of a GnRH-I or a GnRH-II receptor of T-cells of the T-cell population, thereby regulating GnRH-I or GnRH-II mediated activity in the T-cell population.

According to further features in described preferred embodiments the T-cell population is a resting T-cell population.

According to another aspect of the present invention there is provided a method of regulating T-cell activity in a mammalian subject having abnormal T-cell activity, the method comprising providing to a subject identified as having the abnormal T-cell activity a therapeutically effective amount of a molecule selected as being capable of modifying an activity or expression level of a GnRH-I or a GnRH-II receptor thereby regulating T-cell activity in the mammalian subject.

According to still another aspect of the present invention there is provided a method of treating or preventing a T-cell related disease or condition characterized by abnormal T-cell activity in a mammalian subject, the method comprising providing to a subject identified as having the T-cell related disease or condition characterized by abnormal T-cell activity a therapeutically effective amount of a molecule selected as being capable of modifying an activity or expression level of a GnRH-I or a GnRH-II receptor, said amount being sufficient to regulate T-cell activity, thereby treating or preventing the T-cell related disease or condition in the mammalian subject.

According to another aspect of the present invention there is provided an assay for determining the sensitivity of a resting T-cell population to modification of GnRH-I or GnRH-II receptor activity, the assay comprising:

(a) exposing the T-cell population to a molecule selected as being capable of modifying an activity or expression level of a GnRH-I or a GnRH-II receptor, and (b) assessing a state of the T-cell population.

According to further features in described preferred embodiments, step (a) is effected by exposing the T-cell population to a range of concentrations of said molecule, and whereas step (b) is effected by assessing said state at each concentration of said range.

According to yet further features in described preferred embodiments, step (b) is effected by determining an activity selected from the group consisting of 67 KDa non-integrin laminin receptor expression, laminin adhesion, chemotaxis, extravasation, migration and organ invasion.

According to further features in described preferred embodiments, said molecule is selected as being capable of upregulating or downregulating said activity or expression level of a GnRH-I or a GnRH-II receptor, thereby upregulating or downregulating GnRH-I or GnRH-II mediated activity of said T-cells of the T-cell population.

According to yet further features in described preferred embodiments, said molecule selected as being capable of upregulating said activity or expression level of a GnRH-I or a GnRH-II receptor is selected from the group consisting of GnRH-I or GnRH-II, an upregulating GnRH-I or GnRH-II analog, an upregulating anti GnRH-I or GnRH-II receptor antibody and an expressible polynucleotide encoding a GnRH-I or GnRH-II receptor.

According to still further features in described preferred embodiments, said molecule selected as being capable of downregulating said activity or expression level of a GnRH-I or a GnRH-II receptor is selected from the group consisting of a downregulating GnRH-I or GnRH-II analog, a down-regulating anti GnRH-I or GnRH-II receptor antibody, a single stranded polynucleotide designed having specific GnRH-I or GnRH-II receptor transcript cleaving capability, an expressible polynucleotide encoding a ribozyme designed having specific GnRH-I or GnRH-II receptor transcript cleaving capability, a polynucleotide designed comprising nucleotide sequences complementary to, and capable of binding to GnRH-I or GnRH-II receptor transcripts, coding sequences and/or promoter elements and an expressible polynucleotide encoding nucleotide sequences complementary to, and capable of binding to GnRH-I or GnRH-II receptor transcripts, coding sequences and/or promoter elements.

According to still further features in described preferred embodiments, said upregulating or downregulating GnRH-I or GnRH-II analog is selected from the group consisting of naturally occurring, synthetic, decapeptide and peptide fragment analogs.

According to further features in described preferred embodiments, said upregulating or downregulating anti-GnRH-I or GnRH-II receptor antibody is a monoclonal or a polyclonal antibody.

According to yet further features in described preferred embodiments, said expressible polynucleotide encoding a GnRH-I or GnRH-II receptor is designed so as to be capable of transient expression within cells of the T-cell population or T-cells of the subject.

According to still further features in described preferred embodiments, said expressible polynucleotide encoding a GnRH-I or GnRH-II receptor is designed so as to be capable of stably integrating into a genome of cells of the T-cell population or T-cells of the subject.

According to further features in described preferred embodiments, said expressible polynucleotide includes a sequence as set forth in SEQ ID NO: 37.

According to yet further features in described preferred embodiments, regulating GnRH-I or GnRH-II mediated activity in the T cell population or the mammalian subject results in a change in at least one T cell activity selected from the group consisting of 67 KDa non-integrin laminin receptor expression, laminin adhesion, chemotaxis, extravasation, migration and organ invasion.

According to still further features in described preferred embodiments, regulating GnRH-I or GnRH-II mediated activity further comprising the step of monitoring said at least one T-cell activity in the T-cell population or in T-cells of the subject.

According to further features in described preferred embodiments, monitoring said at least one T-cell activity is effected by determining at least one parameter selected from the group consisting of gene expression, 67 kDa non-integrin laminin receptor expression, laminin adhesion, chemotaxis, extravasation, migration and organ invasion.

According to yet further features in described preferred embodiments, said step of providing said molecule is effected by systemic or local administration of said molecule to the subject.

According to still further features in described preferred embodiments, said step of providing said molecule is effected by providing said molecule to an ex-vivo T-cell population and administering said ex-vivo T-cell population to the subject.

According to yet further features in described preferred embodiments, the T-cell related disease or condition is a disease or condition characterized by suboptimal T-cell activity selected from the group consisting of congenital immune deficiencies, acquired immune deficiencies, infection, neurological disease and injury, psychopathology and neoplastic disease; and whereas said molecule is selected as being capable of upregulating an activity or expression level of a GnRH-I or a GnRH-II receptor.

According to still further features in described preferred embodiments, the T-cell related disease or condition is a disease or condition characterized by excessive T-cell activity selected from the group consisting of autoimmune, allergic, neoplastic, hyperreactive, pathopsychological and neurological diseases and conditions, graft-versus-host disease, and allograft rejections and whereas said molecule is selected as being capable of downregulating an activity or expression level of a GnRH-I or GnRH-II receptor.

According to further features in described preferred embodiments, the subject is suffering from a cancerous disease or condition characterized by excess T-cell activity, and whereas the method further comprising the step of determining cancer cell proliferation and/or metastasis in the subject prior to and/or following said step of providing.

According to yet further features in described preferred embodiments, said cancerous disease or condition characterized by excess T-cell activity is a myeloproliferative disease.

According to still further features in described preferred embodiments, the T-cell related disease or condition is an infectious disease or condition characterized by 67 kDa laminin receptor-mediated pathogen binding activity, and whereas said molecule is a molecule selected as being capable of down-regulating an activity of a GnRH-I or GnRH-II receptor, thereby suppressing said T-cell related infectious disease.

According to further features in described preferred embodiments, said molecule selected as being capable of downregulating an activity or expression level of a GnRH-I or a GnRH-II receptor is a downregulator of an activity or expression level of a 67 kDa laminin receptor.

According to still further features in described preferred embodiments, treating or preventing a T-cell related disease further comprising the step of monitoring a symptom of said T-cell related infectious disease or condition in the subject prior to and/or following said step of providing.

According to yet further features in described preferred embodiments, said T-cell related infectious disease is selected from the group consisting of Sindbis virus, a tick-borne encephalitic virus, and prion diseases.

According to the present invention there is provided a population of T-cells suitable for treating or preventing a disease or condition characterized by abnormal T-cell activity in a subject, the population of T cells comprising T-cells characterized by modified sensitivity to GnRH-I or GnRH-II receptor stimulation, said T-cells being capable of treating or preventing a disease or condition characterized by abnormal T-cell activity upon administration to the subject.

According to further features in described preferred embodiments, said T-cells comprise an exogenous expressible polynucleotide sequence encoding a GnRH-I or GnRH-II receptor.

According to still further features in described preferred embodiments, said T-cells comprise an exogenous polynucleotide sequence capable of downregulating expression of a gene encoding a GnRH-I or GnRH-II receptor.

According to yet another aspect of the present invention there is provided an article of manufacture, comprising packaging material and a therapeutically effective amount of a pharmaceutical composition being identified for the treatment of a T-cell related disease or condition associated with abnormal T-cell activity, said pharmaceutical composition including a molecule selected as being capable of modifying an activity or expression level of a GnRH-I or a GnRH-II receptor in T-cells and a pharmaceutically acceptable carrier.

According to further features in described preferred embodiments, said molecule is capable of upregulating or downregulating an activity or expression level of a GnRH-I or a GnRH-II receptor in T-cells and whereas the T-cell related disease or condition is a disease or condition characterized by suboptimal T-cell activity.

According to yet further features in described preferred embodiments, said molecule selected as being capable of upregulating an activity or expression level of a GnRH-I or a GnRH-II receptor is selected from the group consisting of GnRH-I or GnRH-II, an upregulating GnRH-I or GnRH-II analog, an upregulating anti GnRH-I or GnRH-II receptor antibody and an expressible polynucleotide encoding a GnRH-I or GnRH-II receptor.

According to still further features in described preferred embodiments, said molecule is capable of downregulating an activity or expression level of a GnRH-I or a GnRH-II receptor in T-cells and whereas the T-cell related disease or condition is a disease or condition characterized by excessive T-cell activity.

According to further features in described preferred embodiments, said molecule selected as being capable of downregulating an activity or expression level of a GnRH-I or a GnRH-II receptor is selected from the group consisting of a downregulating GnRH-I or GnRH-II analog, a downregulating anti GnRH-I or GnRH-II receptor antibody, a single stranded polynucleotide designed having specific GnRH-I or GnRH-II receptor transcript cleaving capability, an expressible polynucleotide encoding a ribozyme designed having specific GnRH-I or GnRH-II receptor transcript cleaving capability, a polynucleotide designed comprising nucleotide sequences complementary to, and capable of binding to GnRH-I or GnRH-II receptor transcripts, coding sequences and/or promoter elements and an expressible polynucleotide encoding nucleotide sequences complementary to, and capable of binding to GnRH-I or GnRH-II receptor transcripts, coding sequences and/or promoter elements.

According to further features in described preferred embodiments, said T-cell related disease or condition is an infectious disease characterized by 67 kDa laminin receptor mediated pathogen binding.

According to still further features in described preferred embodiments, said infectious disease is selected from the group consisting of Sindbis virus, a tick-borne encephalitic virus and prion disease.

The present invention successfully addresses the shortcomings of the presently known configurations by providing, for the first time, methods and materials for modulation of T-cell activity by direct stimulation of T-cell GnRH-I or GnRH-II receptors, and for regulation of T-cell GnRH-I or GnRH-II receptor sensitivity.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1B, GnRH-II-treated cells). Over expression of laminin receptor (LR) in GnRH-II treated cells (FIG. 1B) compared to untreated cells (FIG. 1A) is visualized in coordinate n13. In contrast, coordinate j8 indicates the expression of nucleoside diphosphate kinase B that remained unchanged following GnRH-II treatment. FIG. 1C represents the control hybridizations for the untreated cells (upper panel) and the GnRH-II treated cells (lower panel). Number 1 serves as an orientation marker. The housekeeping genes are located in numbers 4, 9, 14, 15 and 16 and stand for Ubiquitin, G3PDH, cytoplasmic beta actin, 45-kDa calcium binding protein precursor and ribosomal protein S29, respectively. The negative controls are: M13 mp18(+) strand DNA, lambda DNA and pUC18 DNA which are located in numbers 3, 8 and 13, respectively. Mouse genomic DNA is spotted in numbers 2, 7 and 12.

FIGS. 1E and 1F demonstrate the presence of laminin receptor and S14 gene expression in human peripheral T-cells, treated with GnRH-I (FIG. 1E) or GnRH-II (FIG. 1F) in a time dependent manner. Each PCR tube contained four oligonucleotides primers, two for the 67 kDa LR and two for the internal control (S-14). Southern hybridizations were performed, sequentially on the same membrane, using $^{32}$P labeled probes, specific to 67 kDa LR (upper panel) or S14 (lower panel). The radioactive bands were quantified by a phosphorimager and the normalized values (relative to the control, S14 expression) are presented as fold increase compared to the control group, for the GnRH-I treatment (FIG. 1E, graph) and GnRH-II treatment (FIG. 1F, graph). Note that the LR mRNA level in the GnRH-II treated cells is about 10 fold higher than that of the untreated cells (FIG. 1F), while that of the GnRH-I treated cells is about 3 fold higher (FIG. 1E).

FIG. 2D depicts quantitative RT-PCR of laminin receptor and S14 transcripts obtained from peripheral human T-cells. The cells either remained untreated (lane 1) or treated with 10 nM GnRH-I (lane 2), 10 nM GnRH-II (lane 3), 100 nM GnRH-I receptor antagonist (Cetrorelix, lane 4), 10 nM GnRH-I+100 nM Cetrorelix (lane 5), 10 nM GnRH-II+100 nM Cetrorelix (lane 6), or TCR activating anti-CD3+ anti-CD28 activating mAbs (lane 7). Each PCR tube contained four oligonucleotides primers, two for the LR and two for the internal control (S-14). The ethidium bromide bands were quantified and the normalized values (relative to the control S 14 expression) are presented as fold of increase in the graph below the panel. FIG. 2E is a table comparing the double immunofluorescence staining of T-cells from all the experimental groups described in FIG. 2D, using a mouse anti-67 kDa LR mAb (MLuC5) followed by an FITC-conjugated anti-human IgG, and phycoerythrin (PE)-conjugated anti-TCR mAb.

FIG. 3A compares the results of one representative experiment, presented as the number of T-cells (from one human donor), adhering to laminin (*p<0.01 vs. untreated). FIG. 3B represents the mean fold of increase ±SEM of T-cell adhesion to laminin of four independent experiments (using T-cells from 4 different donors). The degree of activation of laminin adhesion by phorbyl 12-myristate 13-acetate (PMA, 10 ng/ml) serves as positive control. The results show that both GnRH-I and GnRH-II induced T-cell adhesion to laminin as efficiently as PMA.

FIG. 3C shows the results of one representative experiment, presented as the number of fluorescently-labeled migrating T-cells (*p<0.01 vs. untreated). FIG. 3D represents the mean fold of increase.+−.SEM of four independent experiments (using T-cells from 4 individuals). The results show that both GnRH-II and GnRH-I can directly increase the migration potential of normal human T-cells towards the SDF-1 chemokine.

FIG. 4A compares the mean±SEM number of labeled T-cells that homed to the spleen of either GnRH-I deficient (KO) hpg or normal mice (N=4). *P<0.05. FIG. 4B compares the mean±SEM number of labeled T-cells that homed to the kidney of either GnRH-I deficient (KO) hpg or normal mice (N=4). *P<0.05. FIG. 4C compares the mean±SEM number of labeled T-cells that homed to the liver of either GnRH-I deficient (KO) hpg or normal mice (N=4). *P<0.05. FIG. 4D compares the mean±SEM number of labeled T-cells that homed to the thymus of either GnRH-I deficient (KO) hpg or normal mice (N=4). *P<0.05. FIG. 4E compares the mean±SEM number of labeled T-cells that homed to the bone marrow of either GnRH-I deficient (KO) hpg or normal mice (N=4). *P<0.05. FIG. 4F compares the mean±SEM number of labeled T-cells that were found in the plasma of either GnRH-I deficient (KO) hpg or normal mice (N=4). *P<0.05. Thus, the absence of GnRH-I impairs in vivo T-cell migration in an organ-specific manner.

FIG. 5A demonstrates the presence of amplified mouse 67 kDa LR (m67 kDa LR) and S16 (ribosomal protein) cDNA fragments from EL-4 cells after 1.5% o agarose gel electrophoresis and ethidium bromide staining, indicating that EL-4 lymphoma T-cells express the 67 kDa LR mRNA. FIG. 5B illustrates the double immunofluorescence staining for the 67 kDa LR (FITC, abscissa) and TCRαβ (PE ordinate) of EL-4 lymphoma cells treated with either GnRH-I or GnRH-II (10 nM). The upper two panels represent the plot of FACS separation of GnRH-I treated cells (plot II) compared to untreated cells (plot I), and the lower two panels represent GnRH-II treated cells (panel IV) compared to untreated cells (panel III). The results show an elevation in the 67 kDa LR+ and TCRαβ+ double positive expression in response to GnRH stimulation (framed windows). FIGS. 5C-5J illustrate the effect of direct stimulation of EL-4 T lymphoma with GnRH-I and GnRH-II (10 nM) on their subsequent in vivo entry into recipient mouse organs. FIGS. 5C and 5D represent the results of two separate experiments illustrating the enhanced migration of GnRH treated lymphoma cells into the bone marrow of normal recipient mice (*P<0.05). FIG. 5E illustrates the enhanced migration of GnRH treated lymphoma cells into the spleen of normal recipient mice (*P<0.05). FIGS. 5F-5I illustrate the absence of significant effect of GnRH treatment on migration of the EL-4 lymphoma cells into other organs. FIG. 5F illustrates the lack of effect of GnRH treatment on migration of lymphoma cells into the thymus of normal recipient mice (*P<0.05). FIG. 5G illustrates the lack of effect of GnRH treatment on migration of lymphoma cells into the kidney of normal recipient mice (*P<0.05). FIG. 5H illustrates the lack of effect of GnRH treatment on migration of lymphoma cells into the liver of normal recipient mice (*P<0.05). FIG. 5I illustrates the lack of effect of GnRH treatment on the number of lymphoma cells into the plasma of normal recipient mice (*P<0.05). Thus, GnRH stimulates lymphoma cell migration into recipient tissues in an organ-specific manner.

FIGS. 6A-6D illustrate the expression and organization of GnRH-II and GnRH-I genes in normal peripheral human T-cells and in Jurkat leukemic T-cells. FIG. 6A is a schematic representation of the GnRH-I (upper) and GnRH-II (lower) transcripts. GnRH-I and GnRH-II cDNA are shown with the introns (lines), exons (square) poly-A tail (wavy line) and location of the PCR fragments (shaded square). The length in base pairs of the introns, exons and each of the PCR fragments is indicated. FIG. 6B represents the identification by Southern blot hybridization of amplified GnRH-I, GnRH-II and the ribosomal protein S14 cDNA fragments, demonstrating the presence of GnRH I and II transcripts in human peripheral and Jurkat leukemic T-cells. Amplified GnRH-I, GnRH-II and S14 cDNA fragments from human peripheral human T-cells and Jurkat cells, were hybridized to a human GnRH-I (upper panel), GnRH-II (middle panel) and S14 (lower panel) $^{32}$P-labeled oligonucleotide probes. The hybridizations were performed sequentially on the same membrane. The predicted size of GnRH-I, GnRH-II and S14 fragments are 248 base pairs, 197 base pairs, and 143 base pairs, respectively. Lanes 1 and 4 represent PCR containing GnRH-I and S14 primers, while lanes 2 and 5 represent PCR containing GnRH-II and S14 primers. Lanes 3 and 6 represent PCR without added cDNA that served as negative control. FIGS. 6C and 6D represent the nucleotide sequence of the amplified GnRH-I (FIG. 6C, SEQ ID NO:2) and GnRH-II (FIG. 6D, SEQ ID NO:3) cDNA fragments. The 248 base pair product of FIG. 6B is identical to nucleotides 1134-1192 (exon 1) and 2063-3766 (exon 2 and 3) of human GnRH-I. The 197 base pair product of FIG. 6B is identical to nucleotides 1312-1355 (exon 1) and 2098-2250 (exon 2) of human GnRH-II. The location of the primers used in the PCR are underlined, and the location of the primers used as probes for hybridization are marked by squares.

FIG. 7A depicts the elution profile of GnRH-I and GnRH-II extracted from Jurkat T-cells and eluted through reverse phase (RP) HPLC. Fractions (1 ml) of the eluate were collected, evaporated and reconstituted with phosphate buffer. All fractions were assayed for GnRH-I and for GnRH-II by RIA, using specific antibodies for either GnRH-I (open columns) or GnRH-II (solid columns). The elution positions of synthetic GnRH-I (I) or GnRH-II (II) are indicated by open and black arrows, respectively. This figure demonstrates that Jurkat T-cells produce GnRH-I and GnRH-II having elution profiles identical to that of the synthetic peptides. The broken line indicates the acetonitrile gradient program. FIG. 7Bi-7Bviii depicts the double fluorescence microscopy of the normal peripheral human T cells, demonstrating the presence of immune-reactive GnRH-I and GnRH-II. The cells were incubated with a mixture of a monoclonal antibody against GnRH-I and a polyclonal anti-GnRH-II serum. A mixture of secondary antibodies, goat anti-mouse (Cy3, red fluorescence) and goat anti-rabbit (Oregon-Green, green fluorescence) were used to label the appropriate primary antibodies. FIGS. 7Biii and 7Bvii depict immunoreactive cells observed with the red filter (antibody against GnRH-I). FIGS. 7Biv and 7Bviii depict immunoreactive cells observed with the green filter (antibody against GnRH-II). FIGS. 7Bi and 7Bv are phase micrographs illustrating the general appearance of the culture. FIGS. 7Biv and 7Bviii demonstrate the absence of immunofluorescence in T-cells reacted with normal rabbit serum followed by the secondary antibodies. The arrows indicate immunoreactive clusters in the cell bodies.

FIG. 8A depicts the proposed cellular sources for GnRH-II and GnRH-I. T-cells migrating within fenestrated blood vessels, mainly in the brain, may encounter GnRH-II and GnRH-I released from nerve terminals (black arrows). In addition, normal human T-cells produce GnRH-II and GnRH-I, which may act either in an autocrine (represented by the left cell), and/or in a paracrine fashion on other T-cells (right cell) or other cell types. FIG. 8B depicts the direct effects of GnRH-II and GnRH-I on T-cells. Upon binding of GnRH-II and/or GnRH-I to their receptors, T-cells are activated, leading to the synthesis and surface expression of a 67 kDa non-integrin laminin receptor. FIG. 8C depicts the postulated physiological consequences of T-cell stimulation by GnRH. The GnRH-induced laminin receptor expression leads to T-cell adhesion to laminin within the endothelial basement membrane, a meshwork composed of several additional components among them collagen and proteoglycan (presented by the threads within the basement membrane). Of note, the basement membrane surrounding the endothelial cells normally prevents filtration of plasma proteins and cells into the tissues. The GnRH-stimulated T-cells, cells, in a laminin-binding mediated process, further extravasate across the blood vessel and basement membrane towards a chemokine secreted within a 'restful' or inflamed tissue. In the context of the present invention and the results presented in the Examples section herein, it is proposed that during desired T-cell migration and function, the effect of GnRH is beneficial and may be augmented, while in conditions of undesired T-cell migration, such as in T-cell mediated malignancies, autoimmune diseases (i.e. multiple sclerosis), graft-versus host disease, graft rejection etc., the direct effects of GnRH-II and GnRH-I on T-cells may be detrimental and should thus be inhibited

DESCRIPTION OF THE PREFERRED EMBODIMENTS

Figure 1A:
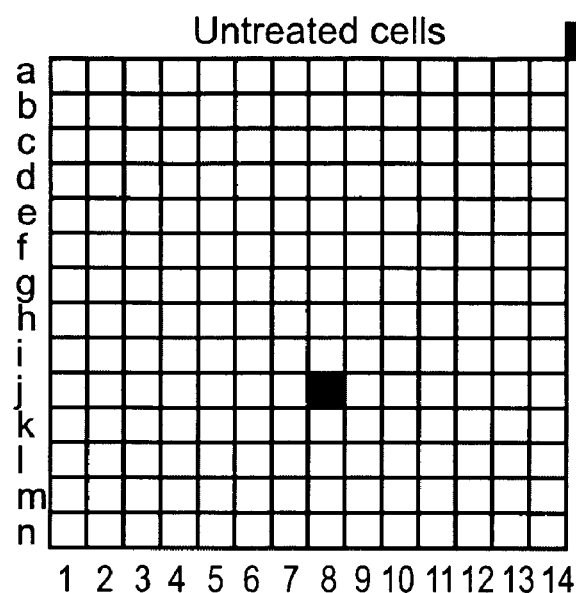
FIGS. 1A-C illustrate the activation of 67 kDa laminin receptor expression in mouse by GnRH-II, through analysis of gene expression using the atlas mouse cDNA expression array. $^{32}$P-labeled cDNA was prepared from poly A+ RNA, isolated from mouse antigen-specific T cells, treated with or without 10 nM of GnRH-II for 24 h. The cDNA was hybridized to the atlas membranes according to the manual, and expression was visualized by autoradiography (FIG. 1A, untreated cells.

The present invention is of methods and compositions for the modulation of T-cell activity by the action of specific neuropeptide receptor functional analogs and, more particularly, to methods for the treatment of bacterial, viral, fungal infectious and parasitic diseases, containment of auto-immune and other injurious inflammatory processes, inhibition and prevention of psychopathology, neoplastic, allergic and neurogenic diseases and conditions, and prevention of host rejection of engrafted tissue. Specifically, the present invention employs GnRH receptor-mediated regulation of laminin binding, via the modulation of the T-cell 67 kDa laminin receptor, to effect adhesion, extravasation and, ultimately regulate T-cell participation in inflammation and surveillance in infection and disease, as well as susceptibility of T-cells to infection. Similarly, inhibition of GnRH receptor-mediated extravasation is proposed for the limitation and prevention of metastatic spread of T-cell related and other cancerous conditions.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

At any given moment, T-cell populations throughout the body have to carry out a myriad of different activities, among them patrolling and surveillance, helping and suppressing, combating and killing. Moreover, T-cell activities must be precisely regulated and coordinated with many other cell types in general, and, perhaps most importantly, with dynamic neuro-endocrine networks. It is difficult to conceive that all these tasks are mediated solely via the 'classical' immunological interactions between the T-cell receptor (TCR), the principal receptor of these cells, and specific antigens, even if assisted by other immunological molecules, such as cytokines and chemokines and their receptors. In fact, the factors responsible for regulating T-cell activities within immune privileged environments, such as the brain, are still unknown and their discovery will certainly have important implications for the understanding and treatment of various T-cell mediated CNS pathologies, such as the autoimmune T-cell mediated multiple sclerosis.

Can T-cells respond directly to neuroendocrine molecules, despite the conceptual dogma of a 'language' barrier between effector molecules used for communication within the nervous, endocrine and immune systems? No doubt that such a direct mode of communication could be of great benefit for coordinating body functions in numerous physiological and pathophysiological conditions.

While reducing the present invention to practice, this question was addressed by investigating whether T-cells can be directly activated by the Gonadotropin releasing hormone-II (GnRH-II), a unique ten amino acid long neuropeptide, which has been conserved throughout 500 million years of evolution, and recently identified in the brain of various mammals. GnRH-II is 70% homologous in its peptide structure to the known mammalian neurohormone, GnRH (GnRH-I), but is encoded by its own gene. In contrast to GnRH-I, which is the prime regulator of reproduction, GnRH-II exerts only very mild effects on reproduction in mammals. The strict evolutionary conservation of GnRH-II, from primitive vertebrates to mammals, taken together with its unique functional profile, as compared to GnRH-I, suggests that GnRH-II has distinct, important physiological functions. The results presented herein show that indeed GnRH-II, as well as GnRH-I, drives normal human and mouse T-cells, in the absence of any additional stimuli, into de novo synthesis and surface expression of a specific receptor for laminin, the major glycoprotein component of endothelial and epithelial basement membranes. This is the first example of a neuropeptide that by itself, triggers T-cell gene expression.

As is illustrated in the Examples section which follows, experiments conducted by present inventor illustrated decreased entry of inoculated T-cells to the spleen and kidney in GnRH deficient (KO) mice, indicating a reduction in extravasation potential of normal T-cells in the absence of normal GnRH levels. Increasing the levels of the physiological neuropeptides utilized by the invention (GnRH-I and GnRH-II) induced T-cells to up-regulate the synthesis and expression of the 67 kDa laminin receptor, enhancing T-cell laminin adhesion, chemotactic migration and their entry into specific organs. Thus, under normal conditions, GnRH may lead to beneficial activation and extravasation of T-cells into resting, inflamed, injured or stressed tissues, and may serve for direct neuroendocrine coordination of immune function. Furthermore, under conditions of undesirable T-cell migration and function (autoimmune disease, chronic inflammation, allergic conditions, graft-versus-host disease and allograft rejection) GnRH may have detrimental effects and may be a target for immunosuppression.

In the context of the present invention, it is important to note that the 67 kDa laminin receptor is expressed in T-cell lymphoma and neoplastic cells, also functions as the receptor for Sindbis and tick-borne encephalitic viruses, and its 37 kDa precursor acts as the receptor for prion proteins. Thus, under neoplastic conditions upregulation of laminin receptor expression by GnRH may have undesirable effects, augmenting the migration, dissemination and metastasis of cancerous T-lymphocytes and other tumor cells across blood and tissue barriers, and increasing the susceptibility to viral and prion diseases.

While reducing the present invention to practice, it was also observed that GnRH stimulated overexpression of the 67 kDa laminin receptor in normal and lymphoma T-cells, and enhanced the entry of T-lymphoma cells into bone marrow and spleen of recipient mice. Thus, the neuropeptides of the present invention may be relevant targets for suppression of 67 kDa laminin receptor dependent tumor migration and metastasis, and for the prevention and treatment of specific viral and prion diseases.

It was further observed that normal human T-cells not only respond to the two forms of GnRH (I and II), but also produce them. Thus, the results presented herein reveal a novel mechanism by which the neuropeptides, GnRH-II or GnRH-I, can by themselves induce the synthesis, surface expression and related function of a major adhesion receptor, and directly affect T-cell migration in vivo and entry into specific organs.

Further, in the context of the present invention, it is important to note the role of immune function in general, and T-cells in particular, in neuroprotective immunity. Activated T-cells in sufficient numbers, at crucial locations in the CNS, and with appropriate temporal coordination, are necessary for optimal healing following neuronal injury or viral infection of the CNS (Yoles E et al J Neurosci 2000; 21: 3740-8; and Binder G K and Griffen D E Science 2001; 293: 303-6). Thus, the compositions and methods of the present invention can be used for treatment and prevention of neuronal damage in CNS injury and infection.

Thus, according to one aspect of the present invention there is provided a method of regulating activity of a T-cell population, the method comprising providing to the T-cell population a molecule selected as being capable of modifying an activity or expression level of a GnRH-I or a GnRH-II receptor thereby regulating GnRH-I or GnRH-II mediated activity of a T-cell population.

In one embodiment of the invention, the molecule selected as being capable of modifying an activity or expression level of a GnRH-I or GnRH-II receptor is an upregulating molecule causing increased T-cell activity. In another embodiment of the invention, the molecule selected as being capable of modifying an activity or expression level of a GnRH-I or GnRH-II receptor is an downregulating molecule causing increased T-cell activity.

As used herein, the term "expression level . . . of a receptor" is defined at the availability of receptor mRNA transcripts for receptor protein synthesis within the cell, being either of endogenous receptor gene origin, or originating from transcription of exogenous polynucleotide sequences encoding a GnRH-I or GnRH-II receptor. In the context of the present invention, increased "expression level" is defined as levels resulting in increased numbers of functional GnRH-I or GnRH-II receptor molecules on the cell surface, providing greater potential to respond to GnRH-I, GnRH-II, or GnRH-I or GnRH-II analog stimulation. Likewise, decreased "expression level" results in reduced numbers of functional receptors, and impaired potential for response.

The upregulating molecule can be, for example, an upregulating GnRH-I or GnRH-II analog, GnRH-I or GnRH-II, an upregulating anti-GnRH-I or GnRH-II receptor antibody, or an expressible polynucleotide encoding a GnRH-I or GnRH-II receptor. The upregulating GnRH-I or GnRH-II analog may be a naturally occurring, synthetic, decapeptide and/or peptide fragment analog. In a preferred embodiment, the upregulating analog is a decapeptide having a sequence as set forth in any of SEQ ID NOs: 4-29.

Similarly, the downregulating molecule can be, for example, a downregulating GnRH-I or GnRH-II analog.

As used herein, the term "GnRH analog" refers to a peptide or peptides of substantial sequence identity to the complete or partial amino acid sequence of Gonadotropin Releasing Hormone, also known as Leutinizing Hormone Releasing Hormone (LHRH). The following table Table 1 presents the amino acid sequences of GnRH analogs, compared with the amino acid sequence of mammalian GnRH-I.

TABLE 1

Comparison of known GnRH amino acid sequences with Human GnRH-I

| Form of GnRH (SEQ ID NO:) | Amino acids |
| --- | --- |
| Mammalian (GnRH-I) (4) | pGlu-His-Trp-Ser-Tyr-Gly-Leu-Arg-Pro-Gly-NH$_2$ |
| Guinea pig (gpGnRH) (5) | pGlu-Tyr-Trp-Ser-Tyr-Gly-Val-Arg-Pro-Gly-NH$_2$ |
| Sea bream (sbGnRH) (6) | pGlu-His-Trp-Ser-Tyr-Gly-Leu-Ser-Pro-Gly-NH$_2$ |
| Pejerrey (pjGnRH) (7) | pGlu-His-Trp-Ser-Phe-Gly-Leu-Ser-Pro-Gly-NH$_2$ |
| Herring (hrGnRH) (8) | pGlu-His-Trp-Ser-His-Gly-Leu-Ser-Pro-Gly-NH$_2$ |
| Catfish (cfGnRH) (9) | pGlu-His-Trp-Ser-His-Gly-Leu-Asn-Pro-Gly-NH$_2$ |
| Chicken I (cGnRH-I) (10) | pGlu-His-Trp-Ser-Tyr-Gly-Leu-Gln-Pro-Gly-NH$_2$ |
| Salmon (sGnRH) (11) | pGlu-His-Trp-Ser-Tyr-Gly-Trp-Leu-Pro-Gly-NH$_2$ |
| Chicken II (cGnRH-II) (12) | pGlu-His-Trp-Ser-His-Gly-Trp-Tyr-Pro-Gly-NH$_2$ |
| Dogfish (dfGnRH) (13) | pGlu-His-Trp-Ser-His-Gly-Trp-Leu-Pro-Gly-NH$_2$ |
| Lamprey (lGnRH-III) (14) | pGlu-His-Trp-Ser-His-Asp-Trp-Lys-Pro-Gly-NH$_2$ |
| Lamprey (lGnRH-III) (15) | pGlu-His-Tyr-Ser-Leu-Glu-Trp-Lys-Pro-Gly-NH$_2$ |
| Tunicate (tGnRH-II) (16) | pGlu-His-Trp-Ser-Asp-Tyr-Phe-Lys-Pro-Gly-NH$_2$ |
| Tunicate (tGnRH-II) (17) | pGlu-His-Trp-Ser-Leu-Cys-His-Ala-Pro-Gly-NH$_2$ |

The following provides a list of additional GnRH analogs having a known amino acid sequence identified by their GenBank (NCBI) accession numbers and source: P81749 (GnRH-I *Culpea pallasi* (pacific herring)) (SEQ ID NO:18); RHLMGS (GnRH-II *Petromyzon marinus* (sea lamprey)) (SEQ ID NO:19); B46030 (GnRH-II *Squalus acanthias* (spiny dogfish)) (SEQ ID NO:20); A46030 (GnRH-I *Squalus acanthias* (spiny dogfish)) (SEQ ID NO:21); P80677 (GnRH-I *Chelyosoma productum*) (SEQ ID NO:22); P30948 (GnRH-III *Petromyzon marinus* (sea lamprey)) (SEQ ID NO:23); P04378 (GnRH-I *Petromyzon marinus* (sea lamprey)) (SEQ ID NO:24); P27429 (GnRH-I *Squalus acanthias* (spiny dogfish)) (SEQ ID NO:25); AAB34379 (GnRH-I *Acipenser gueldenstaedtii* (Russian sturgeon)) (SEQ ID NO:26); AAB23160 (GnRH-II *Clarias gariepinus* (african catfish)) (SEQ ID NO:27); P20367 (GnRH-III *Culpea pallasi* (Pacific herring)) (SEQ ID NO:28); P37043 (GnRH-II *Culpea pallasi* (Pacific herring)) (SEQ ID NO:29).

In addition to the abovementioned GnRH analogs, many analogs bearing amino acid sequence modifications are available to one skilled in the art (see, for example BACHEM Catalog, BACHEM AG, Switzerland). For example, analogs inhibiting GnRH activity have been synthesized with substitutions of unnatural amino acids in the 3, 5, 6 and/or 8 positions (pGlu-His-Xaa-Ser-Xaa-Xaa-Leu-Xaa-Pro-Gly-NH$_2$) (SEQ ID NO:30) as in U.S. Pat. No. 5,744,450 to Hoeger, et al, and in the 5, 6, 8 and 10 positions (pGlu-His-Trp-Ser-Xaa-Xaa-Leu-Xaa-Gly-Xaa-NH$_2$)(SEQ ID NO:31) as in U.S. Pat. No. 5,925,730 to Semple, et al. In addition, non-peptide GnRH antagonists have been developed: for example, the indole derivatives disclosed in U.S. Pat. No. 6,025,366 to Walsh, et al; U.S. Pat. No. 6,077,858 to Goulet, et al; and U.S. Pat. No. 6,211,224 to Chu et al.

As used herein, the term "substantial identity" means that two peptide sequences, when optimally aligned, such as by the programs BLAZE (Intelligenetics) GAP or BESTFIT using default gap weights, share at least 70 percent or 80 percent sequence identity, preferably at least 90 percent sequence identity, more preferably at least 95 percent sequence identity or more (e.g., 99 percent sequence identity).

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein the term "peptide" includes native peptides (either degradation products, synthetically synthesized peptides or recombinant peptides) and peptido-mimetics (typically, synthetically synthesized peptides), such as peptoids and semipeptoids which are peptide analogs, which may have, for example, modifications rendering the peptides more stable while in a body. Such modifications include, but are not limited to, cyclization, N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptido-mimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further detail in this respect are provided hereinunder.

Thus, a peptide according to the present invention can be a cyclic peptide. Cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2$)$_n$—COOH)—C(R)H—COOH or H—N(($CH_2$)$_n$—COOH)—C(R)H—$NH_2$, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—$CH_2$—)$_n$—S—$CH_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

Tables 2 and 3 below list all the naturally occurring amino acids (Table 2) and non-conventional or modified amino acids (Table 3).

TABLE 2

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 3

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |

TABLE 3-continued

| Non-conventional amino acid | Code | Non-conventional amino acid | Code |
|---|---|---|---|
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmtyr | N-cyclodecylglycine | Ncdec |
| D-α-methylvaline | Dmval | N-cyclododecylglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylaminoisobutyrate | Nmaib | D-N-methylphenylalanine | Dnmphe |
| N-(1-methylpropyl)glycine | Nile | D-N-methylproline | Dnmpro |
| N-(2-methylpropyl)glycine | Nleu | D-N-methylserine | Dnmser |
| D-N-methyltryptophan | Dnmtrp | D-N-methylthreonine | Dnmthr |
| D-N-methyltyrosine | Dnmtyr | N-(1-methylethyl)glycine | Nval |
| D-N-methylvaline | Dnmval | N-methyl-α-napthylalanine | Nmanap |
| γ-aminobutyric acid | Gabu | N-methylpenicillamine | Nmpen |
| L-t-butylglycine | Tbug | N-(p-hydroxyphenyl)glycine | Nhtyr |
| L-ethylglycine | Etg | N-(thiomethyl)glycine | Ncys |
| L-homophenylalanine | Hphe | Penicillamine | Pen |
| L-α-methylarginine | Marg | L-α-methylalanine | Mala |
| L-α-methylaspartate | Masp | L-α-methylasparagine | Masn |
| L-α-methylcysteine | Mcys | L-α-methyl-t-butylglycine | Mtbug |
| L-α-methylglutamine | Mgln | L-methylethylglycine | Metg |
| L-α-methylhistidine | Mhis | L-α-methylglutamate | Mglu |
| D-N-methylglutamine | Dnmgln | L-α-methylhomo phenylalanine | Mhphe |
| D-N-methylglutamate | Dnmglu | N-(2-methylthioethyl)glycine | Nmet |
| D-N-methylhistidine | Dnmhis | N-(3-guanidinopropyl)glycine | Narg |
| D-N-methylisoleucine | Dnmile | N-(1-hydroxyethyl)glycine | Nthr |
| L-α-methylleucine | Mleu | N-(hydroxyethyl)glycine | Nser |
| L-α-methylmethionine | Mmet | N-(imidazolylethyl)glycine | Nhis |
| L-α-methylnorvaline | Mnva | L-α-methyllysine | Mlys |
| L-α-methylphenylalanine | Mphe | L-α-methylnorleucine | Mnle |
| L-α-methylserine | Mser | L-α-methylornithine | Morn |
| L-α-methylvaline | Mval | L-α-methylproline | Mpro |
| L-α-methytryptophan | Mtrp | L-α-methylthreonine | Mthr |
| N-(N-(2,2-diphenylethyl) carbamylmethyl-glycine | Nnbhm | L-α-methyltyrosine | Mtyr |
| 1-carboxy-1-(2,2-diphenyl ethylamino)cyclopropane | Nmbc | L-N-methylhomophenylalanine | Nmhphe |
| | | N-(N-(3,3-diphenylpropyl) carbamylmethyl(1)glycine | Nnbhe |

A peptide according to the present invention can be used in a self standing form or be a part of moieties such as proteins and display moieties such as display bacteria and phages. The peptides of the invention can also be chemically modified to give active dimers or multimers, in one polypeptide chain or covalently crosslinked chains.

Additionally, a peptide according to the present invention includes at least two, optionally at least three, optionally at least four, optionally at least five, optionally at least six, optionally at least seven, optionally at least eight, optionally at least nine, optionally at least ten or more amino acid residues (also referred to herein interchangeably as amino acids).

Accordingly, as used herein the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Cell surface receptors may be targeted by specific antibodies, binding to epitopes exposed to the cellular environment. Although these antibodies may block ligand-receptor interaction, in binding some may also activate signal transduction pathways, behaving as agonists: this is commonly seen in autoimmune disease, such as Graves disease (for example, see Grando, S A. Antireceptor activity in pemphigus. Dermatology 2000; 201(4) 290-295; and Mijares, A., Lebesque, D., Walluk G. and Hoebeke, J. From agonist to antagonist. Mol. Pharmacol. 2000 August 58 (2): 373-378). Similarly, specific antibodies directed against T-cell GnRh-I or GnRH-II receptors may act as agonists, stimulating T-cell activity.

Thus, in one embodiment of the present invention the molecule selected as being capable of modifying an activity or expression level of a GnRH-I or GnRH-II receptor is an upregulating or downregulating anti-GnRh-I or GnRH-II receptor antibody. T-cells may be exposed to the antibody in vivo or isolated from the organism and exposed ex vivo (for methods of modification of T-cell activity in vitro see, for example, the in-vitro assay of T-cell adhesion to laminin described in Materials and Methods section below, assays of cytokine secretion described in Levite, M. et al, J Exp Med 2000, 191, 1167-76, and the ex vivo methods of Wank, et al described hereinbelow).

As is used herein, the term "antibody" refers to either a polyclonal or monoclonal antibody, recognizing at least one epitope of a GnRH-I or GnRH-II receptor. The present invention can utilize serum immunoglobulins, polyclonal antibodies or fragments thereof, (i.e., immunoreactive derivative of an antibody), or monoclonal antibodies or fragments thereof.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., Proc. Nat'l Acad. Sci. USA 69: 2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242: 423-426, 1988; Pack et al., Bio/Technology 11: 1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (0.1986); Riechmann et al., Nature, 332: 323-329 (1988); and Presta, Curr. Op. Struct. Biol., 2: 593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321: 522-525 (1986); Riechmann et al., Nature 332: 323-327 (1988); Verhoeyen et al., Science, 239: 1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227: 381 (1991); Marks et al., J. Mol. Biol., 222: 581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1): 86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13, 65-93 (1995).

In a preferred embodiment of the present invention, the anti-GnRH-I antibody is a specific polyclonal antibody prepared against synthetic human GnRH-I (Koch et al. Biochem Biophys Res Commun 1973; 55: 616-622). In another embodiment, anti-GnRH-I is a monoclonal antibody HU4H specific to GnRH-I (Urbanski, H. F. et al. Endocrinology 1999. 140: 1945-48). In one embodiment of the present invention, anti-GnRH-II may be the specific polyclonal anti-GnRH-II antibody aCII6 (Okuzowa, K et al. Gen Comp Endocrinol 1990; 80: 116-2.6) or specific anti-GnRH-II antisera KLII-2 (Cohen et al. Nature 2001).

Intracellular levels of GnRH-I or GnRH-II signal transducers may be manipulated by increasing or decreasing the abundance of GnRH-I or GnRH-II receptor transcripts available for protein synthesis. This may be accomplished by introducing into target cells expressible polynucleotides upregulating or downregulating GnRH-I or GnRH-II receptor expression. Delivery of such polynucleotides may be by injection, introduction into the circulation, or introduction into the body cavities by inhalation or insufflation. The expressible polynucleotides may be DNA or RNA sequences encoding a GnRH-I or GnRH-II receptor molecule, capable of enhancing GnRH-I or GnRH-II stimulation of target cells. Expression may be transient and reversible, or the polynucleotide may become integrated into the host genome, producing stable expression of the therapeutic polynucleotide. For illustrative methodology relating to the introduction of DNA and RNA sequences into host cells, see, for example, U.S. Pat. Nos. 5,589,466 and 6,214,806, both to Feigner et al.

Thus, according to one aspect of the present invention there is provided a method of upregulating T-cell activity in a T cell population or a mammalian subject, the method effected by introducing into the cells an expressible polynucleotide encoding a GnRH-I or GnRH-II receptor, the expressible polynucleotide designed so as to be capable of enhancing GnRH-I or GnRH-II receptor expression in said T-cells, thereby upregulating T-cell activity within cells of the T-cell population or mammalian subject. The expressible polynucleotides may contain sequences representing coding sequences of GnRH-I or GnRH-II and GnRH-I or GnRH-II upregulating analogs. The expressible polynucleotides may contain sequences as set forth in SEQ ID NOs: 2, 3, 33 and 34, and at least 60%, preferably at least 70%, more preferably at least 80%, more preferably at least 90% and most preferably about 100% homologous to any of SEQ ID NOs: 2 and 3. The expressible polynucleotides may also contain sequences representing sequences of GnRH-I or GnRH-II receptor polypeptides, at least 60%, preferably at least 70%, more preferably at least 80%, more preferably at least 90% and most preferably about 100% homologous to SEQ ID NO: 37. Methods for transformation of T-cells with expressible polynucleotides are described in detail hereinbelow.

Further according to the present invention, there is provided a method of downregulating T-cell activity in a T cell population or a mammalian subject. One preferred method of downregulating T-cell activity or an expression of a gene encoding a GnRH-I or GnRH-II receptor in a T-cell population or in a mammalian subject is effected by providing to the T-cells polynucleotides designed having specific GnRH-I or GnRH-II receptor transcript cleaving or binding capability thereby downregulating GnRH-I or GnRH-II receptor production, effectively reducing sensitivity to GnRH-I or GnRH- II activation. The polynucleotides may be ribozymes having specific GnRH-I or GnRH-II receptor transcript cleaving capabilities, or antisense nucleotide sequences complementary to and capable of reducing GnRH-I or GnRH-II receptor expression. Similarly, expressible polynucleotides encoding ribozymes or antisense transcripts can be used. These polynucleotide sequences may be introduced into the subject's T-cells and other tissues in vivo or into an ex vivo population of T-cells, by methods of RNA and DNA transfer commonly known in the art such as calcium precipitation, electroporation, microparticle delivery and the like, and readministered to the subject. The preparation and use of such antisense and ribozyme polynucleotides is detailed hereinbelow.

An antisense polynucleotide (e.g., antisense oligodeoxyribonucleotide) may bind its target nucleic acid either by Watson-Crick base pairing or Hoogsteen and anti-Hoogsteen base pairing (Thuong and Helene (1993) Sequence specific recognition and modification of double helical DNA by oligonucleotides Angev. Chem. Int. Ed. Engl. 32: 666). According to the Watson-Crick base pairing, heterocyclic bases of the antisense polynucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triple helix structure.

According to both the Watson-Crick and the Hoogsteen base pairing models, antisense oligonucleotides have the potential to regulate gene expression and to disrupt the essential functions of the nucleic acids in cells. Therefore, antisense polynucleotides have possible uses in modulating a wide range of diseases in which gene expression is altered.

Since the development of effective methods for chemically synthesizing polynucleotides, these molecules have been extensively used in biochemistry and biological research and have the potential use in medicine, since carefully devised polynucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, the regulation of transcription or translation levels.

Gene expression involves few distinct and well regulated steps. The first major step of gene expression involves transcription of a messenger RNA (mRNA) which is an RNA sequence complementary to the antisense (i.e., –) DNA strand, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the mRNA interacts with ribosomal RNA complexes (ribosomes) and amino acid activated transfer RNAs (tRNAs) to direct the synthesis of the protein coded for by the mRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more transcription factors to the promoter sequence. Additional proteins which bind at or close to the promoter sequence may trans upregulate transcription via cis elements known as enhancer sequences. Other proteins which bind to or close to the promoter, but whose binding prohibits the action of RNA polymerase, are known as repressors.

There is also evidence that in some cases gene expression is downregulated by endogenous antisense RNA repressors that bind a complementary mRNA transcript and thereby prevent its translation into a functional protein.

Thus, gene expression is typically upregulated by transcription factors and enhancers and downregulated by repressors.

However, in many disease situations gene expression is impaired. In many cases, such as different types of cancer, for various reasons the expression of a specific endogenous or exogenous (e.g., of a pathogen such as a virus) gene is upregulated.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription (Thuong and Helene (1993) Sequence specific recognition and modification of double helical DNA by oligonucleotides Angev. Chem. Int. Ed. Engl. 32: 666).

At the transcript level, antisense oligonucleotides or analogs that bind target mRNA molecules lead to the enzymatic cleavage of the hybrid by intracellular RNase hours (Dash P., Lotan I., Knapp M., Kandel E. R. and Goelet P. (1987) Selective elimination of mRNAs in vivo: complementary oligodeoxynucleotides promote RNA degradation by an RNase H-like activity. Proc. Natl. Acad. Sci. USA, 84: 7896). In this case, by hybridizing to the targeted mRNA, the oligonucleotides or oligonucleotide analogs provide a duplex hybrid recognized and destroyed by the RNase hours enzyme. Alternatively, such hybrid formation may lead to interference with correct splicing (Chiang M. Y., Chan H., Zounes M. A., Freier S. M., Lima W. F. and Bennett C. F. (1991) Antisense oligonucleotides inhibit intercellular adhesion molecule I expression by two distinct mechanisms. J. Biol. Chem. 266: 18162-71). As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool.

For example, several antisense oligonucleotides have been shown to arrest hematopoietic cell proliferation (Szczylik et al. (1991) Selective inhibition of leukemia cell proliferation by BCR-ABL antisense oligodeoxynucleotides. Science 253: 562.), growth (Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88: 2351), entry into the S phase of the cell cycle (Heikhila et al. (1987) A c-myc antisense oligodeoxynucleotide inhibits entry into S phase but not progress from G(0) to G(1). Nature, 328: 445), reduced survival (Reed et al. (1990) Antisense mediated inhibition of BCL2 prooncogene expression and leukemic cell growth and survival: comparison of phosphodiester and phosphorothioate oligodeoxynucleotides. Cancer Res. 50: 6565), prevent receptor mediated responses (Burch and Mahan (1991) Oligodeoxynucleotides antisense to the interleukin I receptor m RNA block the effects of interleukin I in cultured murine and human fibroblasts and in mice. J. Clin. Invest. 88: 1190) and as antiviral agents (Agrawal (1992) Antisense oligonucleotides as antiviral agents. TIBTECH 10: 152).

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetrators.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives. For illustrative examples and further details see Cook (1991) Medicinal chemistry of antisense oligonucleotides—future opportunities. Anti-Cancer Drug Design 6: 585.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—). However, the application provides no data supporting the specific binding of an oligonucleotide analog to a target oligonucleotide.

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal.

Thus, antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases. Antisense polynucleotides are typically synthesized in lengths of 13-30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials. A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dozens of other nucleotide analogs have also been tested in antisense technology.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target a mRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

Antisense therapy has also been applied to immune disorders and inhibition of cell migration. For example, U.S. Pat. No. 6,096,722 to Bennet et al. discloses the application of antisense polynucleotides to interrupt cell adhesion molecules (CAM) expression in the treatment of pathogenic, autoimmune, allergic, chronic inflammatory, hyperproliferation and metastatic conditions. International Application No. WO 97/39721 to Glimcher et al discloses the use of antisense polynucleotides to T-cell activation and cytokine expression.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Another approach is the use of specific nucleic acid sequences to act as decoys for transcription factors. Since transcription factors bind specific DNA sequences it is possible to synthesize oligonucleotides that will effectively compete with the native DNA sequences for available transcription factors in vivo. This approach requires the identification of gene specific transcription factor.

Indirect inhibition of gene expression was demonstrated for matrix metalloproteinase genes (MMP-1, -3, and -9), which are associated with invasive potential of human cancer cells. E1AF is a transcription activator of MMP genes. Expression of E1AF antisense RNA in HSC3AS cells showed decrease in mRNA and protein levels of MMP-1, -3, and -9. Moreover, HSC3AS showed lower invasive potential in vitro and in vivo. These results imply that transfection of antisense inhibits tumor invasion by down-regulating MMP genes.

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. Two "types" of ribozymes are particularly useful in this invention, the hammerhead ribozyme (Rossi, J. J. et al., Pharmac. Ther. 50: 245-254, 1991) and the hairpin ribozyme (Hampel et al., Nucl. Acids Res. 18: 299-304, 1990, and U.S. Pat. No. 5,254,678, issued Oct. 19, 1993). Because both hammerhead and hairpin ribozymes are catalytic molecules having antisense and endoribonucleotidase activity, ribozyme technology has emerged as a potentially powerful extension of the antisense approach to gene inactivation. The ribozymes of the invention typically consist of RNA, but such ribozymes may also be composed of nucleic acid molecules comprising chimeric nucleic acid sequences (such as DNA/RNA sequences) and/or nucleic acid analogs (e.g., phosphorothioates).

Ribozymes may be in the form of a "hammerhead" (for example, as described by Forster and Symons, Cell 48: 211-220, 1987; Haseloff and Gerlach, Nature 328: 596-600, 1988; Walbot and Bruening, Nature 334: 196, 1988; Haseloff and Gerlach, Nature 334: 585, 1988) or a "hairpin" (for example, as described by Haseloff et al., U.S. Pat. No. 5,254,678, issued Oct. 19, 1993 and Hempel et al., European Patent Publication No. 0 360 257, published Mar. 26, 1990). The sequence requirement for the hairpin ribozyme is any RNA sequence consisting of NNNBN*GUCNNNNNN (where N*G is the cleavage site, where B is any of G, C, or U, and where N is any of G, U, C, or A)(SEQ ID NO: 32). The sequence requirement at the cleavage site for the hammerhead ribozyme is any RNA sequence consisting of NUX (where N is any of G, U, C, or A and X represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al., Biochemistry 29: 10695-10702, 1990).

This information, and the published sequence of mRNA coding sequences for human GnRH-II (Genbank accession number AF36329; White, R B et al.) (SEQ ID NO:33), human GnRH-I (Genbank accession number X15215; Hayflick et al.) (SEQ ID NO:34), and the sequences for human GnRH-I mRNA (Genbank accession number NM000825; Seeburg et al) (SEQ ID NO:35), GnRH-II mRNA (Genbank accession number NM001501; White, et al) (SEQ ID NO:36) and human GnRH receptor mRNA (Genebank accession number NM 000406; Kakar, et al) (SEQ ID NO: 37), together with the cDNA sequences for GnRH-I and GnRH-II disclosed in FIGS. 6C and 6D (SEQ ID NOs:2 and 3) enables the production of the ribozymes of this invention. Appropriate base changes in the ribozyme is made to maintain the necessary base pairing with the target RNA sequences.

Cech et al. (U.S. Pat. No. 4,987,071) has disclosed the preparation and use of certain synthetic ribozymes which have endoribonuclease activity. These ribozymes are based on the properties of the Tetrahymena ribosomal RNA self-splicing reaction and require an eight base pair target site. The ribozymes of this invention, as well as DNA encoding such ribozymes and other suitable nucleic acid molecules, can be chemically synthesized using methods well known in the art for the synthesis of nucleic acid molecules. Alternatively, Promega, Madison, Wis., USA, provides a series of protocols suitable for the production of RNA molecules such as ribozymes. The ribozymes also can be prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Such a construct may be referred to as a vector. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation 15 with the RNA polymerase and appropriate nucleotides. Alternatively, the DNA may be inserted into an expression cassette, such as described in Cotten and Birnstiel, EMBO J. 8(12): 3861-3866, 1989, and in Hempel et al., Biochemistry 28: 4929-4933, 1989. A more detailed discussion of molecular biology methodology is disclosed in Sambrook et al., Molecular Cloning: A Laboratory Manual, Cold Spring Harbor Press, 1989.

After synthesis, the ribozyme can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

In one preferred embodiment of the present invention, the expressible downregulating polynucleotide is designed so as to be capable of transient expression in cells of the subject. In another preferred embodiment, the expressible polynucleotide is designed so as to be capable of stably integrating into the genome of cells of the subject.

Thus, the ribozyme molecule also can be in a host procaryotic or eukaryotic cell in culture or in the cells of an organism. Appropriate prokaryotic and eukaryotic cells can be transfected with an appropriate transfer vector containing the DNA molecule encoding a ribozyme of this invention. Alternatively, the ribozyme molecule, including nucleic acid molecules encoding the ribozyme, may be introduced into the host cell using traditional methods such as transformation using calcium phosphate precipitation (Dubensky et al., PNAS 81: 7529-7533, 1984), direct microinjection of such nucleic acid molecules into intact target cells (Acsadi et al., Nature 352: 815-818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., PNAS 89: 6094, 1990), lipofection (Felgner et al., Proc. Natl. Acad. Sci. USA 84: 7413-7417, 1989), microprojectile bombardment (Williams et al., PNAS 88: 2726-2730, 1991), polycation compounds such as polylysine, receptor specific ligands, liposomes entrapping the nucleic acid molecules, spheroplast fusion whereby E coli containing the nucleic acid molecules are stripped of their outer cell walls and fused to animal cells using polyethylene glycol, viral transduction, (Cline et al., Pharmac. Ther. 29: 69, 1985; and Friedmann et al., Science 244: 1275, 1989), and DNA ligand (Wu et al. J. of Biol. Chem. 264: 16985-16987, 1989), as well as psoralen inactivated viruses such as Sendai or Adenovirus. In a preferred embodiment, the ribozyme is introduced into the host cell utilizing a liposome.

When the DNA molecule is operatively linked to a promoter for RNA transcription, the RNA can be produced in the host cell when the host cell is grown under suitable conditions favoring transcription of the DNA molecule. The vector can be, but is not limited to a plasmid, a virus, a retrotransposon or a cosmid. Examples of such vectors are disclosed in U.S. Pat. No. 5,166,320. Other representative vectors include adenoviral vectors (e.g., WO 94/26914, WO 93/9191; Kolls et al., PNAS 91(1): 215-219, 1994; Kass-Eisler et al., PNAS 90(24): 11498-502, 1993; Guzman et al., Circulation 88(6): 2838-48, 1993; Guzman et al., Cir. Res. 73(6): 1202-1207, 1993; Zabner et al., Cell 75(2): 207-216, 1993; Li et al., Huim Gene Ther. 4(4): 403-409, 1993; Caillaud et al., Eur. J. Neurosci. 5(10): 1287-1291, 1993), adeno-associated vector type 1 ("AAV-1") or adeno-associated vector type 2 ("AAV-2") (see WO 95/13365; Flotte et al., PNAS 90(22): 10613-10617, 1993), retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218) and herpes viral vectors (e.g., U.S. Pat. No. 5,288,641). Methods of utilizing such vectors in gene therapy are well known in the art, see, for example, Larrick, J. W. and Burck, K. L., Gene Therapy: Application of Molecular Biology, Elsevier Science Publishing Co., Inc., New York, N.Y., 1991 and Kreigler, M., Gene Transfer and Expression: A Laboratory Manual, W.H. Freeman and Company, New York, 1990. To produce ribozymes in vivo utilizing vectors, the nucleotide sequences coding for ribozymes are preferably placed under the control of a strong promoter such as the lac, SV40 late, SV40 early, or lambda promoters. Ribozymes are then produced directly from the transfer vector in vivo.

Observations in the early 1990s that plasmid DNA could directly transfect animal cells in vivo sparked exploration of the use of DNA plasmids to induce immune response by direct injection into animal of DNA encoding antigenic protein. When a DNA vaccine plasmid enters the eukaryotic cell, the protein it encodes is transcribed and translated within the cell. In the case of pathogens, these proteins are presented to the immune system in their native form, mimicking the presentation of antigens during a natural infection. DNA vaccination is particularly useful for the induction of T cell activation. It was applied for viral and bacterial infectious diseases, as well as for allergy and for cancer. The central hypothesis behind active specific immunotherapy for cancer is that tumor cells express unique antigens that should stimulate the immune system. The first DNA vaccine against tumor was carcino-embrionic antigen (CEA). DNA vaccinated animals expressed immunoprotection and immunotherapy of human CEA-expressing syngeneic mouse colon and breast carcinoma. In a mouse model of neuroblastoma, DNA immunization with HuD resulted in tumor growth inhibition with no neurological disease. Immunity to the brown locus protein, $gp^{75}$ tyrosinase-related protein-1, associated with melanoma, was investigated in a syngeneic mouse model. Priming with human gp75 DNA broke tolerance to mouse gp75. Immunity against mouse gp75 provided significant tumor protection.

The present invention has the potential to provide transgenic gene and polymorphic gene animal and cellular (cell lines) models as well as for knockout models. These models may be constructed using standard methods known in the art and as set forth in U.S. Pat. Nos. 5,487,992, 5,464,764, 5,387, 742, 5,360,735, 5,347,075, 5,298,422, 5,288,846, 5,221,778, 5,175,385, 5,175,384, 5,175,383, 4,736,866 as well as Burke and Olson, Methods in Enzymology, 194: 251-270 1991); Capecchi, Science 244: 1288-1292 1989); Davies et al., Nucleic Acids Research, 20 (11) 2693-2698 1992); Dickinson et al., Human Molecular Genetics, 2(8): 1299-1302 1993); Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9: 742-750 1991); Jakobovits et al., Nature, 362: 255-261 1993); Lamb et al., Nature Genetics, 5: 22-29 1993); Pearson and Choi, Proc. Natl. Acad. Sci. USA 1993). 90: 10578-82; Rothstein, Methods in Enzymology, 194: 281-301 1991); Schedl et al., Nature, 362: 258-261 1993); Strauss et al., Science, 259: 1904-1907 1993). Further, patent applications WO 94/23049, WO93/14200, WO 94/06908, WO 94/28123 also provide information.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is, within the recipient. In an alternative embodiment, if the host gene is defective, the gene is repaired in situ (Culver, 1998. (Abstract) Antisense DNA & RNA based therapeutics, February 1998, Coronado, Calif.). These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any nontranslated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York 1989, 1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et al. (Biotechniques 4 (6): 504-512, 1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral utilizes its natural specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with appropriate target specificity for infection.

Antisense, ribozyme and DNA therapy may be targeted to the GnRH-I or GnRH-II receptor, effectively reducing the ability of the treated T-cells to respond to stimulation by GnRH-I or GnRH-II, or GnRH-I or GnRH-II agonistic analogs. For example, Baserga et al. (U.S. Pat. No. 6,274,562) discloses the application of antisense constructs against IGF-I receptor transcripts to inhibit proliferation and cause differentiation of the IGF-I sensitive cells. Schreiber et al. (U.S. Pat. No. 6,242,427) disclose antisense constructs for treatment of inflammatory conditions by inhibiting Fc receptor expression in phagocytic cells. Similarly, U.S. Pat. No. 5,622,854 to Draper discloses, in detail, methods for the transformation of T-cells with expressible polynucleotides.

The molecules of the present invention can also include small interfering duplex oligonucleotides [i.e., small interfering RNA (siRNA)], which direct sequence specific degradation of mRNA through the previously described mechanism of RNA interference (RNAi) [Hutvagner and Zamore (2002) Curr. Opin. Genetics and Development 12: 225-232].

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Instructions for generation of duplex oligonucleotides capable of mediating RNA interference are provided in www.ambion.com.

In one preferred embodiment, the ribozyme, antisense or siRNA polynucleotides are directed against GnRH-I or GnRH-II receptors. Thus, the downregulating expressible polynucleotides may include a sequence as set forth in SEQ ID NO: 37.

T-cells are crucial to many aspects of immune function, making specific and precise modification of T-cell function an important objective of a wide range of preventive and therapeutic techniques. The present invention provides methods and compositions for specific neuropeptide-mediated regulation of T-cell function, viral and prion infection and tumor proliferation and metastasis via modulation of 67 kDa laminin receptor expression and function. These methods can be used to treat or prevent conditions resulting from suboptimal or excessive T-cell function, 67 kDa laminin receptor—mediated infection, tumor proliferation and metastatic spread.

Thus, according to one aspect of the present invention there is provided a method of regulating T-cell activity in a mammalian subject having abnormal T-cell activity, the method comprising providing to a subject identified as having the abnormal T-cell activity a therapeutically effective amount of a molecule selected as being capable of modifying an activity or expression level of a GnRH-I or a GnRH-II receptor thereby regulating T-cell activity in the mammalian subject.

According to still another aspect of the present invention there is provided a method of treating or preventing a T-cell related disease or condition characterized by abnormal T-cell activity in a mammalian subject, the method comprising providing to a subject identified as having the T-cell related disease or condition characterized by abnormal T-cell activity a therapeutically effective amount of a molecule selected as being capable of modifying an activity or expression level of a GnRH-I or a GnRH-II receptor, said amount being sufficient to regulate T-cell activity, thereby treating or preventing the T-cell related disease or condition in the mammalian subject.

In a preferred embodiment, downregulation of T-cell activity by ribozyme, antisense or DNA methodology directed against the GnRH-I or GnRH-II receptor is applied where the mammalian subject is suffering from excessive T-cell activity such as in autoimmune, neoplastic, hyperreactive, psychopathological, neurogenic and allergic diseases and conditions; graft versus host disease and allograft rejection.

Typically, tissues responsible for regulation of circulating GnRH-I or GnRH-II levels are found in the brain, and the cells of the neuroendocrine system should be the primary targets of such antisense, ribozyme or DNA therapy. However, while reducing the present invention to practice, it was surprisingly discovered that both GnRH-I and GnRH-II are produced in human T-cells. Thus, the inhibitory polynucleotides of these embodiments may be used to downregulate autocrine and paracrine GnRH-I and GnRH-II secretion by stimulated T-cells. Thus, antisense, ribozyme, siRNA and similar polynucleotides directed towards GnRH-I or GnRH-II transcripts can be introduced to the subject's cells in vivo, or ex vivo, to isolated T-cells, as described above. Such downregulating polynucleotides may include a sequence as set forth in SEQ ID NOs: 2, 3, and 33-36.

Patients having hyperproliferative disorders, which include both benign tumors and primary malignant tumors that have been detected early in the course of their development, may often be successfully treated by the surgical removal of the benign or primary tumor. If unchecked, however, cells from malignant tumors are spread throughout a patient's body through the processes of invasion and metastasis. Invasion refers to the ability of cancer cells to detach from a primary site of attachment and penetrate, e.g., an underlying basement membrane. Metastasis indicates a sequence of events wherein (1) a cancer cell detaches from its extracellular matrices, (2) the detached cancer cell migrates to another portion of the patient's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, Sci. Amer., 1996, 275, 72).

Disseminating precancerous or cancerous cells often display ectopic expression of substrate binding molecules which may facilitate step (3) of the metastatic process as described above. Thus, modulation of 67 kDa laminin receptor using the antisense compounds of the invention may result in a decreased ability of disseminating cancer cells to attach to a distal and/or inappropriate matrix, thereby modulating metastasis of the primary tumor. The importance of the 67 kDa laminin receptor to extravasation and metastatic spread of T-lymphoma and other cancer cells has been noted (see, for example, Wewer, U. M. et al., Proc Natl Acad Sci USA 1986; 83: 7137-41, and Hand, P. H. et al. Cancer Research 1985; 45: 2713-19).

While reducing the present invention to practice, it was noted that GnRH-I and GnRH-II stimulated 67 kDa laminin receptor expression, laminin binding and chemotactic migration in human T-cells (see Examples 5 and 6). Additionally, normal human T-cells exhibited reduced invasion of spleen and kidney of GnRH-I deficient (KO) mice (see Example 7), further supporting a role for GnRH in metastatic progression of tumors. Thus, inhibition of sensitivity to GnRH-I or GnRH-II stimulation may be effective in downregulating 67 kDa laminin receptor expression, providing a novel therapeutic approach for the treatment of non-steroid-dependent tumors. Thus, according to a further aspect of the present invention there is provided a method of relieving or preventing the proliferation of non-steroid-dependent tumor cells in a mammalian subject, the method comprising introducing into the cells a polynucleotide which specifically inhibits GnRH-I or GnRH-II receptor production, the polynucleotide capable of reducing sensitivity to GnRH-I or GnRH-II stimulation, thereby reducing proliferation of the tumor cells in the subject. In preferred embodiments of the present invention the downregulating polynucleotides are antisense, ribozyme and/or expressible polynucleotides encoding antisense or ribozyme oligoneucleotides capable of effectively reducing GnRH-I or GnRH-II receptor transcripts, as described above. Treatment of non-steroid-dependent tumors may be in combination with one or more additional anticancer compounds and/or chemotherapeutic drugs. The downregulating polynucleotides of the invention are evaluated for their ability to modulate metastasis using one or more assays known in the art and/or one or more appropriate animal models (see, for example, Examples 5-8 below).

Diseases or conditions related to T-cell deficiency or dysfunction would require upregulation of T-cell function, by GnRH-I or GnRH-II analogs possessing agonist or stimulatory properties. Although therapeutic use of GnRH and agonist analogs of GnRH-I and GnRH-II has been previously disclosed (U.S. Pat. No. 5,140,009 to Haviv, et al; U.S. Pat. No. 5,574,011 to Tein; Sharkey, J. et al. J. Endourol 2000 May; 14(4): 343-50; Klijn, J G et al. J. Clin Oncol 2001 Jan. 15; 19(2) 343-53; U.S. Pat. No. 5,593,965 to Lovas, et. al.; Intnl Pat. Applications WO 00/12115 and 00/01403, both to Eriksson, T and Bergentall, A; Ben-Yehudah, A. et al. Int J Cancer 2001 Apr. 15; 92(2): 263-8), the disclosed applications have either targeted the disruption of regulation of sex hormone levels, and/or the GnRH binding sites of gonad related cancer cells. No mention has been made of neuro-immune effects via laminin receptor regulation.

In one preferred embodiment, modification of GnRH-I or GnRH-II receptor activity is used to regulate T-cell activity in a mammalian subject having abnormal T-cell activity, wherein the abnormal T-cell activity is suboptimal. This is effected by providing to the subject a therapeutically effective amount of an upregulator of GnRH-I or GnRH-II receptor activity or an expression of a gene encoding a GnRH-I or GnRH-II receptor. In the method of the present invention, the upregulating molecule may be administered in vivo, by administration to the subject via intravenous, parenteral, oral, transdermal, intramuscular, intranasal or other means or ex vivo, after removal of T-cells from the body and their isolation.

T-cells may be isolated from the blood by procedures known to one skilled in the art (see, for example, the Materials and Methods section that follows).

A specific example of such ex vivo treatment of immune cells for activation and therapeutic readministration may be found in Intn'l Pat. No. WO9950393A2 and A3 to Wank, although the methods described differ significantly from the methods disclosed herein. Wank describes the isolation and in vitro activation of peripheral blood mononuclear cells (phagocytes) from patients suffering from brain-related diseases, disorders and damage, including psychoses, autism, schizophrenia and developmental disturbances. In a report documenting adoptive immunotherapy of patients suffering from bipolar disorder, schizophrenia or autism, Wank describes similar in-vitro activation, and reintroduction of the patients' own T-cells, in order to combat "chronically infected", understimulated lymphocytes thought associated with these disorders. In this form of therapy, the T-cells are not stimulated directly, rather via monoclonal antibodies against the CD3 polypeptide complex, and IL-2. The patients were required to endure numerous weekly treatments (up to 104 weeks in one patient), and although improvement in some symptoms was noted, additional therapies were continued during and after these trials of adoptive immunotherapy. No mention is made of direct stimulation of T-cells with neurotransmitters, of specific T-cell response to therapy, or of treatment with GnRH-I or GnRH-II, GnRH-I or GnRH-II analogs or other upregulators of T-cell GnRH-I or GnRH-II receptor activity.

Thus, according to one aspect of the present invention, there is provided a population of T-cells suitable for treating or preventing a disease or condition characterized by abnormal T-cell activity in a subject, the population of cells comprising T-cells characterized by modified sensitivity to GnRH-I or GnRH-II receptor stimulation. Such a population of T-cells can be used for treating or preventing a disease or condition characterized by abnormal T-cell activity upon administration to the subject. In one preferred embodiment, the sensitivity to GnRH-I or GnRH-II stimulation is modified by an exogenous expressible polynucleotide sequence encoding a GnRH-I or GnRH-II receptor, imparting increased sensitivity to GnRH-I or GnRH-II. Administration of a population of such sensitized T-cells can be beneficial in conditions of suboptimal T-cell activity, such as immunodeficiency, infection, neurological disease, injury and the like. It will be appreciated, in the context of the present invention, that such increased sensitivity to GnRH-I or GnRH-II stimulation can directly benefit patients by increasing the mobilization, migration and extravasation of T-cells to organs in need of enhanced contact with lymphocyte populations. Homing and proliferation of the transformed T-cells can be monitored by methods immuno-detection of the expressed proteins (FACS, ELISA), or detection of T-cells containing the transformed nucleic acids or their transcripts (PCR, etc) known to one skilled in the art.

The modified T cells can be administered in vivo autologously (i.e., to the same individual from which the T cells (or parental cells to the T cells were originally obtained) or syngeneically (i.e., to an identical twin of the individual from which the cancer or infected cells were initially obtained); or allogeneically to an individual who shares at least one common MHC allele with the individual from which the modified cells and T cells were originally obtained.

In another preferred embodiment, modified T cells reactive against human cancer cells can be used, alone or in conjunction with surgery, chemotherapy, radiation or other anti-cancer therapies, to eradicate metastases or micrometastases, or to purge bone marrow of cancer cells during bone marrow transplantation. For example, to eradicate or inhibit the growth of metastases or micrometastases, tumor antigen reactive T cells are identified, and modified by the methods of the present invention for enhanced sensitivity to GnRH-I or GnRH-II stimulation, and are administered in vivo, to the subject having or suspected of having the metastases or micrometastases. Increased T-cell mobilization enhances tumor homing and site specific action of the T-cells.

Moreover, if cancer patients undergo surgery with anesthesia, and subsequent chemotherapy, the resulting immunosuppression experienced by the patient may be lessened by cellular immunotherapy in the preoperative period, thereby reducing the incidence of infectious complications.

In another preferred aspect, the invention provides modified T cells reactive against an opportunistic pathogen that infects immunosuppressed or immunodeficient subjects, such as but not limited to cytomegalovirus, *Toxoplasma gondii, Herpes zoster, Herpes simplex, Pneumocystis carinii, Mycobacterium avium-intracellulare, Mycobacterium tuberculosis, Cryptosporidium*, and *Candida* species.

In another preferred embodiment, the expressible polynucleotide sequence is capable of downregulating expression of a gene encoding a GnRH-I or GnRH-II receptor, such as a ribozyme or antisense polynucleotide. Administration of populations of such desensitized T-cells can be beneficial in conditions and diseases of excess T-cell activity, such as autoimmune, allergic, pyschopathological (see example described hereinabove) neurological disease, cancerous conditions and the like. Suitable polynucleotides, and methods for their use in the present invention, are described in detail herein. Additional methods for ex vivo treatment, selection, expansion and culturing of T-cells for readministration are well known in the art (see, for example, U.S. Pat. No. 6,451, 316 to Srivatava).

The methods of the present invention can be used for treatment and prevention of T-cell related diseases or conditions characterized by suboptimal T-cell activity, such as congenital immune deficiencies, acquired immune deficiencies, infection, neurological disease and injury, psychopathology and neoplastic disease, by providing a molecule selected as being capable of upregulating an activity or expression level of a GnRH-I or GnRH-II receptor. Immune deficient diseases or conditions that can be treated by upregulation of GnRH-I and GnRH-II-mediated T-cell activity of the methods of the present invention include congenital and acquired primary immunodeficiencies, such as the acquired immunodeficiency syndrome (AIDS), DeGeorge's syndrome, severe combined immunodeficiency; and secondary immunodeficiencies, such as anergy from tuberculosis, drug-induced leukopenia, non-HIV viral illnesses leukopenia, radiation poisoning, toxin exposure, malnutrition, and the like. Of special significance are neurogenic diseases and conditions in which increased T-cell activity may be beneficial, such as Parkinson's and Alzheimer's Disease. Similarly, neoplastic disease or conditions resulting from failure of immune surveillance, and bacterial, fungal, viral and parasitic infections may respond to upregulation of protective T-cell function by GnRH-I or GnRH-II, agonist (upregulating) GnRH-I or GnRH-II analogs, upregulating anti-GnRH-I and GnRH-II receptor antibodies, and expressible polynucleotides encoding a GnRH-I and GnRH-II receptor.

It will be appreciated that when treating such immune deficient conditions, dosage and treatment protocols are often determined according to severity of the disease or condition, co-existing complicating diseases or health factors, age, etc., and the subject's individual response to GnRH-I or GnRH-II receptor-mediated upregulation of T-cell activity. In one specific example, T-cells are isolated from the patient prior to treatment (as detailed in the Examples section hereinbelow) and tested for, laminin adhesion, chemotactic reactivity and/or specific gene expression. Response to ex vivo treatment of T-cell with specific upregulators of GnRH-I or GnRH-II receptor activity, such as any of SEQ ID NOs 4-29, is then monitored within 48 hours of administration, and periodically until normalization of T-cell function and abatement of immune hypofunction is achieved. Thus, in one preferred embodiment, upregulating T-cell activity in the subject results in a change in at least one T-cell activity such as laminin adhesion, chemotaxis, and extravasation, which is monitored in T-cells of the subject.

In the context of the present invention, it is important to note the contribution of immune system dysfunction to aging processes. Altered signal transduction and aberrant cytokine production has been demonstrated in T-cells of elderly individuals, and aging T-cells are more susceptible to apoptosis (Pawelec, G. and Solana, R. Immunoageing—the cause or effect of morbidity? Trends in Immunol. 2001: Jul. 22(7) 348-9). Thus, upregulation of T-cell function by GnRH-I or GnRH-II, agonist GnRH-I or GnRH-II analogs, upregulating anti-GnRH-I or GnRH-II receptor antibodies and expressible polynucleotides encoding a GnRH-I or GnRH-II receptor may be used to treat immune-related symptoms and processes of aging.

Diseases or conditions requiring suppression of immune function may be sensitive to inhibition of T-cell activity by antagonist GnRH-I or GnRH-II analogs, downregulating anti-GnRH-I or GnRH-II receptor antibodies, and/or polynucleotides downregulating GnRH-I or GnRH-II receptor expression. These diseases or conditions include autoimmune states such as systemic lupus erythematosis, rheumatic fever, rheumatoid arthritis, multiple sclerosis Hashimoto's and Grave's disease, Goodpasture's syndrome, myasthenia gravis, insulin-dependent diabetes mellitus, pemphigus vulgaris, Addison's disease, dermatitis herpetiformis and celiac disease; allergic conditions such as atopic dermatitis, allergic asthma, anaphylaxis and other IgE-mediated responses. Similarly, other conditions of undesired T-cell migration and function include T-cell cancer such as T-lymphoma, T-cell mediated graft versus host disease and allograft rejection. Importantly, psychopathological and neurogenic diseases and conditions associated with increased GnRH-I or GnRH-II-mediated T-cell activity such as schizophrenia, migraine and de novo Parkinson's Disease may be treated with the methods and compounds of the present invention.

While reducing the present invention to practice, it was demonstrated that GnRH-I or GnRH-II modulation of T-cell function was mediated in part by GnRH-I or GnRH-II effect on non-integrin 67 kDa laminin receptor binding to laminin, chemotaxis and T-cell extravasation. Importantly, the non-integrin glycoproteins on the surface of circulating leukocytes recognize and bind to the adhesion proteins expressed on the surface of activated endothelial cells, enabling the migration of leukocytes across the blood vessel walls to the site of the injury or infection. The leukocytes then release chemical mediators, and cytokines to combat the invading matter. In a similar manner, neurogenic diseases such as MS, EAE and meningitis are characterized by indiscriminate destruction of brain tissue caused by the release of toxic mediators by leukocytes which errantly migrate across the blood brain barrier (BBB). Therefore, inhibition of 67 kDa laminin binding and T-cell activation by antagonist GnRH-I or GnRH-II analogs, anti-GnRH-I or GnRH-II receptor antibodies, and/or polynucleotides down-regulating GnRH-I or GnRH-II receptor expression may be effective in preventing and/or treating T-cell related hyperreactive, autoimmune, allergic, neoplastic, neurogenic, metastatic, psychopathological and infectious conditions.

Thus, according to the present invention there is provided a method of regulating T-cell activity in a mammalian subject having excessive T-cell activity, the method effected by providing to the subject a molecule selected as being capable of downregulating an activity or expression level of a GnRH-I or GnRH-II receptor. Similarly, there is provided a method of preventing or treating a T-cell related disease or condition characterized by excessive T-cell activity in a subject having such a disease or condition by providing to the subject a molecule selected as being capable of down-regulating an activity or expression level of a GnRH-I or GnRH-II receptor. In one embodiment, the downregulator is a GnRH-I or GnRH-II receptor antagonist, such as Cetrorelix (SB-75). In a preferred embodiment, the downregulator is an anti-GnRH-I or GnRH-II receptor antibody. In a more preferred embodiment, the downregulator is a single stranded polynucleotide designed having specific GnRH-I or GnRH-II receptor transcript cleaving capability, an expressible polynucleotide encoding a ribozyme designed having specific GnRH-I or GnRH-II receptor transcript cleaving capability, a polynucleotide designed comprising nucleotide sequences complementary to, and capable of binding to GnRH-I or GnRH-II receptor transcripts, coding sequences and/or promoter elements and an expressible polynucleotide encoding nucleotide sequences complementary to, and capable of binding to GnRH-I or GnRH-II receptor transcripts, coding sequences and/or promoter elements.

As mentioned hereinabove, T-cells may be isolated from the blood by procedures known to one skilled in the art (see, for example, the Materials and Methods section that follows). Thus, in the method of the present invention providing the downregulating molecule is effected by in vivo, by local or systemic administration to the subject via intravenous, parenteral, oral, transdermal, intramuscular, intranasal or other means, or by providing the downregulating molecule to an ex vivo T-cell population, after removal of T-cells from the body and their isolation, and their readministration to the subject, as described in detail hereinabove.

The neuropeptide GnRH-II, although partially homologous to the neurohormone GnRH-I, has been shown to exert only a very mild effects on reproduction in mammals (Merril, J. E. and Benveniste, E. N. Trends in Neuroscience 1996. 19: 331-38). However, while reducing the present invention to practice, it was observed that GnRH-II, as GnRH-I, stimulated 67 kDa laminin receptor expression, extravasation, migration and chemotaxis in human T-cells (see Examples section), in physiological concentrations, and via a distinct, non-GnRH-I cell surface receptor. Thus, inhibition of metastasis and tumor growth related to 67 kDa laminin receptor activation may be inhibited by blocking GnRH-II activity in both gonadal steroid-dependent and steroid independent tumors.

Thus, inhibition of sensitivity to GnRH-I or GnRH-II stimulation may be effective in downregulating 67 kDa laminin receptor binding, providing a novel therapeutic approach for the treatment of T-cell related cancers. According to a further aspect of the present invention there is provided a method of treating or preventing a cancerous disease or condition in a subject suffering from a cancerous disease or condition characterized by excess T-cell activity, by providing to the subject a therapeutically effective amount of a molecule selected as being capable of downregulating an activity of a GnRH-I or GnRH-II receptor or an expression of a gene encoding a GnRH-I or GnRH-II receptor. The method can further comprise the step of determining the cancer cell proliferation and/or metastasis in the subject prior to, and/or following the treatment. Well-known, art-recognized methods for determining proliferation include mitotic index, thymidine uptake and the like. Metastatic spread can be monitored by identification of specific T-cell subtypes using immunochemical and/or DNA based techniques such, as FACS or PCR. In preferred embodiments of the present invention the downregulating molecules are anti-GnRH-I or GnRH-II antibodies, GnRH-I or GnRH-II antagonists, and down-regulating polynucleotides such as antisense, ribozyme and/or expressible polynucleotides encoding antisense or ribozyme oligoneucleotides capable of effectively reducing GnRH-I or GnRH-II receptor transcripts, as described above, and may be introduced to the subject by systemic or local administration in vivo, or to an ex vivo population of the subject's T-cells, and readministered, as detailed hereinabove. In another preferred embodiment, the cancerous disease or condition is a myeloproliferative disease, such as Leukemia or T-cell cancer. Treatment of the T-cell cancer cells may be in combination with one or more additional anticancer compounds and/or chemotherapeutic drugs. The downregulating molecules of the invention are evaluated for their ability to modulate proliferation and/or metastasis using one or more assays known in the art and/or one or more appropriate animal models (see, for example, Johnston, J A et al, 1994 J. Immunol 153, 1762-68).

Further according to the present invention there is provided an assay for determining the sensitivity of a resting T-cell population to regulation of GnRH-I or GnRH-II receptor activity. The assay is effected by exposing the T-cell population to a molecule selected as being capable of regulating a GnRH-I or GnRH-II receptor activity or the expression of a gene encoding a GnRH-I or GnRH-II receptor, and assessing the state of the T-cell population.

In one preferred embodiment, the assay is performed by exposing the T-cell population to a range of concentrations of the GnRH-I or GnRH-II receptor regulator, and assessing the state of the T-cell population at each concentration of the range. Physiologically active concentrations of GnRH-I or GnRH-II as demonstrated in Examples 5-8, are in the range of 1-1000 nM. In a most preferred embodiment, effective concentrations are assessed from 1-100 nM. Specific examples of such assays, using molecules capable of upregulating and downregulating T-cell GnRH-I or GnRH-II receptor activity, are detailed throughout the Examples section hereinbelow (see, for example, Examples 5-8). As described therein, T-cell functions such as laminin adhesion, chemotaxis, extravasation and up-and downregulation of specific genes can be assayed to determine the sensitivity of GnRH-I or GnRH-II receptor regulators. Likewise, the effect of the abovementioned upregulating modulators may be assayed in a T-cell population isolated from a subject suffering from an immune deficiency, infectious, age-related, neurogenic, psychopathological or other disease or condition requiring enhanced T-cell activity (see abovementioned list of conditions).

Similarly, efficacy, potency and receptor specificity of putative GnRH-I or GnRH-II receptor regulators may be determined using the assay of the present invention. Changes in a designated state of test T-cell populations can be compared with changes in populations exposed to known, reference regulators. Such an assay can also be used to characterize and compare individual T-cell populations, such as T-cell leukemic cells and T-cell lines.

In a further embodiment, the molecule is an expressible polynucleotide designed so as to be capable of regulating expression of a gene encoding a GnRH-I or GnRH-II receptor. The expressible polynucleotides may be designed so as to be capable of transient expression within the cells of the T-cell population, or designed so as to be capable of stably integrating into the genome of cells of the T-cell population expression in the T-cell, as described in detail hereinabove.

In the case of a T cell related neoplastic disease, the assay may be effected by exposing a T-cell related cancer cell to one or more concentrations of a GnRH-I or GnRH-II analog and assessing the ability of the cancer cell to proliferate and/or metastasize. In a preferred embodiment the GnRH-I or II analog concentration may be 0.1 ng/ml to 1 mg/ml, sufficient to produce a significant alteration in T-cell activity, as measured by, for example, laminin binding, chemotaxis, specific gene expression and the like (see Examples section that follows). The assay may be performed in vitro or in vivo, using T-cell related cancer cells. By varying the assay conditions, the sensitivity of a cancer cell to GnRH-I or GnRH-II analog inhibition of proliferation and metastasis may be assessed. The GnRH-I or GnRH-II analog may a naturally occurring or synthetic analog.

Similarly, the assay of the present invention may be applied to additional methods of upregulating T-cell activity. Thus, the sensitivity of a T-cell to upregulating analogs, or to expressible polynucleotides encoding GnRH-I or GnRH-II receptors and/or to upregulating anti-GnRH-I or GnRH-II receptor antibodies may be assayed. Exposure of the T-cells to the upregulating modulators may be performed in vivo, in vitro or ex vivo, as described in the Examples section that follows.

Consistent with, and in addition to the methods for modulation of GnRH hormone levels detailed herein, endogenous production of GnRH in the brainstem and hypothalamus, or other GnRH producing tissues of an organism (for example kidney, bone marrow, prostate and placenta) may be increased or inhibited by physiological or non-physiological factors. In addition, autocrine GnRH secretion by T-cells may be modulated. Such modulation of endogenous GnRH can further regulate 67 kDa LR associated activity in T- and other GnRH-sensitive cells.

The abovementioned methods for modulation of T-cell activity via modification of GnRH-I or GnRH-II receptor-mediated activity can be effected as described using the down- and upregulating molecules described hereinabove, per se. Further, the methods of T-cell regulation described can be effected using pharmaceutical compositions, the compositions including a molecule selected as being capable of modifying an activity or expression level of a GnRH-I or a GnRH-II receptor in T-cells and a pharmaceutically acceptable carrier.

Further according to the present invention, there is provided an article of manufacture comprising packaging material and a therapeutically effective amount of a pharmaceutical composition identified for treatment of a T-cell related disease or condition associated with abnormal T-cell activity, the pharmaceutical composition including a molecule selected as being capable of modifying an activity or expression level of a GnRH-I or GnRH-II receptor in T cells, and a pharmaceutically effective carrier. The pharmaceutical composition is identified as effective for treatment of the T-cell related disease or condition by a label or insert included in the packaging material, bearing, for example, clinical indications for use, notification of FDA approval, recommended dosages, frequency and modes of administration, contraindications and the like.

In one preferred embodiment, the pharmaceutical composition comprises as an active ingredient a molecule selected as being capable of upregulating GnRH-I or GnRH-II receptor activity, or the expression of a gene encoding the GnRH-I or GnRH-II receptor, packaged and identified for use in the prevention and/or treatment of a T cell related disease or condition characterized by suboptimal T-cell activity. The GnRH-I or GnRH-II receptor upregulator can be GnRH-I or GnRH-II, an upregulating GnRH-I or GnRH-II analog, an upregulating anti-GnRH-I or GnRH-II receptor antibody or an expressible polynucleotide encoding a GnRH-I or GnRH-II receptor.

In another embodiment, the pharmaceutical composition comprises a downregulator of GnRH-I or GnRH-II receptor activity, as described in detail hereinabove. Such an article of manufacture comprising the down-regulating pharmaceutical composition, packaged and identified for use to treat or prevent a T-cell related disease or condition characterized by excessive T-cell activity, as described in detail hereinabove.

The compositions of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci. 1977, 66, 1-19).

For therapeutic or prophylactic treatment, peptides, peptide fragments, polynucleotides and antibodies are administered in accordance with this invention. Components of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the peptides, peptide fragments, polynucleotides and antibodies. Such compositions and formulations are comprehended by the present invention.

As used herein, the term "pharmaceutically acceptable carrier" (excipient) indicates a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the GnRH-I or GnRH-II analogs, polynucleotides and antibodies of the invention are introduced into a patient, colloidal dispersion systems may be used as delivery vehicles to enhance the in vivo stability of the and/or to target the analogs, polynucleotides and antibodies to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:catecholamine, polynucleotide and/or antibody complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708).

For therapeutic uses, the pharmaceutical compositions of the present invention may be administered in a number of ways depending upon whether local or systemic treatment is desired and upon the area to be treated. Administration may be topical (including ophthalmic and to mucous membranes including vaginal and rectal delivery) pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For certain conditions, particularly skin conditions including but not limited to, psoriasis, administration of compounds to the skin is preferred. Administration of compounds to the skin may be done in several ways including topically and transdermally. A preferred method for the delivery of biologically active substances to the skin is topical administration. "Topical administration" refers to the contacting, directly or otherwise, to all or a portion of the skin of an animal. Compositions for topical administration may be a mixture of components or phases as are present in emulsions (including microemulsions and creams), and related formulations comprising two or more phases. Transdermal drug delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of penetration enhancers. Hydration of the skin and the use of controlled release topical patches are also effective ways to deliver drugs via the transdermal route. This route provides an effective means to deliver drugs for both systemic and local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose:deposition and retention at the site of administration (Lee et al., Critical Reviews in Therapeutic Drug Carrier Systems, 1991, p. 168) may be useful methods for enhancing the transport of drugs across mucosal sites in accordance with the present invention.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice may be, for example, of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes 1-111 Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 14, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Human T-Cells:

Human T-cells were purified from the peripheral blood of healthy donors as follows: blood was diluted 1:1 in sterile phosphate-buffered saline (PBS) and the leukocytes were isolated on a Ficoll gradient. After washing, the cells were incubated on nylon-wool columns (Novamed Ltd., Jerusalem, Israel). One hour later, non-adherent T-cells were eluted, washed, and counted. The resulting cell population consisted of >95% T-cells, as evaluated by TCR staining and evaluated using a fluorescence-activated cell sorter (FACSORT).

Mice:

Normal C3H/HeH and C57BL/6 mice were obtained from the Jackson Laboratory (Bar Harbour, Me., USA). GnRH-I knockout (KO) hpg mice were a gift of Dr. G. Fink (Edinburgh U.K).

Antibodies:

The following antibodies, antisera and sera were used throughout this study: a polyclonal antibody against GnRH-I, prepared and characterized in our laboratory, was used for RIA. GnRH-II or salmon GnRH did not displace any of the bound $^{125}$I-GnRH-I even at a concentration that exceeded by 1000 times the GnRH-I concentration that is needed for displacing 50% of the tracer (20 ng vs. 20 pg). A monoclonal antibody against GnRH-I, kindly provided by Dr. H. F. Urbansky, was used at dilutions ranging from 1:4000 to 1:10,000 for the immunofluorescence studies; the specificity of this antibody (HU4H) was reported elsewhere 57. Two polyclonal antibodies against GnRH-II were used. One antibody, aCII6, was kindly provided by Dr. K. Okuzawa and its specificity was previously defined 10, 58. The second antiserum, KLII-2, was prepared and characterized in our laboratory. Specificity tests of this antibody have demonstrated that GnRH-I did not displace any of the bound $^{125}$I-GnRH-II, even at a concentration that exceeded 1000 times the GnRH-II concentration that is needed to displace 50% of the tracer (30 ng vs. 30 pg). Salmon GnRH cross-reacted with this antisera by 0.003% and with antibody aCII6 by 0.013%. We have utilized dilutions ranging from 1:4000 to 1:10,000 of the GnRH-II antibodies for the immunohistochemical studies.

In addition, the following antibodies or antisera were used: mouse monoclonal anti-67 kDa LR antibody (LR Ab-1, clone MluC5; NeoMarkers, Fremont, Calif.), normal mouse sera for control (Jackson, Immunoresearch Laboratories, INC. Pennsylvania), PE-conjugated mouse anti-human TCR mAb (Seroteq, Oxford, UK), FITC-conjugated goat anti-mouse IgG and PE-conjugated goat anti mouse TCR mAb (Pharmigen, San Diego, Calif.), anti-human VLA-6 antibodies mAb (Seroteq, Oxford, UK), anti-human CD3 mAb and anti-human CD28 mAb (Pharmigen).

Immunofluorescence Staining for the 67 kDa Laminin Receptor:

Normal human T-cells, isolated from fresh peripheral blood lymphocytes, or EL-4 T-lymphocyte cells were subjected to double immunofluorescence staining, using a mouse monoclonal anti-67 kDa LR antibody (100 µl of 1:20 dilution per 1×10$^6$ cells/tube; 30 minutes on ice), or normal mouse sera for control. The cells were then stained with an FITC-conjugated goat anti-mouse IgG (100 µl of 1:100 dilution), and PE-conjugated mouse anti-human TCR αβ mAb (2 µl of stock). Cells that were stained only with the second and third antibodies served as additional negative controls. Fluorescence profiles were recorded in a FACSORT.

T-Cell Adhesion Assay:

Adhesion of T-cells to laminin was assayed as follows: normal human T-cells, purified from a fresh blood sample, were suspended (1×10$^6$ cells/ml) in rest medium (RPMI-1640, supplemented with 10% fetal calf serum (Sigma Chemical Co., St. Louis, Mo.), 1% antibiotics, 1% glutamine (Biological Industries, Beit Haemek, Israel) and 0.4% fungizone (GibcoBRL, Life Technologies Ltd., Paisley, Scotland)). The cells were then supplemented with 10 nM GnRH-I or GnRH-II and incubated for variable periods of time (0.5-72 hours, 37° C., 7.5% $CO_2$ humidified incubator). Following incubation the cells were washed and resuspended in adhesion medium (RPMI-1640 supplemented with 0.1% bovine serum albumin (BSA, Sigma)). The cells were then seeded in 96 well flat-bottomed microtiter plates (Falcon, Becton Dickinson, Heidelberg, Germany), 1×10$^5$ cells/100 µl/well pre-coated with laminin (ICN Biomedicals Inc., Aurora, Ohio, 0.5 mg/well, 18 hours, 4° C.). Cells treated with phorbol 12-myristate 13-acetate (PMA, Sigma, 10 ng/ml) served as a positive control. The adhesion plates were incubated (37° C., 30 minutes, 7.5% $CO_2$ humidified incubator), and then washed several times with PBS to remove non-adherent T-cells. The adhered cells were lysed by adding 60 µl/well of lysis-substrate solution (0.5% Triton X-100 in water mixed with an equal volume of 7.5 mM p-nitrophenol-N-acetyl-β-D-glucosaminide (Sigma) in 0.1M citrate buffer pH=5.0). The plates were then incubated for 18 h in a $CO_2$-devoid 37° C. incubator, and the reaction was stopped by the addition of 90 ml/well of 50 mM glycine (Sigma) pH=10.4, containing 5 mM EDTA. The optical density (OD) was measured at 405 nm in a standard ELISA reader. The OD was converted to actual number of cells using a standard curve performed in each experiment.

In-Vitro Migration Assay:

Normal human T-cells (1×10$^6$ cells/well in rest medium) were pretreated with GnRH-I or GnRH-II (10 nM, >18 hours, 37° C., 7.5% $CO_2$ humidified incubator), washed, resuspended in adhesion medium and fluorescently labeled (50 µg/ml, 30 minutes, 37° C., 7.5% $CO_2$ humidified incubator) with 2',7'-bis-(2-carboxyethyl)-5-(and-6)-carboxyfluorescein acetoxymethyl (BCECF AM, Molecular Probes, Eugene, Oreg.). The cells were then washed, resuspended in adhesion medium, and added to the upper chambers ($2 \times 10^5$ cells per 100 µl well) of a 24-well chemotaxis microchamber plate (Corning Inc., Corning, N.Y.). The two compartments of the microchambers were separated by polycarbonate filters (5.0 mm pore size) pre-coated with laminin (25 mg/ml, about 1.5 hour, 37° C.). The lower chambers contained adhesion medium, which was supplemented, where indicated, with 100-250 ng/ml of the chemokine stromal cell-derived factor 1a (SDF-1a, Peprotech Inc., Rocky Hill, N.J.). The chemotaxis microchamber plate was incubated (3 hours, 37° C., 7.5% $CO_2$ humidified incubator), the filter-containing upper chambers were then gently removed and the content of the individual lower chambers (containing the migrated cells) was thoroughly mixed by pipetting and transferred into clean tubes. The number of cells in each tube was determined by FACSORT. Counting time for all the experimental groups was two minutes.

T-Cell Receptor (TCR) Activation:

Normal human T-cells, separated from blood samples of healthy donors, were activated via their TCR as follows: 24-well plates (non-tissue culture treated, Becton-Dickinson, N.J.) were precoated with 0.5 ml/well of PBS containing a mixture of anti-human CD3 and anti-human mAbs (1 µg/ml final of each Ab, 4° C., overnight). The plate was then washed with PBS, blocked (0.5 ml/well of PBS containing 1% BSA (Sigma), 20-30 minutes, 37° C., 7.5% $CO_2$ humidified incubator), and washed again with PBS. After washing, the cells were seeded into the mAbs-coated wells ($1$-$1.5 \times 10^6$ cells/ml (rest medium)/well) and incubated (24-48 hours, 37° C., 7.5% $CO_2$ humidified incubator). After incubation, the cells were collected, counted and used for further experiments.

Initiation and Propagation of Antigen-Specific T-Cell Lines:

Anti-MBP 87-99 T-cell lines were established from lymph nodes of SJI/J mice as described[23] and analyzed for their specificity to MBP 87-99 peptide in a proliferation assay.

Analysis of Gene Expression Using the Atlas cDNA Expression Array:

Poly A+RNA was extracted from the mouse anti-MBP 87-99 cell line before and after treatment with 10 nM GnRH-II for 24 hours, using the ATLAS Pure Total RNA Labeling System (Clontech Laboratories, Inc. Palo Alto, Calif.) according to manufacturers recommendations. Following DNase treatment, $^{32}$P-labeled cDNA was prepared from poly A+ RNA preparations that were prepared from either untreated or GnRH-II treated mouse T-cells. Hybridizations to the ATLAS Mouse cDNA Expression Arrays membranes (Catalog No. PT3140-1, Clontech Laboratories), were performed according to the user manual, and the expression pattern was visualized by autoradiography.

Reversed Transcription (RT) PCR and Southern Analysis:

Total RNA was extracted by using Trizol RNA isolation reagent (Molecular Research Center, Cincinnati, Ohio) based on the acid guanidinium thiocyanate-phenol-chloroform extraction method, according to manufacturer recommendations. RT-PCR was used to amplify the levels of endogenous GnRH-II and GnRH-I mRNA that may be present in the peripheral human T-cells and in the Jurkat cells (a human mature leukemic cell line that phenotypically resembles resting human T lymphocytes). The expression of the ribosomal protein S-14[59] derived from the same tissue preparations, served as an internal control. Each reaction contained four oligonucleotides primers, two for GnRH-I or GnRH-II and two for the internal control S-14. Amplification was carried out for 35 cycles, the annealing temperature was 62° C. for GnRH-II and S-14 reaction and 60° C. for GnRH-I and S-14 reaction, the final $MgCl_2$ concentration was 2.5 mM. LR PCR conditions were: cDNA equivalent to 50 ng RNA was amplified for 28 cycles, the annealing temperature was 60° C. and the final $MgCl_2$ concentration was 2.5 mM. The Taq DNA polymerase used in this study was the BIO-X-ACT DNA polymerase (Bioline UK Ltd., London. UK). The PCR products were transferred to a nylon membrane (NYTRAN 0.45, Schleicher & Schuell, Dassel, Germany) in 20×SSC solution overnight. The nylon was baked in a vacuum oven at 80° C. for 2 hours. Pre-hybridization was performed in the presence of 6×SSC, 5×Denhardt's solution, 5 mM EDTA and 0.2 mg/ml salmon sperm DNA for 3 hours. Overnight hybridizations were performed, sequentially on the same membrane, in the presence of a $^{32}$P labeled probe, specific to the GnRH-I, GnRH-II, laminin receptor or S-14 cDNA. Hybridizations were performed at 64° C. for GnRH-II and S-14 probes, 60° C. for GnRH-I probe, and at 58° C. for laminin receptor probe. The corresponding band can be seen after 1 hour of exposure using a phosphorimager (445 SI, Molecular Dynamics, Inc., Jersey City, N.J.). Gels were also exposed to X-Ray film (Fuji Photo Film Co., Ltd., Tokyo, Japan) for 2-16 hours at −80° C. and developed in CURIX 60 processor (AGFA; Koln, Germany).

Oligonucleotide Primers:

For the PCR reactions the following specific GnRH-I, GnRH-II, laminin receptor and S-14 oligonucleotide primers were used: (a) GnRH-I—5' AGTACTCAACCTACTTCAAG 3' (SEQ ID NO:38) and 5' CATTCAAAGCGTTGGGTTTCT 3' (SEQ ID NO:39) corresponding to nucleotides 1134-1153 (sense) and 3746-3766 (antisense) respectively 60 The predicted size of band is 248 base pairs; (b) GnRH-II—5' CTGCAGCTGCCTGAAGGAG 3' (SEQ ID NO:40) and 5' CTAAGGGCATTCTGGGGAT 3' (SEQ ID NO:41) corresponding to nucleotides 1312-1330 (sense) and 2232-2250 (antisense) respectively 13 The predicted size of band is 197 base pairs; (c) Laminin receptor—5' CACAATGTCCGGAGCCCTTGA 3' (SEQ ID NO:42) and 5'GCTTAAGAGC-CTATGCAAGAAC 3' (SEQ ID NO:43) corresponding to nucleotides 12-32 (sense) and 907-928 (antisense) respectively[41]. The predicted size of band is 917 base pairs. S-14-5' GGCAGACCGAGATGAATCCTCA 3' (SEQ ID NO:44) and 5' CAGGTCCAGGGGTCTTGGTCC 3' (SEQ ID NO:45) corresponding to nucleotides 2941-2962 (sense) and 4166-4186 (antisense) respectively[61]. The predicted size of band is 143 base pairs. The oligonucleotide probes for hybridization were: (a) GnRH-I—5' CCAAGTCAGTAGAATAAG-GCC 3' (SEQ ID NO:46) corresponding to nucleotides 2091-2111; (b) GnRH-II—5' GCAGGAGGCCTCGCCTGGAGCTGGCCATGGCTGCT 3' (SEQ ID NO:47) corresponding to nucleotides 2098-2132; (c) Laminin receptor—5' CAGAGGAGAATCTGTGTTA-CACAG 3' (SEQ ID NO:48), corresponding to nucleotides 454-477. S-14-5' ATATGCTGCTATGTTGGCTGC 3' (SEQ ID NO:49) corresponding to nucleotides 2965-2985.

DNA Sequencing:

The appropriate cDNA fragments of GnRH-I and of GnRH-II from the peripheral human T cells, were extracted from the gels by using the QIAquick Gel Extraction Kit (QIAGEN GmbH, Hilden, Germany) and subcloned into pGEM-T vector by using the pGEM-T Easy Vector System I (Promega Corporation, Madison, Wis.). The nucleotide sequencing of the specific PCR bands were obtained by automated direct DNA sequencing, according to the manufacturers recommendations (PE Applied Biosystems; model 377, Perkin Elmer Corp, Foster City, Calif.).

Cell Processing for GnRH Determination:

The Jurkat cells (about $1 \times 10^9$) were immersed in ice-cold 0.1N HCl and homogenized by a Polytron homogenizer. Following centrifugation (12,000×g, 30 minutes at 4° C.) the supernatant was pumped onto columns of Sep-Pak C-18 cartridges (Waters Corporation, Milford, Mass.), washed by 0.1% trifluoroacetic acid (TFA), eluted by methanol and evaporated by nitrogen. Following reconstitution in 0.1% TFA (1 ml) the extracts were processed through reversed phase (RP) high performance liquid chromatography (HPLC) using C-18 columns, and eluted using the following conditions: eluent A, 0.1% TFA in water; eluent B, 75% $CH_3CN$ in 0.1% TFA. The gradient program consisted of a linear gradient of eluent B 20%-30% for 5 minutes at a flow rate of 1 ml/minutes, followed by an isocratic elution of 30% eluent B for 35 minutes, and continued with 100% of eluent B for additional 20 minutes All fractions were evaporated to a volume of 0.1 ml, reconstituted with 0.1 M of phosphate buffer (PB, pH 7.4) containing 0.1% of bovine γ-globulin and the concentration of GnRH-I and GnRH-II were determined by radioimmunoassay (RIA) using the appropriate antisera. The elution positions of the synthetic peptides were determined later by application of 1 μg of GnRH-I and of GnRH-II. After thorough washing, a blank run was monitored by RIA to ensure that the column was not contaminated.

Radioiodination and Radioimmunoassay:

Iodination of synthetic GnRH-I or GnRH-II was carried out by using the chloramine-T method[62]. Free iodine was removed on a Sep-Pak C-18 cartridge (Waters Corporation) and the $^{125}I$ labeled peptides were separated from the unlabeled peptides by HPLC. GnRH concentration in the samples were determined by RIA as previously described[56].

Double Fluorescence Immunocytolochemical Analysis:

Peripheral human T-cell were analyzed by double fluorescence immunochemistry using fluorescence microscopy. The T-cells were collected by centrifugation at 1500×g for 10 minutes at 4° C. The cell pellet was gently resuspended in 4% paraformaldahyde solution at $1 \times 10^6$ cells/ml for 10 minutes at room temperature and centrifuged for 10 minutes at 1500×g. The pellet was resuspended again in 80% ethanol at a concentration of $1 \times 10^6$ cells/ml, and aliquots of 200 μl were pipetted onto glass slides that were coated with gelatin and dried for 2 hours on a slide-warmer at 45° C. Dried, unstained, slides were stored at 4 C. Fixed cells were washed (5 minutes×3) with PBS and were permeabilized for 3 minutes with 0.5% Triton X-100, followed by 3 washes with PBS. The cells were then incubated, for 2 hours at room temperature, in a blocking medium (PBS containing 10% normal goat serum, 2% bovine serum albumin (BSA), 1% glycine, 0.5% Triton X-100) to saturate nonspecific binding sites for immunoglobulin G (IgG) followed by the addition of the primary antibodies for 12-15 hours at 4° C. The cells were then washed (5 minutes×3) with 0.1 M of PBS, and incubated for 2 hours at room temperature with either fluorescein or rhodamine-conjugated secondary antibody as follows: goat anti-mouse conjugated to Cy3 (red fluorescence, Jackson, Immunoresearch Laboratories, West Grove, Pa.), goat anti-rabbit conjugated to Oregon Green (green fluorescence, Molecular Probes, Eugene, Oreg.), or both. Fluorescence was visualized by fluorescence microscopy using red and green filters for GnRH-I and GnRH-II, respectively. In order to determine the specificity of the signals we have included several control groups in which the antibodies were preabsorbed with excess (2-100 μg) of GnRH-I or GnRH-II for 24 hours. Additional control sections were incubated without the first antibody or with normal rabbit serum.

Homing of T-Cells In Vivo into Specific Organs of GnRH-I Knockout and Syngeneic Normal Mice:

Normal C3H/HeH mice were sensitized on the abdominal skin with 200 μl of 2% oxazalone dissolved in acetone/olive oil (4:1 vol/vol) applied topically. Ten days later, lymph nodes were removed from the sensitized mice, pooled, and a cell suspension was prepared. The cells were >95% T-cells as evaluated routinely by immunofluorescence staining with anti-TCR mAb. The cells were than fluorescently labeled with BCECF AM (30 minutes 37° C., 7.5% $CO_2$ in a humidified incubator), washed, counted, resuspended in DMEM and inoculated I.P ($15 \times 10^6$ cells/mice) in parallel into GnRH-I knockout (KO) hpg mice and syngeneic aged-matched normal recipients. After 36 h, the spleen, thymus, kidney, liver, bone marrow, and a fixed volume of blood were removed into tubes containing 10 ml PBS, and cell suspensions were prepared from each organ of each individual mouse. Following further dilution in PBS for the kidney (1:3) and liver (1:10), the number of fluorescent cells, as well as the total number of cells in each tube, were counted by flow cytometry (FACSORT).

Homing of GnRH-Treated EL-4 T-Lymphoma In Vivo into Specific Organs of Normal Syngeneic Mice:

Mouse EL-4 T-lymphoma cells were incubated without any further treatment or with either GnRH-I or GnRH-II (10 nM) for 72 h (37° C., 7.5% $CO_2$ in a humidified incubator) and then washed, counted, and fluorescently labeled with BCECF AM (30 minutes 37° C., 7.5% $CO_2$ humidified incubator), as described above.

Normal syngeneic C57BL/6 female recipient mice were then subjected to 300 rad total body irradiation, and several hours later inoculated I.P with $5 \times 10^6$ cells/mouse of either untreated or GnRH-treated EL-4 lymphoma cells. In parallel, samples from the treated and GnRH inoculated EL-4 cells were tested by double immunofluorescence (as described above) for the level of their 67 kD LR and TCRαβ. After 36 hours, the spleen, thymus, kidney, liver, bone marrow, and a fixed volume of blood were removed from the recipient mice into tubes containing 10 ml PBS, and cell suspensions were prepared from each organ of each individual mouse. Following further dilution in PBS for the kidney (1:3) and liver (1:10), the number of fluorescent cells, as well as the total number of cells in each tube, were counted by flow cytometry (FACSORT).

Statistical Analysis:

Statistical significance was analyzed by Student's t test.

EXPERIMENTAL RESULTS

Example 1

Figure 1B:
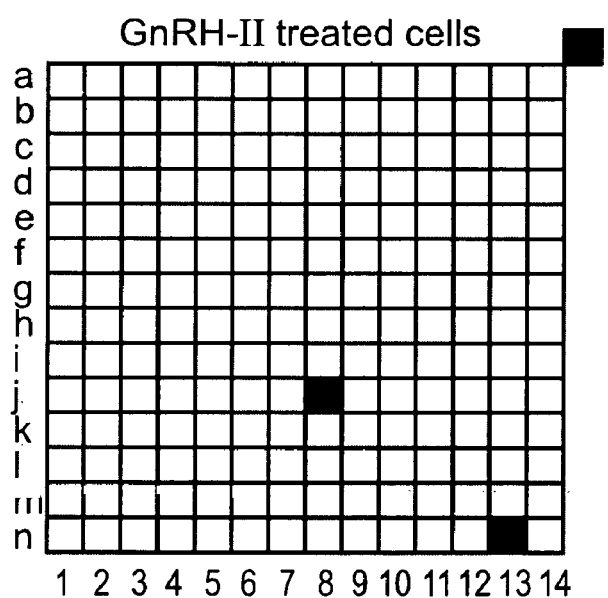

T-Cells Respond to Direct Stimulation of GnRH-II by the De Novo Transcription of a Laminin Receptor mRNA To explore the possible direct effects of GnRH-II on gene expression by T-cells, resting mouse antigen-specific T-cells were exposed to GnRH-II (10 nM) for 24 hours. Poly A+ RNA was prepared from both GnRH-II-treated and untreated cells and reverse transcribed to $^{32}P$-labeled cDNA. Using an Atlas cDNA expression array (i.e. a positively charged nylon membrane spotted with 1200 different cDNAs) for identification of effected genes, the reverse transcribed products were characterized by hybridization to the atlas membranes. The differential pattern of expression between untreated cells and GnRH-II-treated cells was visualized by autoradiography (FIGS. 1A and 1B). The results revealed that GnRH-II induced the over expression of mRNA encoding for several genes, the most prominent being an mRNA encoding for a protein (coordinate n13 in FIGS. 1A and 1B) known as a non-integrin 67 kDa laminin receptor (67 kDa LR, or p67 laminin binding protein, LBP).

Laminin is the predominant glycoprotein of endothelial and epithelial basement membrane and only activated T-cells can bind to it. The known receptors for laminin on the T-cell membrane consist of the well characterized members of integrin family (mainly α6β1) and the non-integrin 67 kDa LR. The 67 kDa LR is over expressed in a variety of tumors and serves as an independent marker for tumor invasion and metastasis. In addition, the 67 kDa was also shown to be the major receptor for Sindbis virus, and for tick-borne encephalitis viruses. Moreover, recent studies indicate that the 37 kDa LR precursor acts as the receptor for prion proteins (PrP), self proteins implicated in the pathogenesis of transmissible spongiform encephalopathies including new variant Creutzfeldt-Jakob disease prion protein in eukaryotic cells.

Figure 1C:
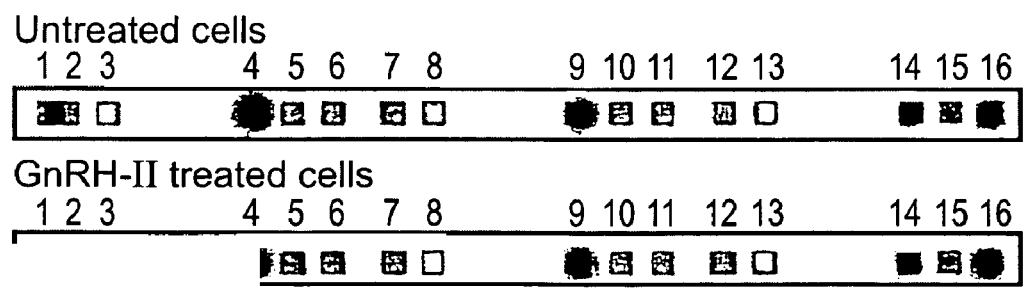

The stimulatory effect of GnRH-II on the 67 kDa LR was specific since the transcription of many other genes including the house-keeping gene nucleoside diphosphate kinase B (FIGS. 1A and 1B, coordinate j8) were not affected by GnRH-II stimulation. FIG. 1C represents the control hybridizations for the untreated cells (upper panel) and GnRH-II treated cells (lower panel), further demonstrating the absence of GnRH-II stimulatory effect on the transcription of additional housekeeping genes.

To compare between GnRH-II activation, taking place via putative specific GnRH-II receptors on T-cells, and 'classical' antigenic stimulation, taking place via the TCR the mouse antigen-specific T-cell line used above was stimulated with its respective antigen, in parallel to the stimulation by GnRH-II alone (10 nM). Using the Atlas cDNA expression array, it was possible to identify genes whose expression was up- or down-regulated by the two stimulation pathways, as compared to untreated cells. The results revealed clear differences between antigenic and direct neurohormonal stimulation (data not shown). Thus, for example, the antigenic stimulation of the mouse T-cells upregulated the expression of numerous genes, among them the CD4 antigen and the cell cycle gene Cyclin D2, and downregulated the expression level of other genes, such as the thymus cell antigen 1. The direct stimulation by GnRH-II, however, did not affect the synthesis of these specific genes, but rather of others. Taken together, these results indicate that GnRH-II directly stimulates T-cell activity, resulting in a GnRH-II-specific pattern of gene transcription.

Example 2

Figure 1D:
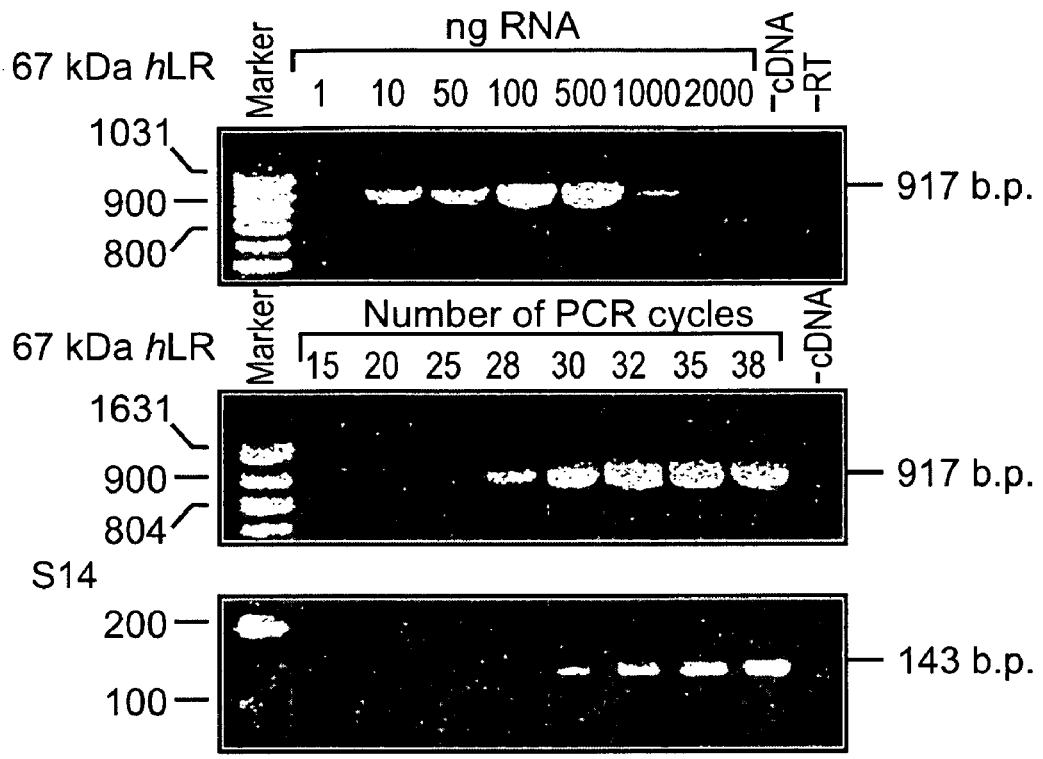
FIGS. 1D-F illustrate the specific activation of 67 kDa laminin receptor expression in human peripheral T-cells by GnRH-I and GnRH-II, employing quantitative RT-PCR assay of the 67 kDa LR and S14 transcripts obtained from peripheral human T-cells. The upper panel of FIG. 1D demonstrates the presence of the ethidium bromide staining LR amplification products using increasing amount of total peripheral T-cell RNA ranging from 1 to 2000 ng. PCR was performed for 30 cycles. In the middle and lower panels 50 ng of the total RNA was reacted, and PCR was performed for increasing number of amplification cycles. The ethidium bromide bands corresponding to the amplified 67 kDa LR transcripts were quantified by AlphaEase program (Alpha Innotech, San Leandro, Calif., USA). The average relative signal of LR and S14, correlate with the number of PCR cycles and are demonstrated by the graph to the right of FIG. 1D. Subsequent experiments were carried out with 50 ng of total RNA and PCR for 28 cycles.
Figure 1D:
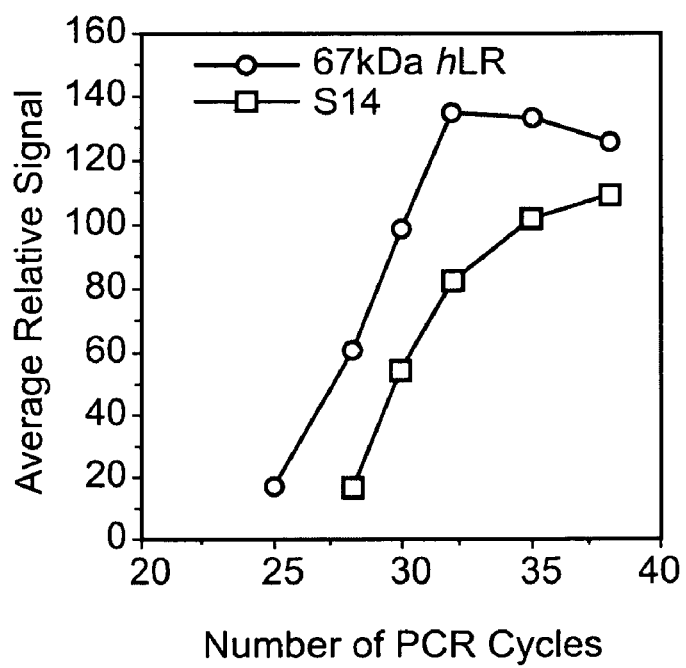

Both GnRH-I and GnRH-II Increase the Expression Level of the 67 kDa Laminin Receptor in Normal Human T-Cells To confirm the results of the atlas cDNA expression array, the level of expression of the 67 kDa LR was analyzed by quantitative RT-PCR in normal human T-cells. Following calibration of the experimental conditions for the quantitative RT-PCR assay (FIG. 1D), the level of the laminin receptor mRNA was determined in normal human T-cells stimulated for increasingly longer periods (1 to 48 hours) with either GnRH-II or GnRH-I. The results, presented in FIGS. 1E and 1F for GnRH-I and GnRH-II-treated cells respectively, show that the LR mRNA levels in the GnRH-II and GnRH-I treated cells were significantly altered, in a time-dependent manner, when compared to untreated cells. The radioactive bands were quantified using a phosphorimager and normalized according to S-14 (ribosomal protein gene) values. The results, presented as fold increase over control group values, are shown in the lowest panels of FIGS. 1E and 1F, respectively.

As can be observed in these histograms, both GnRH-II and GnRH-I significantly elevated the LR mRNA level, although to different extents: 10 fold increase for the GnRH-II, and 3 fold increase for GnRH-I. Moreover, although the effects of GnRH-II and GnRH-I each presented a different time course (FIGS. 1E and 1F), both required 12-24 hours to significantly elevate the LR mRNA level. These results are consistent with the previously reported peak levels of the 67 kDa LR mRNA expression 18-36 h following the 'non physiological' activation of normal peripheral blood T-cells by phorbol dibutyrate or ionomycin.

Example 3

Figures 2A, 2B, 2C:
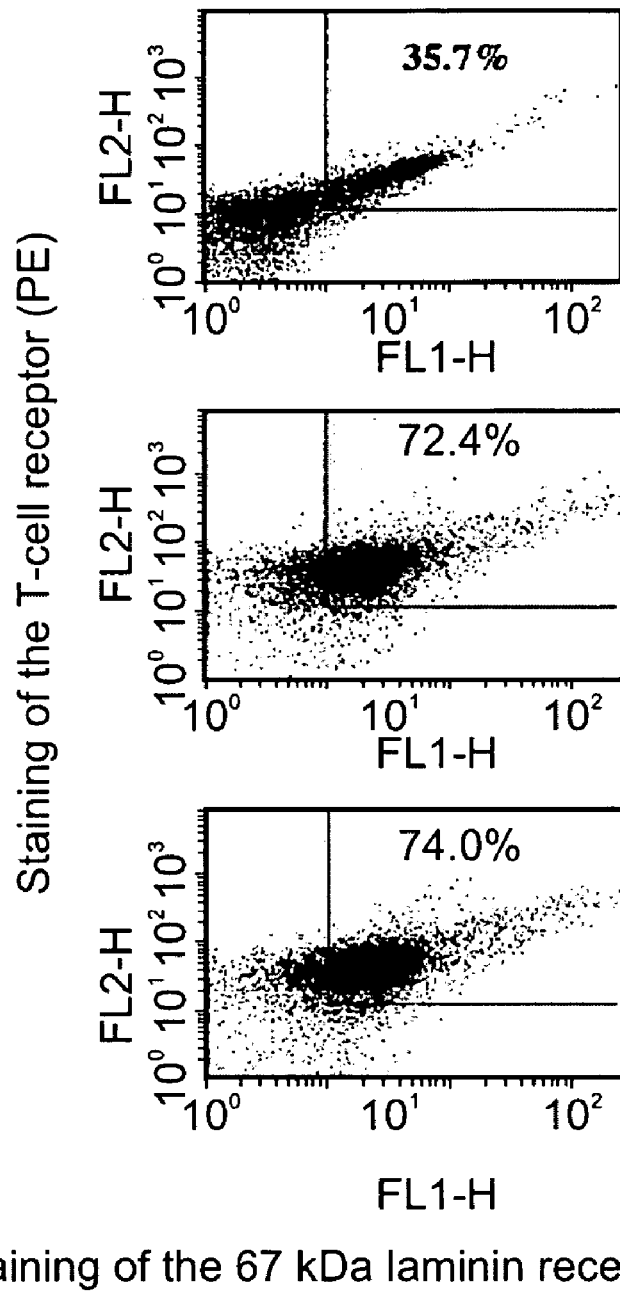
FIGS. 2A-C illustrate the GnRH-I and GnRH-II induced surface expression of the 67 kDa LR on normal human T-cells. The plots represent the distribution of fluorescent antibody binding T-cells following FACS separation. Freshly isolated normal human T-cells were-preincubated (48 hours, 37° C.) in medium (FIG. 2A) or with 10 nM of either GnRH-I (FIG. 2B) or GnRH-II (FIG. 2C) and were then subjected to double immunofluorescence staining, using a mouse anti-67 kDa LR mAb (MLuC5) followed by an FITC-conjugated anti-human IgG, and phycoerythrin (PE)-conjugated anti-TCRαβ mAb. The abscissa shows the FITC scale, corresponding to the staining of the anti-LR mAb, while the ordinate shows the PE scale, corresponding to TCR staining. The quadrants: lower left-double negative (LR− and TCR−); upper left-TCR positive and laminin receptor negative, lower right-LR positive and TCR-negative, upper right-double positive (LR+ and TCR+). These results indicate that a physiological concentration of either GnRH-I or GnRH-II significantly increased the surface expression of the 67 kDa LR on normal human TCR-positive cells.

GnRH Augments the Surface Expression of the 67 kDa Laminin Receptor on Normal Human T-Cells To determine whether GnRH-II and GnRH-I trigger not only the gene transcription but also the surface expression of the 67 kDa LR, normal human T-cells were treated with either GnRH-II or GnRH-I for 18-66 h and subjected to double immunofluorescence staining using a monoclonal antibody (mAb) that is specific for the 67 kDa LR, and a phycoerythrin (PE)-conjugated anti-TCRαβ mAb (to confirm the T-cell origin of the cells). FIGS. 2A-2C show the staining for the untreated, GnRH-I treated and GnRH-II treated T-cells, respectively. The FACS profiles can be interpreted by division according to four categories: 1. Negative staining for both mAbs (double negative, lower left quadrant); 2. Single positive staining only with the anti-LR mAb (lower right quadrant), 3. Single positive staining only with the anti-TCR mAb (upper left quadrant); 4. Double positive staining with both mAbs (upper right quadrant). As can be observed in FIGS. 2A-2C, one clearly detects a 67 kDa LR and TCR positive cell population that is doubled following GnRH-I or GnRH-II treatment (from 35.7% to 72.4% and 74.3% respectively). In different experiments, each using freshly isolated T-cells from a different human donor, both GnRH II and GnRH I repeatedly elevated the laminin receptor expression level, but the magnitude of elevation varied within a range of 6-40%. Such variations between T-cell populations originating from different donors are often observed in respect to various T-cell features and functions.

The results of these experiments indicate that direct exposure of normal resting human T-cells to either GnRH-II or GnRH-I, at the relatively low physiological concentration of 10 nM, significantly increases the surface expression of the 67 kDa laminin receptor that has been previously described to be expressed only on a small subpopulation of activated T-cells.

Example 4

GnRH-II and GnRH-I Stimulates Human T-Cells Via Two Distinct Receptors

Figures 2D, 2E:
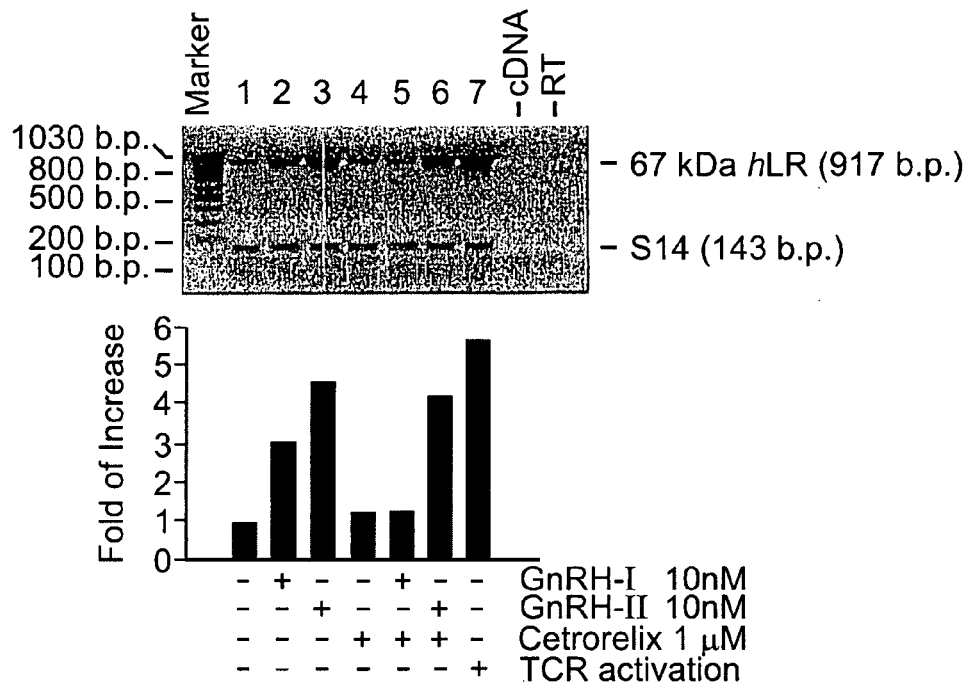
FIGS. 2D and 2E demonstrate selective blockage by GnRH-I receptor antagonist Cetrorelix of GnRH-I-induced, but not GnRH-II-induced gene and surface expression of the 67 kDa LR.

To gain insight into the specific receptors on the T-cell surface via which GnRH-I and GnRH-II induce the 67 kDa LR expression, the ability of the specific GnRH-I receptor antagonist Cetrorelix (SB-75) 27 to block GnRH-I and GnRH-II-induced elevation of the 67 kDa LR expression was measured. Of note, the neuropeptide GnRH-II was only recently discovered in mammals, thus specific antagonists for this neuropeptide have yet to be developed. The results demonstrate that the GnRH-I receptor antagonist indeed blocked the GnRH-I induced upregulation in the gene expression (FIG. 2D) and surface expression (FIG. 2E) of the 67 kDa LR, indicating that GnRH-I conveys an activating effect on T-cells via its specific GnRH-I receptor, which is likely to be similar to the GnRH-I receptor on various other cell types known as 'classical' GnRH-I targets. Importantly, the GnRH-I receptor antagonist did not block the effects of GnRH-II (FIGS. 2D and 2E), indicating that GnRH-II and GnRH-I stimulate T-cells via two distinct receptors.

To confirm previous studies showing that upon TCR stimulation of human T-cells the 67 kDa LR is upregulated, a fresh normal human T-cell population was reacted with anti-CD3+ anti-CD28 mAbs to induce a TCR-like activation, and compared with GnRH direct stimulated cells by PCR. The results show that the TCR activation of the normal human T-cells indeed causes a marked upregulation in the mRNA levels (FIG. 2D, lane 8) and surface expression (FIG. 2E) of the 67 kDa LR.

Finally, the possibility that the stimulation of normal human T-cells by either GnRH-I, GnRH-II or anti-CD3+ anti-CD28 mAbs, elevates not only the non-integrin 67 kDa LR but also the expression level of the VLA-6 laminin-binding integrin (known to be expressed on T-cells) was investigated. Double immunofluorescence staining with anti-VLA-6 and anti-TCR mAbs showed that the untreated human T-cells have a high basal expression level of the VLA-6 integrin (about 75% of the cells showing double positive staining) which was unaffected by any of the abovementioned stimuli (data not shown). Thus stimulation by GnRH-II and GnRH-I (as well as TCR-activation) primarily increases the protein surface expression of the non-integrin 67 kDa LR, but not of the VLA-6 laminin binding integrin.

Example 5

GnRH Drives T-Cells into Adhesion to Laminin

To study the functional consequences of the increase in the 67 kDa LR expression level following GnRH stimulation, the ability of GnRH-treated normal human T-cells to adhere to laminin was assessed. It is widely accepted that only activated T-cells can bind to components of the basement membrane and extracellular matrix, such as laminin. Thus, the adhesion to laminin-coated microtiter plates of GnRH-treated cells was compared to that of untreated cells (negative control), and cells treated with a PKC-activating phorbol ester (a very potent non-specific T-cell activator: PMA, positive control). In parallel, increasing numbers of untreated cells were seeded on separate plates, in order to establish a standard curve, enabling the relation of results obtained in units of fluorescence intensity (OD) to actual number of cells.

Figure 3A:
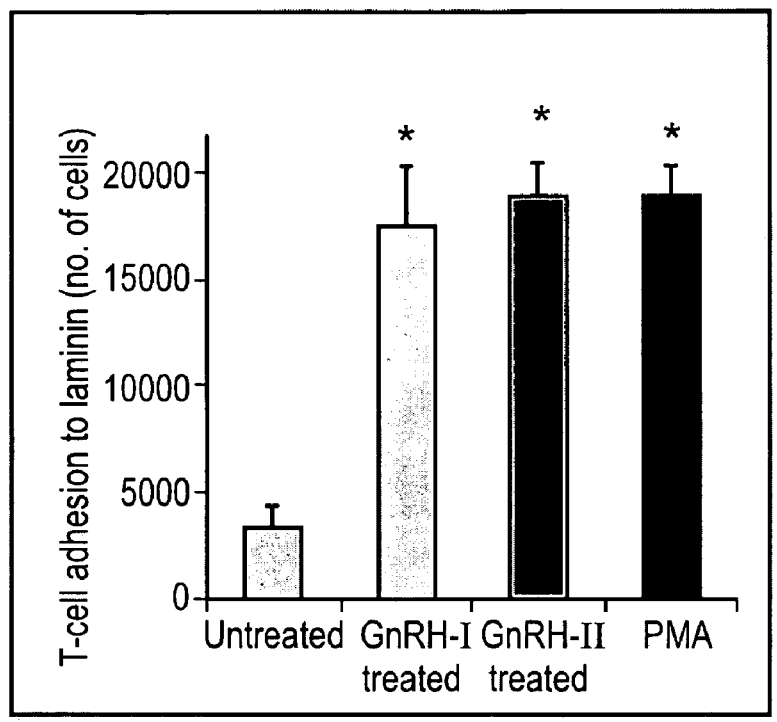
FIGS. 3A-B illustrate the GnRH-I and GnRH-II induced T-cell adhesion to laminin. Normal human T-cells purified from blood samples of different human donors were pretreated (48 hours at 37° C.) with either GnRH-I or GnRH-II (10 nM) and then tested for their adhesion to laminin.
Figure 3B:
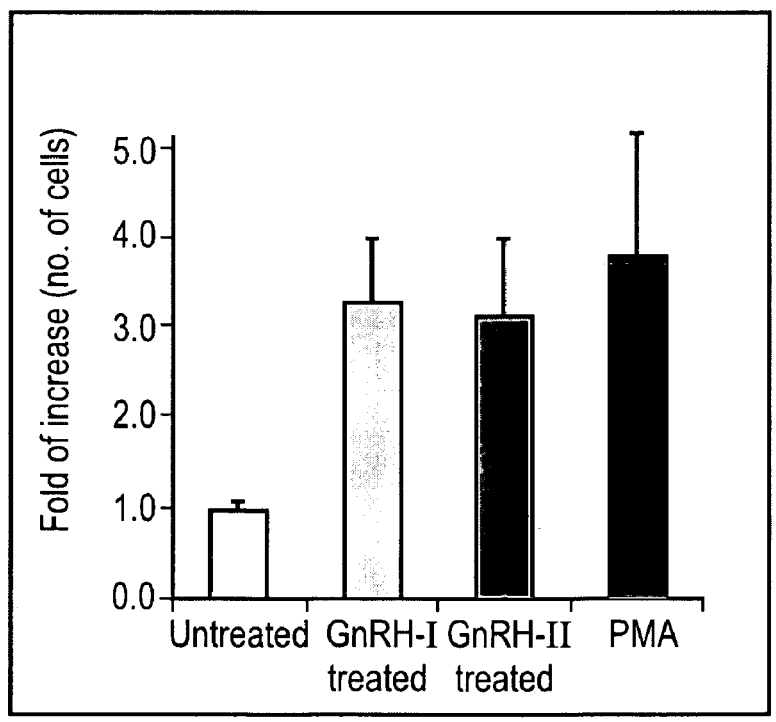

FIG. 3A shows the results of a representative adhesion experiment, demonstrating the numbers of fluorescent labeled T-cells adhering to laminin, while FIG. 3B shows the mean fold increase in adhesion to laminin of four independent experiments, performed with fresh human T-cells from four different donors. The results clearly indicate that GnRH-II and GnRH-I endow T-cells with ability to adhere to laminin, as markedly as does PMA.

Example 6

GnRH Augments the In Vitro Chemotactic Migration of T-Cells

Figure 3C:
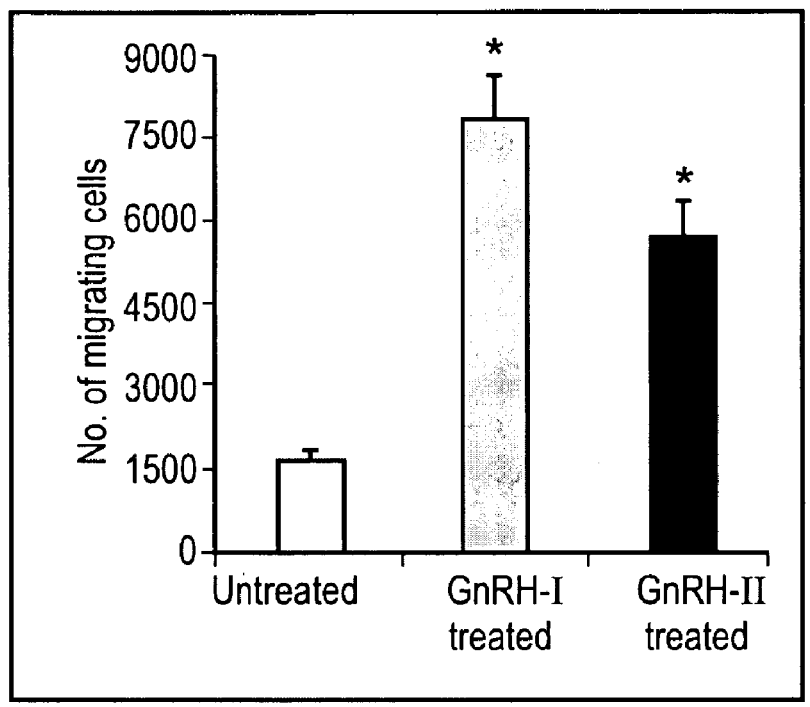
FIGS. 3C and 3D illustrate the GnRH-I and GnRH-II induced migration of human T-cells towards the chemokine SDF-1. Human T-cells purified from fresh blood samples of different human donors were pretreated (>18 h 37.degree. C.) with either GnRH-I or GnRH-II (10 nM), labeled with a fluorescent dye, and tested for their migration towards the chemokine SDF-1. The cells in each experimental group were counted by FACSORT.
Figure 3D:
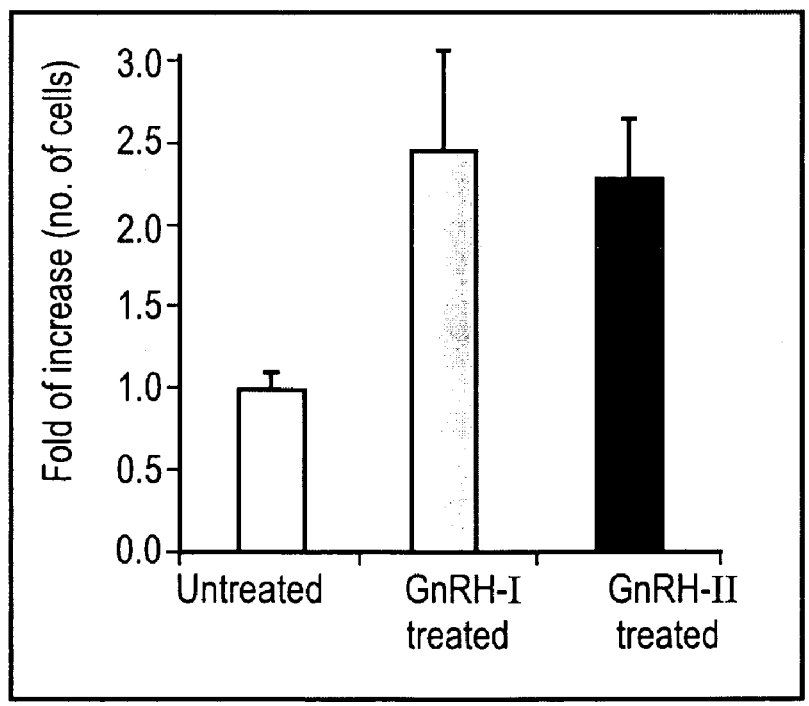

Adhesion of T-cells to components of the basement membrane is a crucial step in the series of events that eventually enable T-cells to migrate and extravasate from the blood stream to specific tissues. T-cells, which constantly move randomly, exhibit the crucial ability to move in a directional manner by responding to remotely secreted chemoattractants, via specific surface-expressed chemokine receptors. To determine whether GnRH can induce T-cells to migrate towards a chemoattractant, we made use of the Boyden chamber migration assay and scored the number of fluorescence-labeled normal human T-cells which migrated from a medium-containing upper chamber to a chemoattractant-containing lower chamber. The chambers were separated by filters pre-coated with laminin, thus making the adhesion to laminin a necessary (but not sufficient) step for the migration to the lower chamber. The stromal cell-derived factor-1 (SDF-1) chemokine, which has a specific receptor on the T-cell surface termed CXCR4, was used as a chemoattractant source. The number of migrating T-cells to chemokine-devoid lower chambers constituted background (BG) migration. The results of one representative experiment (FIG. 3C), expressed as the number of migrating cells, and of four independent experiments (FIG. 3D), expressed as the mean fold increase of migrating cells, indicate that pre-treatment of normal human T-cells for at least 18 h with either GnRH-II or GnRH-I, significantly augments their migration towards the chemoattractant SDF-1.

Example 7

Figure 4A:
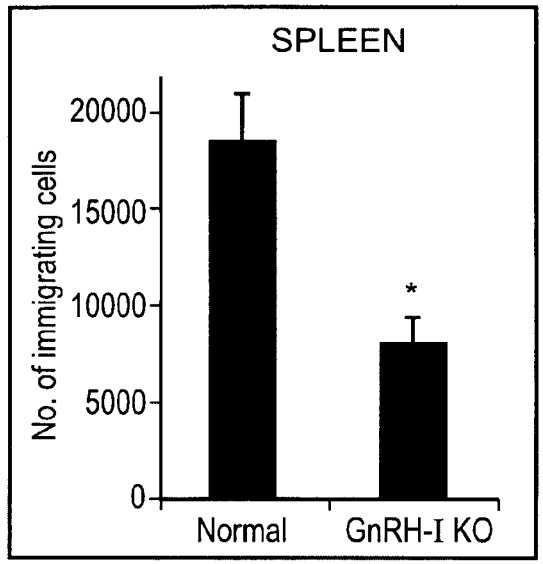
FIGS. 4A-4F illustrate the reduced in vivo immigration of normal untreated T-cells into the spleen and kidney of GnRH-I deficient (knockout) mice, compared to normal syngeneic mice. T-cells originating from lymph nodes of normal C3H/HeH mice were pooled, loaded with a fluorescent dye, and inoculated intraperitoneally ($15 \times 10^6$ cells/mice) to GnRH-I deficient knockout (KO) hpg mice as well as to normal C3H/HeH syngeneic age-matched recipients. After 24 h, the spleen, thymus, kidney, liver, bone marrow, and a fixed volume of blood were removed into tubes containing 10 ml PBS, and cell suspensions were prepared from each organ of each individual mouse. Following further dilution in PBS for the kidney (1:3) and liver (1:10), the number of fluorescent cells, as well as the total number of cells in each organ was counted by flow cytometry (FACSORT). The results shown in the figures represent one out of two independent experiments (yielding exactly the same pattern of results).
Figure 4B:
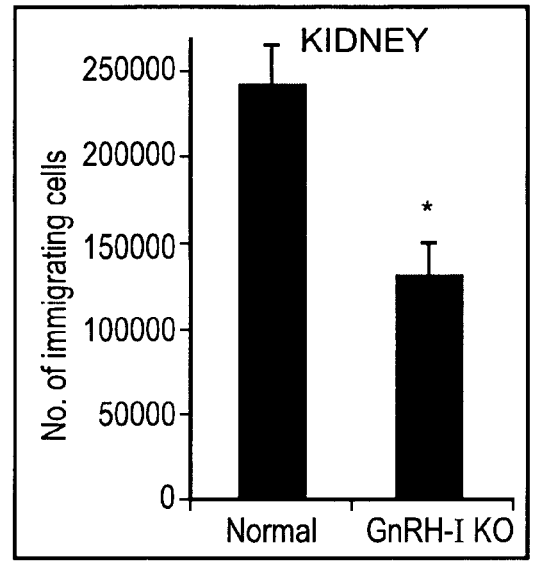
Figure 4C:
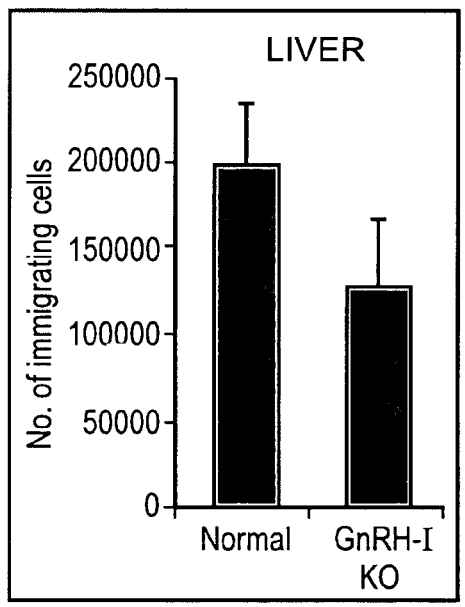
Figure 4D:
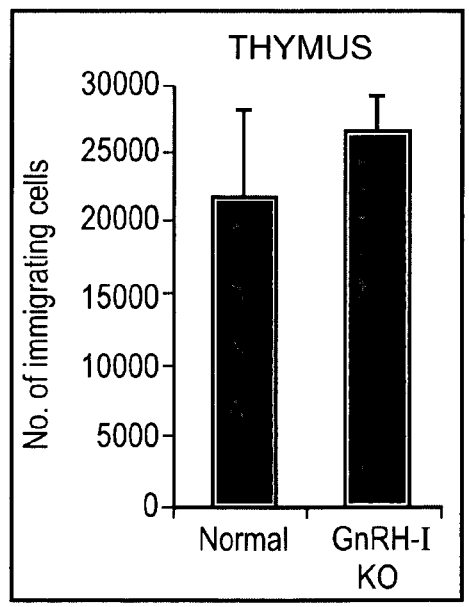
Figure 4E:
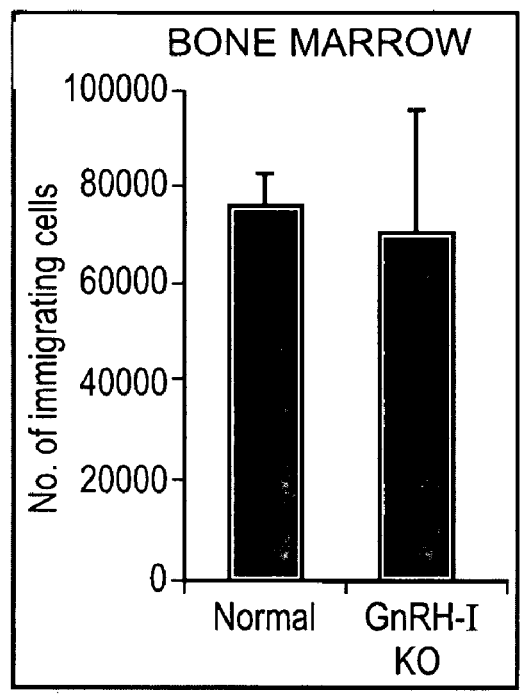
Figure 4F:
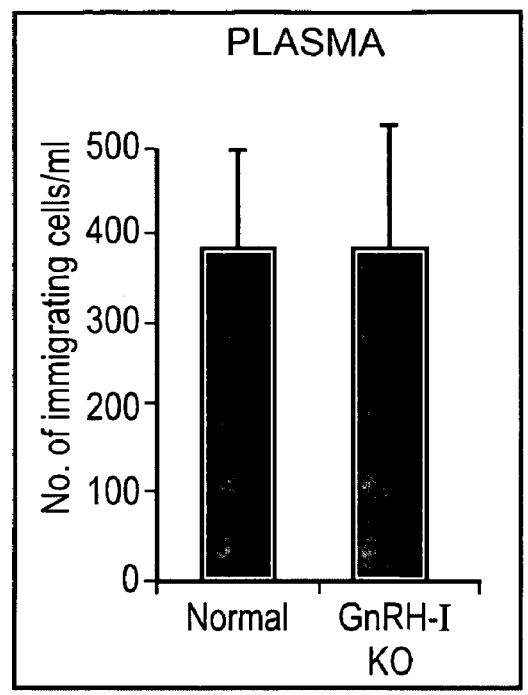

Normal T-Cells Exhibit In Vivo Reduced Entry into the Spleen and Kidney of GnRH-I Knockout Mice, Compared to Normal Syngeneic Mice To investigate whether the direct interactions between GnRH and T-cells have functional consequences under in vivo conditions, the migration of mouse T-cells into specific organs was assessed in GnRH-I deficient knockout (KO) mice compared to normal syngeneic mice. T-cells originating from lymph nodes of normal donor C3H/HeH mice were pooled, loaded with a fluorescent dye (BCECF AM), and inoculated in parallel to GnRH-I deficient (KO) hpg mice and to syngeneic age-matched normal C3H/HeH mice. Thirty six (36) hours later, several organs were removed from the recipient mice, including the spleen, thymus, kidney, liver, bone marrow and a fixed volume of blood. Cell suspensions were prepared from the individual organs of each mouse separately, and the number of fluorescent-labeled, as well as the number of non-labeled cells in each organ was counted by flow cytometry. The results, obtained in two independent experiments, of which only one is presented (FIGS. 4A-4F), show that passively transferred T-cells were detected in all organs of GnRH-I deficient KO mice and normal mice. However, a significantly lower number of cells entered the spleens (FIG. 4A) and kidneys (FIG. 4B) of the GnRH-I deficient KO mice compared to migration into spleens and kidneys of normal syngeneic age-matched mice. Thus, while a mean of 18,575±2400 inoculated BCECF AM-labeled T-cells entered the spleen of normal mice (n=4), only 7975±6546 entered the spleen of GnRH-I deficient KO mice (P=0.014), constituting a 57% reduction. Likewise, while the kidneys of normal mice contained 241875±23,892 labeled immigrating T-cells, the kidneys of the GnRH-I deficient KO mice contained only 131325±18928 (P=0.01) cells, representing a 46% reduction. Interestingly, no significant differences were observed in the number of labeled T-cells detected in the thymus, liver, bone marrow and plasma of normal and GnRH-I deficient KO mice (FIGS. 4C-4F). A similar pattern of results is obtained when the degree of T-cell entry into specific organs in normal and GnRH-I deficient KO mice is expressed as the ratio of labeled immigrating cells/total number of cells in each specific organ, rather than only by the net number of immigrating cells. Considered together, these results indicate that GnRH-I is an important factor in the regulation of in vivo T-cell migration and entry into specific organs.

Example 8

The EL-4 T-Cell Lymphoma Expresses the 67 kDa Laminin Receptor, Upregulates its Level and Exhibits Increased Entry In Vivo into Specific Organs in Response to GnRH Stimulation Previous studies have shown the expression of the ~67 kDa LR in several T-cell lymphoma and leukemia lines. To study the possible relevance of GnRH-T cells interactions to cancer, expression of the 67 kDa LR gene in the highly metastatic EL-4 mouse T-lymphoma cell line was assessed. In addition, the effect of stimulation by GnRH-I and GnRH-II on the level of surface 67 kDa LR in EL-4 lymphoma cells, and the extent of the lymphoma entry in vivo into specific organs was investigated.

EL-4 T-lymphoma cells, having a cell surface phenotype of: $CD2^+3^+4^-8^-45^+$ TCR alpha beta $(\alpha\beta)^+$ gamma delta $(\gamma\delta)^-$, are widely used to investigate the properties of lymphoma/leukemia cells and their tumor spreading behavior.

Figure 5A:
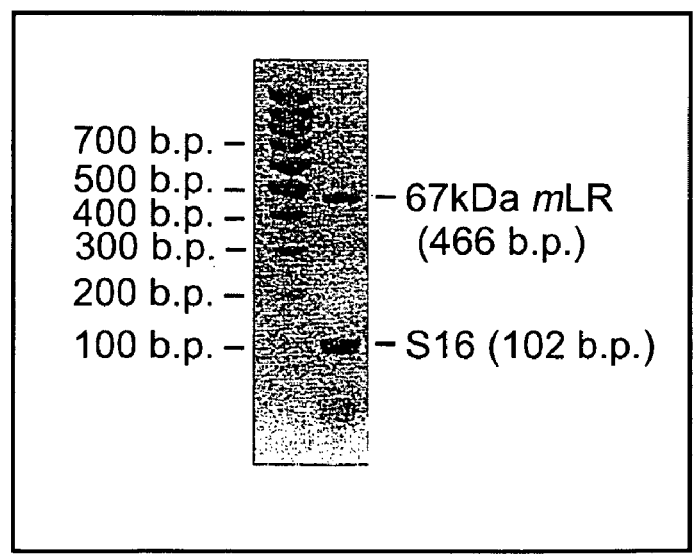
FIGS. 5A-5I demonstrate the expression of the 67 kDa LR in EL-4 T-lymphoma cells, their sensitivity to GnRH stimulation and the enhanced entry of GnRH treated lymphoma cells into the bone marrow of recipient mice.
Figure 5B:
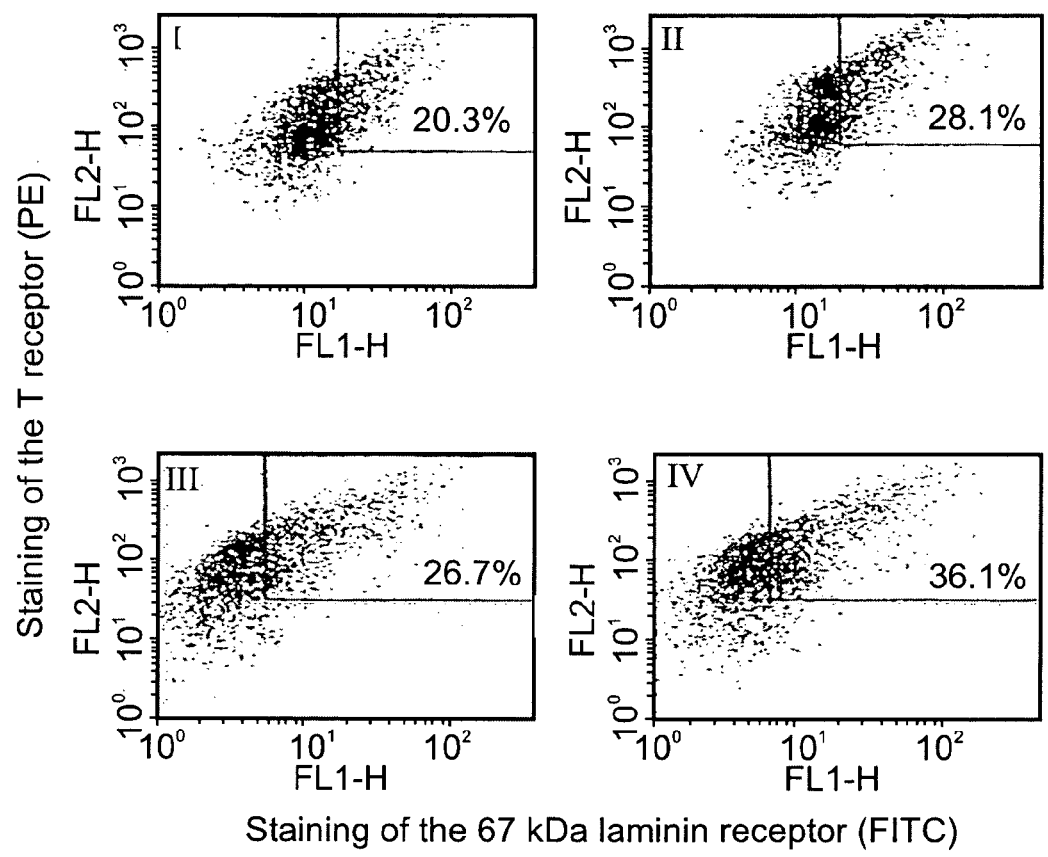

FIG. 5A demonstrates that the EL-4 T-cell lymphoma expresses the 67 kDa LR mRNA, as detected by RT-PCR. Double immunofluoresence staining, using the anti-human (not tested thus far on mouse cells) 67 kDa LR mAb and an anti-mouse TCR $\alpha\beta$ mAb confirmed the surface expression of the 67 kDa LR on TCR $\alpha\beta$+ EL-4 cells, and showed that its level increases following treatment with GnRH-I (FIG. 5B—panel II compared to 5B—panel I) or GnRH-II (FIG. 5B—panel IV compared to 5B—panel III). A comparable elevation in the 67 kDa LR mRNA following treatment of the EL-4 cells with GnRH was observed by RT-PCR (data not shown).

To assess whether exposure of EL-4 T-lymphoma cells to GnRH modulated their immigration and organ invasion profiles in vivo, the EL-4 cells were treated ex vivo with GnRH-I or GnRH-II (10 nM, 48 h), loaded with a fluorescent dye, and inoculated into normal syngeneic C57BL/6 (H-2b) recipient mice. After 48 hours, the spleen, thymus, kidney, liver, bone marrow, and a fixed volume of blood were removed, individual cells suspensions were prepared and the number of labeled immigrating cells, as well as the total number of cells present in each organ (labeled+non-labeled) was counted by flow cytometry.

Figure 5C:
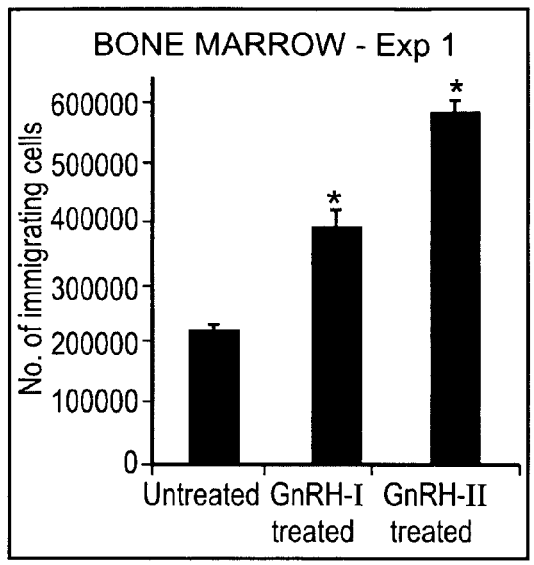
Figure 5D:
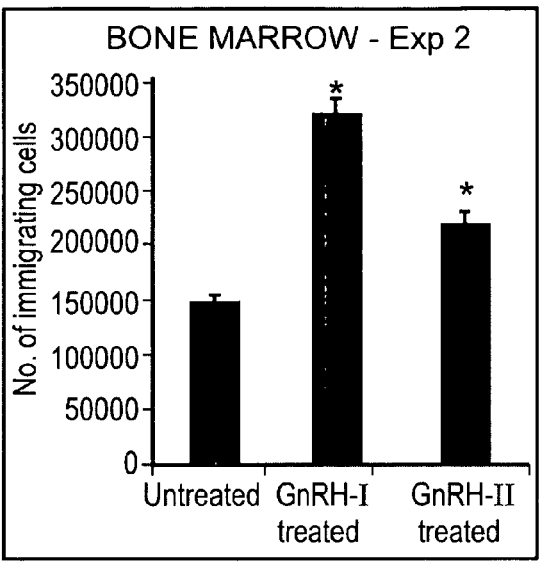

The results of two independent experiments demonstrated that pre-treatment with GnRH-I or GnRH-II increased the migration of the T-lymphoma cells into the bone marrow, in comparison to untreated cells (FIGS. 5C and 5D). Thus, for example, the mean number of EL-4 labeled cells detected in the bone marrow of mice (n=5) innoculated with untreated, GnRH-I- or GnRH-II-treated EL-4 cells were 149825±8424, 321400±15165 (p=0.007), and 219280±14003 (p=0.026) respectively (FIG. 5D), representing an increase in entry of 115% (GnRH-I stimulation) and 46% (GnRH-II stimulation) over the untreated control cells.

Figure 5E:
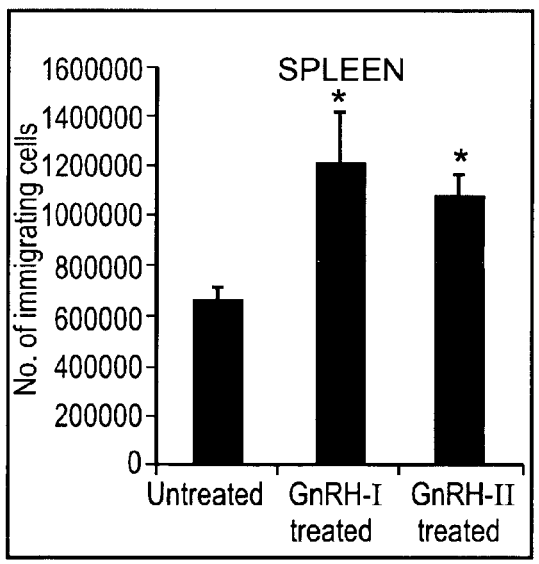
Figure 5F:
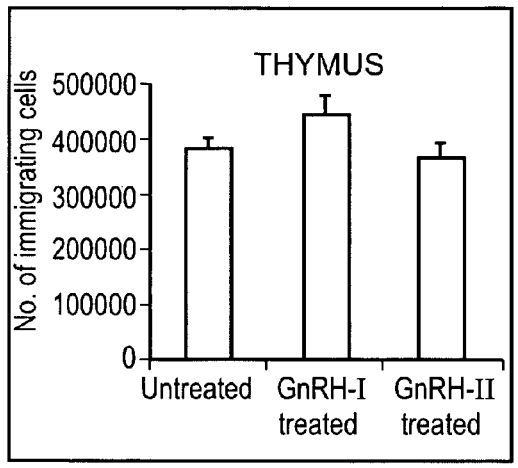
Figure 5G:
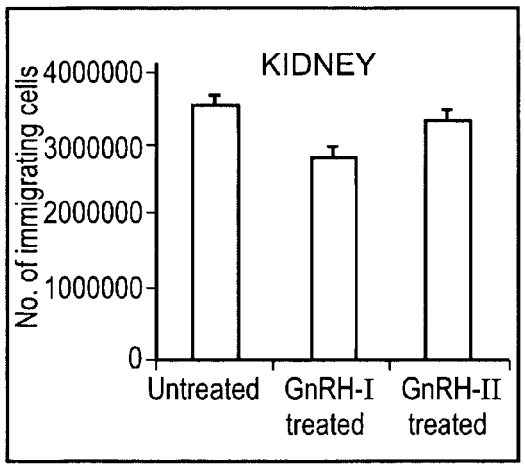
Figure 5H:
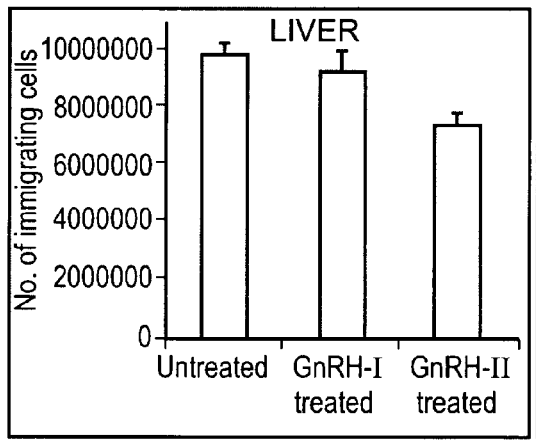
Figure 5I:
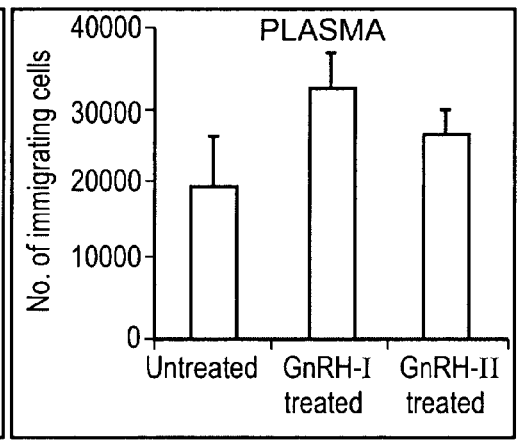

Exposure of the EL-4 cells to GnRH-II and GnRH-I also resulted in their significant enhanced entry into the spleen (FIG. 5E). In contrast to the invasion of the lymphoma into the bone marrow and spleen, GnRH-I and GnRH-II stimulation did not affect either the level of EL-4 cells entry into the thymus, kidney and liver, or their number in the plasma (FIGS. 5F-5I). This is consistent with a previous study showing that EL-4 lymphoma cells metastasize specifically to the spleen and bone marrow. Moreover, the presence of EL-4 cells in the spleen or bone marrow correlates with a total absence of natural killer (NK) activity in these organs. Thus, metastatic EL-4 cells appear to have a direct and irreversible suppressive effect on the generation of NK activity by the spleen or bone marrow, and may significantly impair the ability of the organism to combat the tumor.

Taken together, these results indicate that direct stimulation of T-lymphoma cells by GnRH-I or GnRH-II leads to their enhanced migration and entry into the spleen and bone marrow, and potentially to increased metastatic T-cell derived tumor spread and death.

Example 9

T-Cells Produce GnRH-II and GnRH-I

Production and secretion of GnRH-I and II by T-cells themselves, enabling their self-modulation, and/or influencing of other, neighboring cells would constitute autocrine/paracrine regulation of neuroimmune function. Indeed, normal human T-cells were previously shown to produce GnRH-I. In addition, production of various other neuropeptides, among them VIP, has been demonstrated in various immune cells.

Figure 1E:
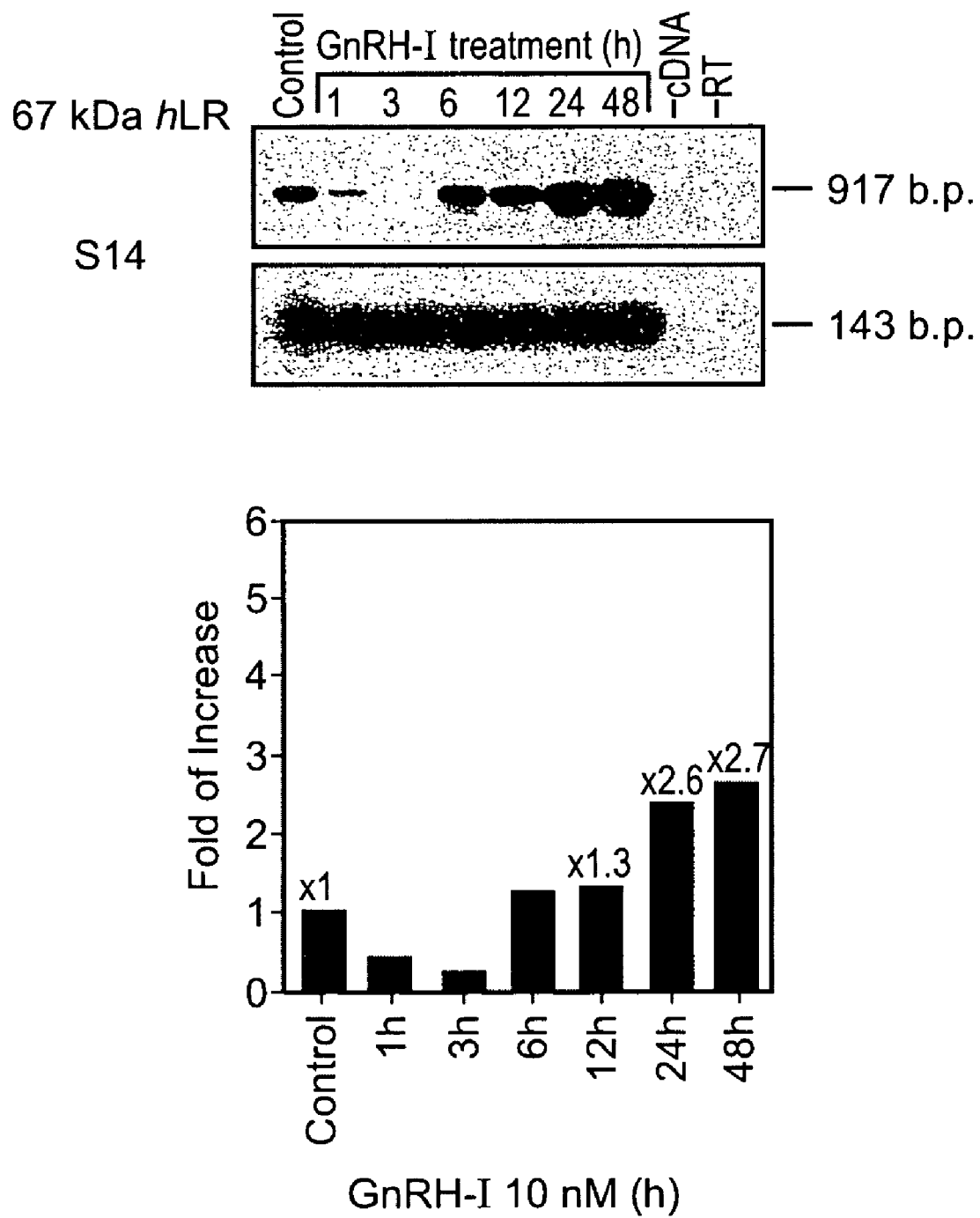
Figure 1F:
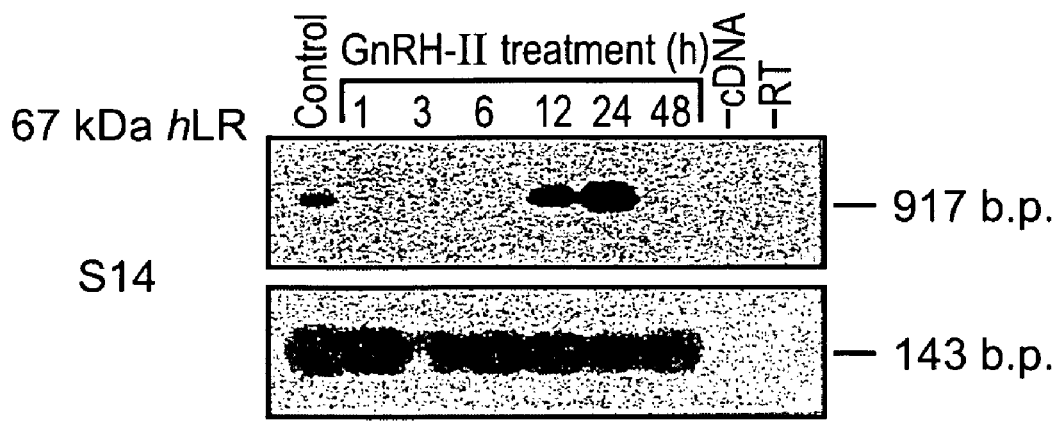
Figure 1F:
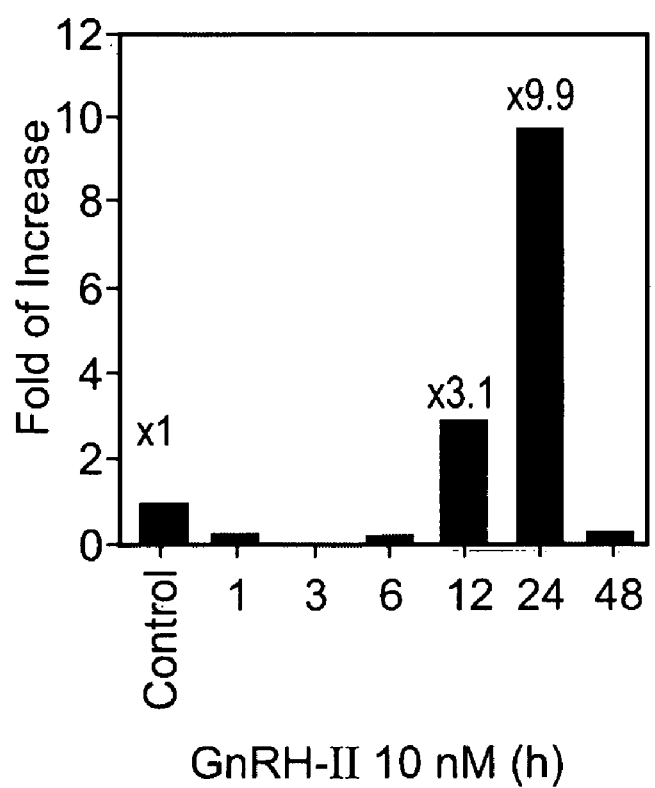
Figure 6A:
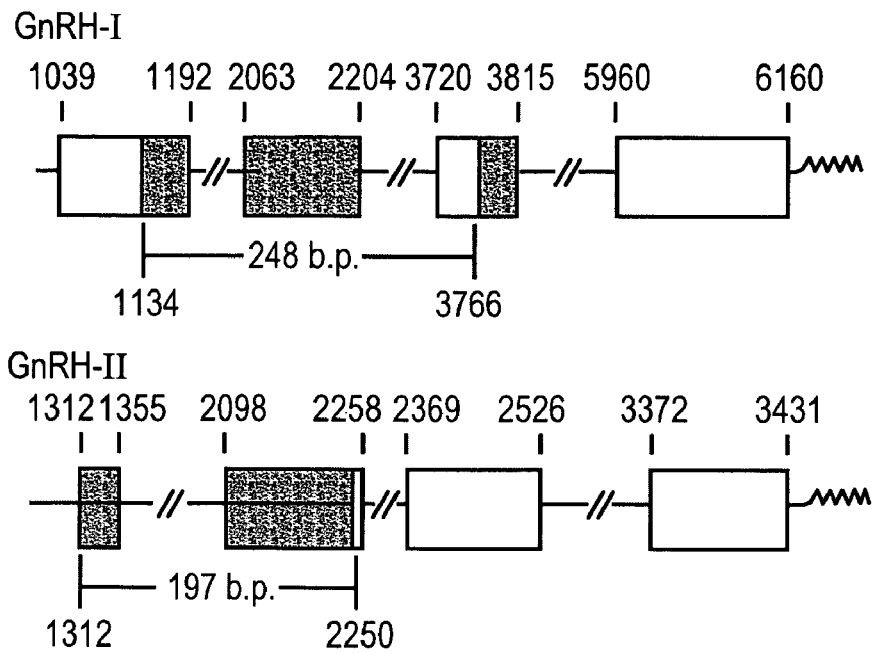
Figure 6B:
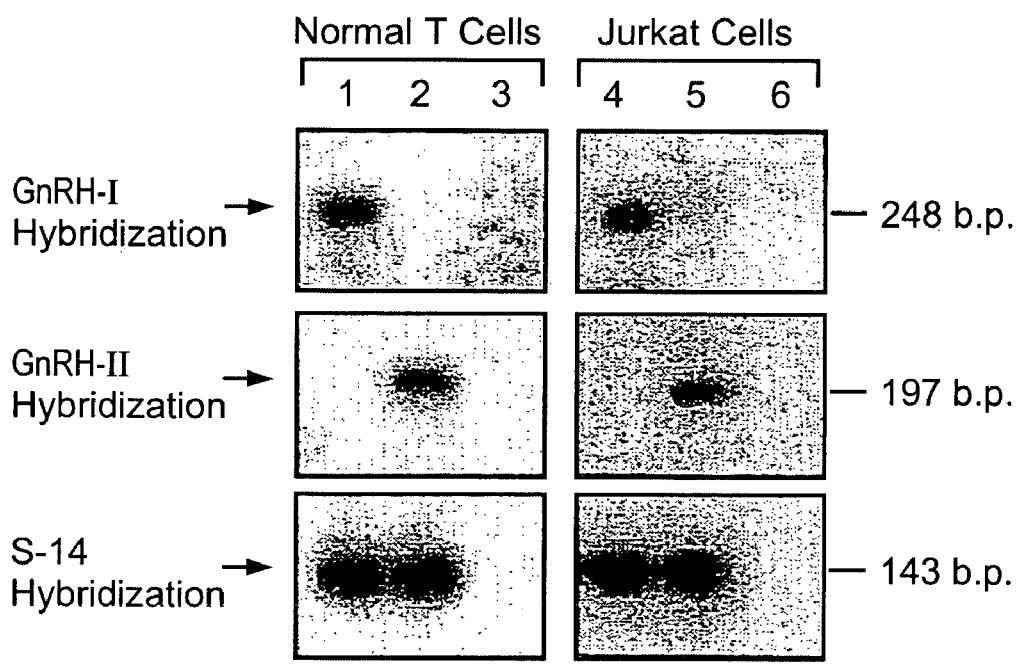

GnRH-II production in T-cells was investigated using the following strategy:

(a) RT-PCR: Total RNA preparations derived from peripheral human T-cells and from leukemia Jurkat T-cell line were reverse transcribed to generate cDNA pools. The cDNA products were used as templates to polymerase chain reactions (PCR) using specific primers for GnRH-I, GnRH-II and for the ribosomal protein S14 (which served as an internal control). Sense and antisense primers were selected to be located on different exons, both for GnRH-I and GnRH-II, in order to avoid false positive results, caused by DNA contamination (FIG. 6A). The RT-PCR and Southern hybridization demonstrate that GnRH-I (FIG. 6B, upper panel) and GnRH-II (FIG. 6B, middle panel) are both expressed in the peripheral human T-cells and in the Jurkat cell line. The ribosomal protein S14 that served as an internal control was expressed, as expected, in all cDNA preparations (FIGS. 1E and 1F, lower panels). The appropriate T-cells cDNA fragments of GnRH-I and GnRH-II were isolated from the agarose gel, subcloned into pGEM-T vectors and the nucleotide sequences were determined using the T7 primer. These sequences were compared to those in the gene bank database and were found to be identical to the known sequences of GnRH-I (FIG. 6C) and GnRH-II (FIG. 6D).

Figure 7A:
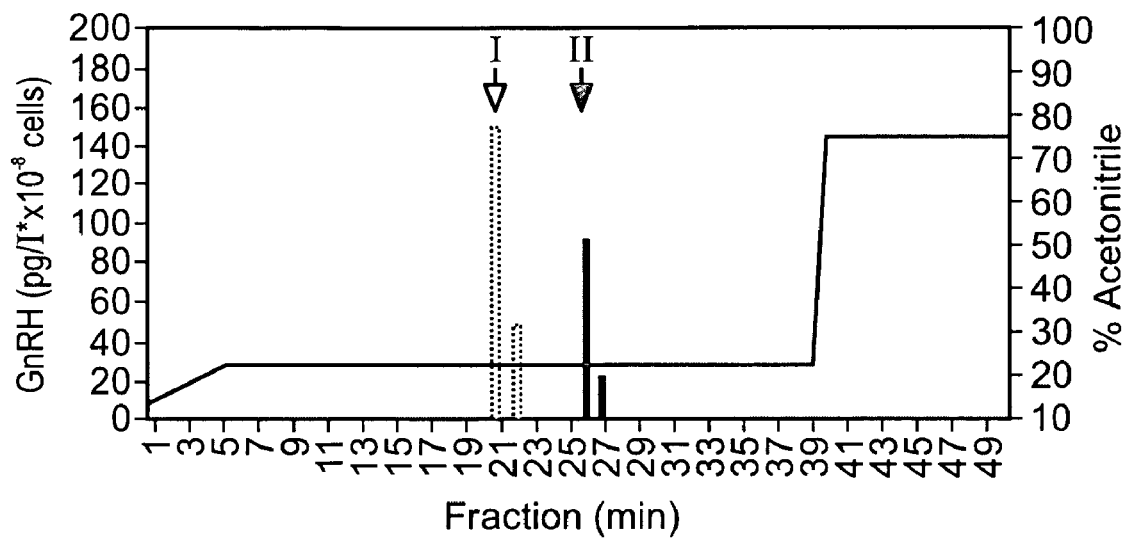
FIGS. 7A and 7Bi-7Bviii demonstrate the production of the neuropeptides GnRH-II and GnRH-I in human T-cells.

(b) HPLC followed by radioimmunoassay: acid extracts of Jurkat T-cells were eluted through RP-C18 columns by HPLC using an isocratic elution program 10 that separates synthetic GnRH-I (FIG. 7A, open arrow) from GnRH-II (FIG. 7A, black arrow). The concentrations of GnRH-I or GnRH-II in the eluates of these cell extracts were determined by using specific RIA systems for GnRH-I or GnRH-II. The elution profiles of the immunoreactive neuropeptides extracted from T-cells are identical to those of the synthetic peptides (FIG. 7A). These results demonstrate the endogenous presence of the two neuropeptides, GnRH-I and GnRH-II, in normal circulating human T-cell populations.

Figure 7B:
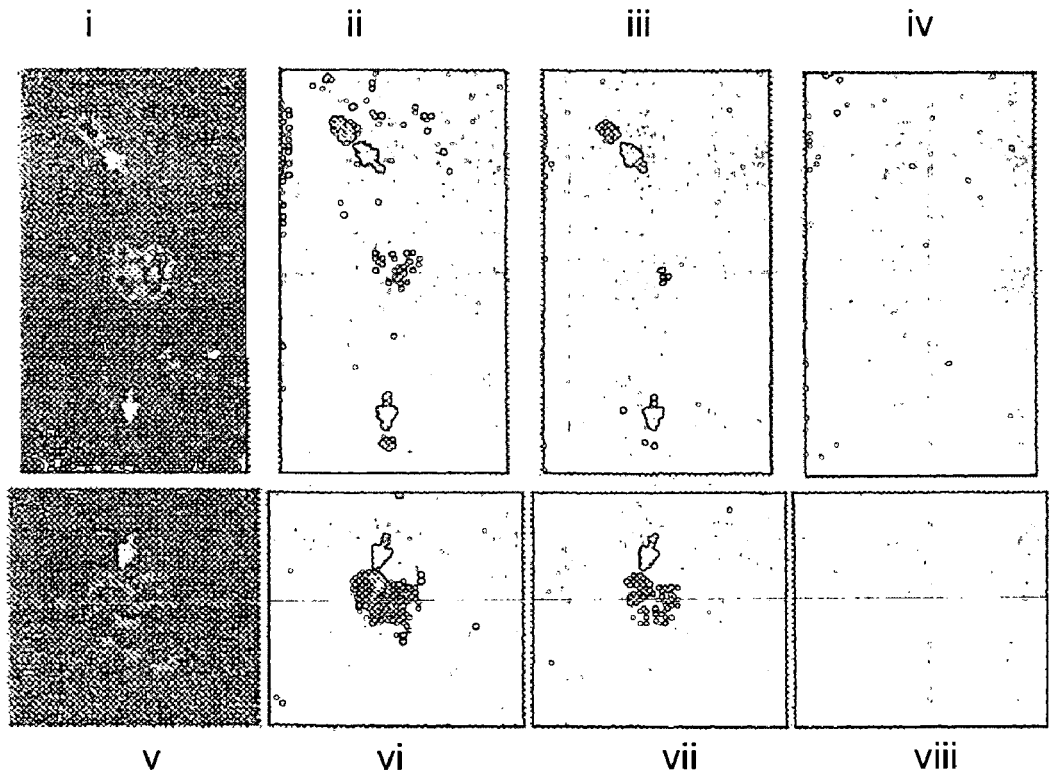
Figure 8A:
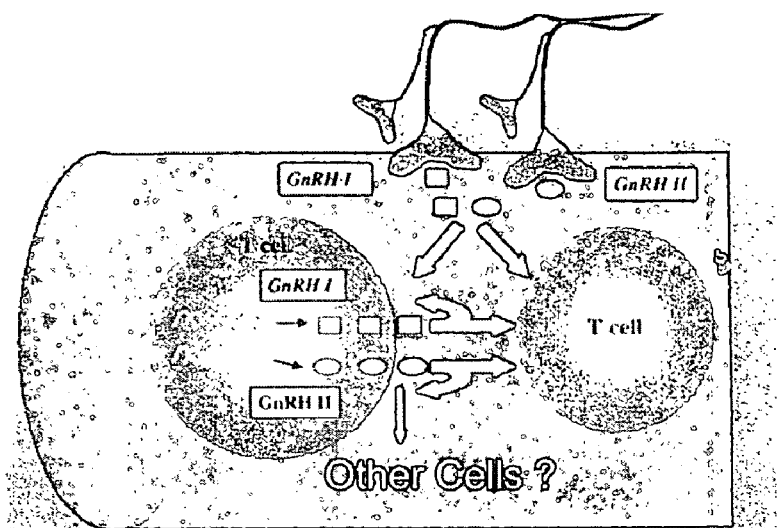
FIGS. 8A-8C present a proposed scheme of events in the process of GnRH-I and GnRH-II mediated enhancement of T-cell activity, incorporating explicit experimental evidence as well as implications derived therefrom.
Figure 8B:
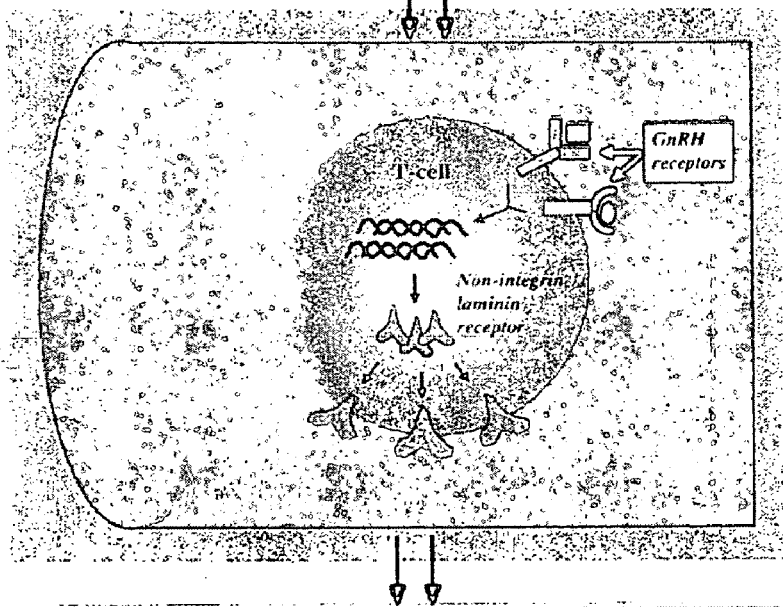
Figure 8C:
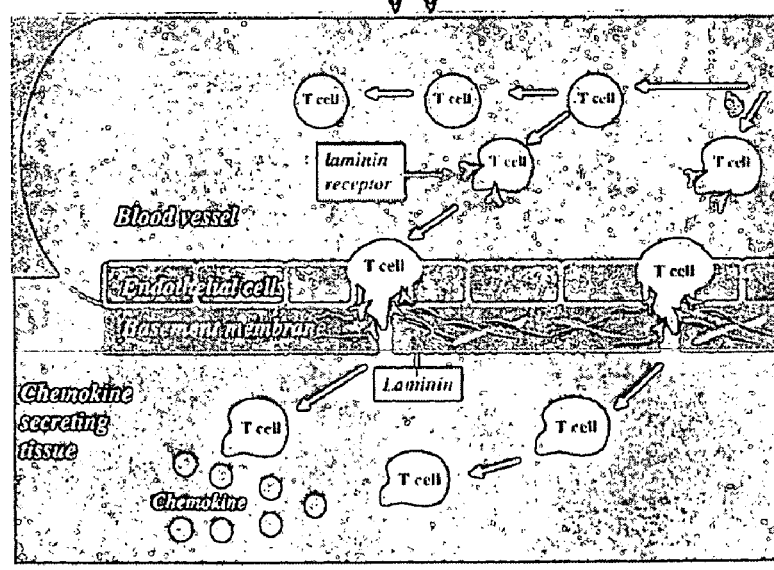

(c) Immunofluorescence staining: Further support for the presence of functional GnRH-I and GnRH-II mRNAs was obtained from double immunofluorescence staining signals for GnRH-I and GnRH-II in T-cells. FIGS. 7Bi-7Bviii demonstrate GnRH-I (FIGS. 7Biii and 7Bvii) and GnRH-II (FIGS. 7Bii and 7Bvi) immunoreactivty in peripheral human T-cells. However, comparing the phase micrographs (FIGS. 7Bi and 7By) to the immunofluorescent pictures (FIGS. 7Bii, 7Biii, 7Bvi and 7Bvii), one will notice that not all T-cells are GnRH-immunoreactive, indicating different degrees of GnRH expression. FIGS. 7Bvi and 7Bviii demonstrate that T-cells reacted with normal rabbit serum, followed by secondary antibodies, did not result in any staining, indicating the specificity of the GnRH staining.

Taken together, these experiments confirm the presence of both GnRH-I and GnRH-II gene products, and GnRH-I and GnRH-II proteins in cultured (Jurkat cells) and human peripheral T-cell lymphocytes. Furthermore, the positive immunofluorescence clearly identifies immunoreactive GnRH-I and GnRH-II translation products in many of the T-cells observed, suggesting the existence of an autocrine/paracrine mode of GnRH regulation of T-cell activity.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their genebank accession numbers mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

LIST OF REFERENCES

Additional References are Cited in the Text

1. Streilein, J. W. Immune privilege as the result of local tissue barriers and immunosuppressive microenvironments. *Curr Opin Immunol* 5, 428-432 (1993).
2. Pitt, D., Werner, P. & Raine, C. S. Glutamate excitotoxicity in a model of multiple sclerosis [see comments]. *Nat Med* 6, 67-70 (2000).
3. Smith, T., Groom, A., Zhu, B. & Turski, L. Autoimmune encephalomyelitis ameliorated by AMPA antagonists [see comments]. *Nat Med* 6, 62-66 (2000).
4. Merrill, J. E. & Jonakait, G. M. Interactions of the nervous and immune systems in development, normal brain homeostasis, and disease. *FASEB J* 9, 611-618 (1995).
5. Merrill, J. E. & Benveniste, E. N. Cytokines in inflammatory brain lesions: helpful and harmful. *Trends Neurosci* 19, 331-338 (1996).
6. Neumann, H. & Wekerle, H. Neuronal control of the immune response in the central nervous system: linking brain immunity to neurodegeneration. *J Neuropathol Exp Neurol* 57, 1-9 (1998).
7. Downing, J. E. & Miyan, J. A. Neural immunoregulation: emerging roles for nerves in immune homeostasis and disease [In Process Citation]. *Immunol Today* 21, 281-289 (2000).
8. Sternberg, E. M. Emotions and disease: from balance of humors to balance of molecules. *Nat Med* 3, 264-267 (1997).
9. Dorsam, G., Voice, J., Kong, Y. & Goetzl, E. J. Vasoactive intestinal peptide mediation of development and functions of T lymphocytes. *Ann NY Acad Sci* 921, 79-91 (2000).
10. Chen, A. et al. A second isoform of gonadotropin-releasing hormone is present in the brain of human and rodents. *FEBS Lett* 435, 199-203 (1998).
11. Gestrin, E. D., White, R. B. & Fernald, R. D. Second form of gonadotropin-releasing hormone in mouse: immunocytochemistry reveals hippocampal and periventricular distribution. *FEBS Lett* 448, 289-291 (1999).
12. Lescheid, D. W. et al. A second form of gonadotropin-releasing hormone (GnRH) with characteristics of chicken GnRH-II is present in the primate brain. *Endocrinology* 138, 5618-5629 (1997).
13. White, R. B., Eisen, J. A., Kasten, T. L. & Fernald, R. D. Second gene for gonadotropin-releasing hormone in humans. *Proc Natl Acad Sci USA* 95, 305-309 (1998).
14. Fink, G. Gonadotropin secretion and its control. in *The Physiology of Reproduction* (eds Knobil, E. & Neill, J. D.) 1349-1377 (Raven Press, New York, 1988).
15. Millar, R. P., Flanagan, C. A., Milton, R. C. & King, J. A. Chimeric analogues of vertebrate gonadotropin-releasing hormones comprising substitutions of the variant amino acids in positions 5, 7 and 8. Characterization of requirements for receptor binding and gonadotropin release in mammalian and avian pituitary gonadotropes. *J Biol Chem* 264, 21007-21013 (1989).
16. Wewer, U. M. et al. Altered levels of laminin receptor mRNA in various human carcinoma cells that have different abilities to bind laminin. *Proc Natl Acad Sci USA* 83, 7137-7141 (1986).
17. Hand, P. H., Thor, A., Schlom, J., Rao, C. N. & Liotta, L. Expression of laminin receptor in normal and carcinomatous human tissues as defined by a monoclonal antibody. *Cancer Research* 45, 2713-2719 (1985).
18. Martignone, S. et al. Prognostic significance of the 67-kilodalton laminin receptor expression in human breast carcinomas. *Journal of the National Cancer Institute* 85, 398-402 (1993).
19. Wang, K. S., Kuhn, R. J., Strauss, E. G., Ou, S. & Strauss, J. H. High-affinity laminin receptor is a receptor for Sindbis virus in mammalian cells. *J Virol* 66, 4992-5001 (1992).
20. Protopopova, E. V., Konavalova, S. N. & Loktev, V. B. [Isolation of a cellular receptor for tick-borne encephalitis virus using anti-idiotypic antibodies]. *Vopr Virusol* 42, 264-268 (1997).
21. Rieger, R., Edenhofer, F., Lasmezas, C. I. & Weiss, S. The human 37 kDa laminin receptor precursor interacts with the prion protein in eukaryotic cells [see comments]. *Nat Med* 3, 1383-1388 (1997).
22. Rieger, R. et al. Role of the 37 kDa laminin receptor precursor in the life cycle of prions. The human 37 kDa laminin receptor precursor interacts with the prion protein in eukaryotic cells [see comments]. *Transfus Clin Biol* 6, 7-16 (1999).
23. Levite, M. Neuropeptides, by direct interaction with T cells, induce cytokine secretion and break the commitment to a distinct T helper phenotype. *Proc Natl Acad Sci USA* 95, 12544-12549 (1998).

24. Canfield, S. M. & Khakoo, A. Y. The nonintegrin laminin binding protein (p67 LBP) is expressed on a subset of activated human T lymphocytes and, together with the integrin very late activation Antigen-6, mediates avid cellular adherence to Laminin1. *J-Immunol* 163, 3430-3440 (1999).
25. Levite, M., Cahalon, L., Hershkoviz, R., Steinman, L. & Lider, O. Neuropeptides, via specific receptors, regulate T cell adhesion to fibronectin. *J-Immunol* 160, 993-1000 issn: 0022-1767 (1998).
26. Levite, M. et al. Extracellular K(+) and opening of voltage-gated potassium channels activate T cell integrin function: physical and functional association between Kv1.3 channels and beta I integrins. *J Exp Med* 191, 1167-1176 (2000).
27. Reissmann, T., Schally, A. V., Bouchard, P., Riethmiiller, H. & Engel, J. The LHRH antagonist cetrorelix: a review. *Hum Reprod Update* 6, 322-331 (2000).
28. Sealfon, S. C., Weinstein, H. & Millar, R. P. Molecular mechanisms of ligand interaction with the gonadotropin-releasing hormone receptor. *Endocr Rev* 18, 180-205 (1997).
29. Springer, T. A. Traffic signals for lymphocyte recirculation and leukocyte emigration: the multistep paradigm. *Cell* 76, 301-314 (1994).
30. Lloyd, A. R., Oppenheim, J. J., Kelvin, D. J. & Taub, D. D. Chemokines regulate T cell adherence to recombinant adhesion molecules and extracellular matrix proteins. *J Immunol* 156, 932-938 (1996).
31. Johnston, J. A. et al. Human T lymphocyte chemotaxis and adhesion induced by vasoactive intestinal peptide. *J Immunol* 153, 1762-1768 (1994).
32. Kim, C. H. & Broxmeyer, H. E. Chemokines: signal lamps for trafficking of T and B cells for development and effector function. *J Leukoc Biol* 65, 6-15 (1999).
33. Suzuki, H. Expression of the 67-KD laminin-binding protein in human lymphomas [letter; comment]. *Hum Pathol* 30, 361-362 (1999).
34. Ota, T., Tanino, M., Kohno, H., Funamoto, H. & Odashima, S. Isolation and characterization of a low metastatic variant from EL-4 mouse T-lymphoma. *Clin Exp Metastasis* 10, 297-308 (1992).
35. Sarzotti, M., Baron, S. & Klimpel, G. R. EL-4 metastases in spleen and bone marrow suppress the NK activity generated in these organs. *Int J Cancer* 39, 118-125 (1987).
36. Maier, C. C., Marchetti, B., LeBoeuf, R. D. & Blalock, J. E. Thymocytes express a mRNA that is identical to hypothalamic luteinizing hormone-releasing hormone-mRNA. *Cell Mol Neurobiol* 12, 447-454 (1992).
37. Azad, N. et al. Immunoactivation enhances the concentration of luteinizing hormone-releasing hormone peptide and its gene expression in human peripheral T-lymphocytes. *Endocrinology* 133, 215-223 (1993).
38. Delgado, M. & Ganea, D. Cutting Edge: Is Vasoactive Intestinal Peptide a Th2 cytokine? *Journal of Immunology* 166, 2907-2912 (2001).
39. Grakoui, A. et al. The immunological synapse: a molecular machine controlling T cell activation [see comments]. *Science* 285, 221-227 (1999).
40. Malissen, B. Dancing the immunological two-step [comment]. *Science* 285, 207-208 (1999).
41. Levite, M. Nerve-driven immunity. The direct effects of neurotransmitters on T-cell function. *Ann NY Acad Sci* 917, 307-321 (2001).
42. Levite, M. Nervous immunity: neurotransmitters, extracellular K(+) and T-cell function. *Trends Immunol* 22, 2-5 (2001).
43. Miyamoto, K. et al. Identification of the second gonadotropin-releasing hormone in chicken hypothalamus: evidence that gonadotropin secretion is probably controlled by two distinct gonadotropin-releasing hormones in avian species. *Proc Natl Acad Sci USA* 81, 3874-3878 (1984).
44. Chen, A., Laskar-Levy, O., Ben Aroya, N. & Koch, Y. Transcriptional regulation of the human gonadotropin-releasing hormone II gene is mediated by a putative cAMP response element. *Endocrinology* (In Press) August 2001 (2001).
45. Jones, S. W. Chicken II luteinizing hormone-releasing hormone inhibits the M-current of bullfrog sympathetic neurons. *Neurosci Lett* 80, 180-184 (1987).
46. Troskie, B. et al. Chicken GnRH II-like peptides and a GnRH receptor selective for chicken GnRH II in amphibian sympathetic ganglia. *Neuroendocrinology* 65, 396-402 (1997).
47. Tensen, C. et al. Distinct efficacies for two endogenous ligands on a single cognate gonadoliberin receptor. *Eur J Biochem* 243, 134-140 (1997).
48. Illing, N. et al. Two gonadotropin-releasing hormone receptor subtypes with distinct ligand selectivity and differential distribution in brain and pituitary in the goldfish (*Carassius auratus*). *Proc Natl Acad Sci USA* 96, 2526-2531 (1999).
49. Palmon, A. et al. The gene for the neuropeptide gonadotropin-releasing hormone is expressed in the mammary gland of lactating rats. *Proc Natl Acad Sci USA* 91, 4994-4996 (1994).
50. Takagi, A., Imai, A. & Tamaya, T. Alternative gonadotropin-releasing hormone processing products secreted from endometrial carcinoma. *Oncol Rep* 7, 125-129 (2000).
51. Yin, H. et al. Expression of the messenger RNA for gonadotropin-releasing hormone and its receptor in human cancer cell lines. *Life Sci* 62, 2015-2023 (1998).
52. Hynes, R. O. Integrins: a family of cell surface receptors. *Cell* 48, 549-554 (1987).
53. Rao, N. C., Barsky, S. H., Terranova, V. P. & Liotta, L. A. Isolation of a tumor cell laminin receptor. *Biochem Biophys Res Commun* 111, 804-808 (1983).
54. Satoh, K. et al. Cloning of 67-kDa laminin receptor cDNA and gene expression in normal and malignant cell lines of the human lung. *Cancer Lett* 62, 199-203 (1992).
55. Martignone, S. et al. Characterization of two monoclonal antibodies directed against the 67 kDa high affinity laminin receptor and application for the study of breast carcinoma progression. *Clinical and Experimental Metastasis* 10, 379-386 (1992).
56. Koch, Y. et al. Production and characterization of an antiserum to synthetic gonadotropin-releasing hormone. *Biochem Biophys Res Commun* 55, 616-622 (1973).
57. Urbanski, H. F. et al. Regional expression of mRNA encoding a second form of gonadotropin-releasing hormone in the macaque brain. *Endocrinology* 140, 1945-1948 (1999).
58. Okuzawa, K. et al. Differences in salmon GnRH and chicken GnRH-II contents in discrete brain areas of male and female rainbow trout according to age and stage of maturity. *Gen Comp Endocrinol* 80, 116-126 (1990).
59. Leonard, M., Brice, M., Engel, J. D. & Papayannopoulou, T. Dynamics of GATA transcription factor expression during erythroid differentiation. *Blood* 82, 1071-1079 (1993).
60. Hayflick, J. S., Adelman, J. P. & Seeburg, P. H. The complete nucleotide sequence of the human gonadotropin-releasing hormone gene. *Nucleic Acids Res* 17, 6403-6404 (1989).

61. Rhoads, D. D., Dixit, A. & Roufa, D. J. Primary structure of human ribosomal protein S14 and the gene that encodes it. *Mol Cell Biol* 6, 2774-2783 (1986).

62. Hunter, W. M. & Greenwood, F. C. Preparation of iodine-131 labelled human growth hormone of high specific activity. *Nature* 194, 495-496 (1962).

What is claimed is:

1. A method of determining the response of an individual to GnRH-I or GnRH-II receptor mediated upregulation of T-cell activity, the method comprising:
   isolating a T-cell population from the individual;
   providing to the T-cell population an effective amount of a molecule selected as being capable of stimulating the activity of, or upregulating the expression level of, a GnRH-I or a GnRH-II receptor in said T-cell population, said molecule being selected from the group consisting of GnRH-I, GnRH-II, a naturally occurring GnRH-I analog capable of stimulating the activity of the GnRH-I receptor, a naturally occurring GnRH-II analog capable of stimulating the activity of the GnRH-II receptor, and an anti-GnRH-I receptor antibody capable of stimulating the activity of the GnRH-I receptor; and
   monitoring a T-cell activity of the T-cell population.

2. The method of claim 1, wherein the T-cell population is a non-activated T-cell population.

3. The method of claim 1, wherein said molecule is a naturally occurring GnRH-I analog capable of stimulating the activity of the GnRH-I receptor or a naturally occurring GnRH-II analog capable of stimulating the activity of the GnRH-II receptor.

4. The method of claim 1, wherein said molecule is an anti-GnRH-I receptor antibody capable of stimulating the activity of the GnRH-I receptor, which antibody is a monoclonal or a polyclonal antibody.

5. The method of claim 1, wherein said monitoring of a T-cell activity is effected by monitoring at least one parameter selected from the group consisting of 67 kDa non-integrin laminin receptor expression, laminin adhesion, chemotaxis, extravasation, migration and organ invasion.

6. A method of upregulating T-cell activity in a mammalian subject having sub-optimal T-cell activity, the method comprising providing, ex vivo, to T-cells obtained from a subject identified as having the sub-optimal T-cell activity, an effective amount of a molecule selected as being capable of stimulating the activity of, or upregulating the expression level of, the GnRH-I or the GnRH-II receptor in said T-cells, to thereby produce a treated T-cell population, wherein said molecule is selected from the group consisting of GnRH-I, GnRH-II, a naturally occurring GnRH-I analog capable of stimulating the GnRH-I receptor, a naturally occurring GnRH-II analog capable of stimulating the GnRH-II receptor, and an anti-GnRH-I receptor antibody capable of stimulating the GnRH-I receptor; and
   administering said treated T-cell population to the subject, thereby upregulating T-cell activity in the mammalian subject.

7. The method of claim 6, wherein said molecule is a naturally occurring GnRH-I analog capable of stimulating the GnRH-I receptor or a naturally occurring GnRH-II analog capable of stimulating the GnRH-II receptor.

8. The method of claim 6, wherein said molecule is an anti-GnRH-I receptor antibody capable of stimulating the GnRH-I receptor, which antibody is a monoclonal or a polyclonal antibody.

9. The method of claim 6, wherein the upregulating T-cell activity in a mammalian subject results in an increase in at least one T-cell activity selected from the group consisting of 67 KDa non-integrin laminin receptor expression, laminin adhesion, chemotaxis, extravasation, migration and organ invasion.

10. The method of claim 6, wherein said molecule is selected as being capable of stimulating the activity of, or upregulating the expression level of, the GnRH-I receptor.

11. The method of claim 10, wherein said molecule is GnRH-I.

12. The method of claim 6, wherein said molecule is selected as being capable of stimulating the activity of, or upregulating the expression level of, the GnRH-II receptor.

13. The method of claim 12, wherein said molecule is GnRH-II.

14. A method of treating a disease or condition in which upregulation of T-cell activity has therapeutic value, in a mammalian subject, the method comprising providing, ex vivo, to T-cells obtained from a subject identified as having such a disease or condition, a therapeutically effective amount of a molecule selected as being capable of stimulating the activity of, or upregulating the expression level of, the GnRH-I or the GnRH-II receptor, said amount being sufficient to upregulate a T-cell activity, to thereby produce a treated T-cell population, wherein said molecule is selected from the group consisting of GnRH-I, GnRH-II, a naturally occurring GnRH-I analog capable of stimulating the GnRH-I receptor, a naturally occurring GnRH-II analog capable of stimulating the GnRH-II receptor, and an anti-GnRH-I receptor antibody capable of stimulating the GnRH-I receptor; and
   administering said treated T-cell population to the subject, thereby treating the disease or condition in the mammalian subject.

15. The method of claim 14, wherein said molecule is a naturally occurring GnRH-I analog capable of stimulating the GnRH-I receptor or a naturally occurring GnRH-II analog capable of stimulating the GnRH-II receptor.

16. The method of claim 14, wherein said molecule is an anti-GnRH-I receptor antibody capable of stimulating the GnRH-I receptor, which antibody is a monoclonal or a polyclonal antibody.

17. The method of claim 14, wherein upregulating said T-cell activity in a mammalian subject results in an increase in at least one T-cell activity selected from the group consisting of 67 KDa non-integrin laminin receptor expression, laminin adhesion, chemotaxis, extravasation, migration and organ invasion.

18. The method of claim 14, wherein said disease or condition is selected from the group consisting of congenital immune deficiencies, acquired immune deficiencies, infection, and neoplastic disease.

19. The method of claim 14, wherein said molecule is selected as being capable of stimulating the activity of, or upregulating the expression level of, the GnRH-I receptor.

20. The method of claim 19, wherein said molecule is GnRH-I.

21. The method of claim 14, wherein said molecule is selected as being capable of stimulating the activity of, or upregulating the expression level of, the GnRH-II receptor.

22. The method of claim 21, wherein said molecule is GnRH-II.

23. A method of upregulating T-cell activity in a mammalian subject having sub-optimal T-cell activity, the method comprising:

stimulating an activity of, or upregulating the expression level of, the GnRH-I or GnRH-II receptor in an ex vivo T-cell population by providing to the T-cell population an effective amount of a molecule selected as being capable of stimulating an activity of, or upregulating the expression level of, the GnRH-I or GnRH-II receptor, thereby upregulating T-cell activity in the population, wherein said molecule is selected from the group consisting of GnRH-I, GnRH-II, a naturally occurring GnRH-I analog capable of stimulating the activity of the GnRH-I receptor, a naturally occurring GnRH-II analog capable of stimulating the activity of the GnRH-II receptor, and an anti-GnRH-I receptor antibody capable of stimulating the activity of the GnRH-I receptor, thereby producing a treated T-cell population; and administering said treated T-cell population to the mammalian subject.

24. A method in accordance with claim 23, wherein said T-cell population is an autologous T-cell population, with respect to the mammalian subject to whom the treated T-cell population is administered.

25. A method in accordance with claim 23, wherein said T-cell population is a syngeneic or allogeneic T-cell population, with respect to the mammalian subject to whom the treated T-cell population is administered.

26. A method of treating a disease or condition in which upregulation of T-cell activity has therapeutic value, in a mammalian subject having such a disease or condition, the method comprising:

stimulating an activity of, or upregulating the expression level of, the GnRH-I or GnRH-II receptor in an ex vivo T-cell population by providing to the T-cell population an effective amount of a molecule selected as being capable of stimulating an activity of, or upregulating the expression level of, the GnRH-I or GnRH-II receptor, thereby upregulating T-cell activity in the population, wherein said molecule is selected from the group consisting of GnRH-I, GnRH-II, a naturally occurring GnRH-I analog capable of stimulating the activity of the GnRH-I receptor, a naturally occurring GnRH-II analog capable of stimulating the activity of the GnRH-II receptor, and an anti-GnRH-I receptor antibody capable of stimulating the activity of the GnRH-I receptor, thereby producing a treated T-cell population; and administering said treated T-cell population to the mammalian subject.

27. A method in accordance with claim 26, wherein said T-cell population is an autologous T-cell population, with respect to the mammalian subject to whom the treated T-cell population is administered.

28. A method in accordance with claim 26, wherein said T-cell population is a syngeneic or allogeneic T-cell population, with respect to the mammalian subject to whom the treated T-cell population is administered.

* * * * *